(12) United States Patent
Romo et al.

(10) Patent No.: US 9,737,371 B2
(45) Date of Patent: Aug. 22, 2017

(54) CONFIGURABLE ROBOTIC SURGICAL SYSTEM WITH VIRTUAL RAIL AND FLEXIBLE ENDOSCOPE

(71) Applicant: AURIS SURGICAL ROBOTICS, INC., San Carlos, CA (US)

(72) Inventors: Enrique Romo, Dublin, CA (US); Frederic H. Moll, San Francisco, CA (US); David S. Mintz, Mountain View, CA (US); Mark Lown, Union City, CA (US); Siddarth Oli, Saint Therese (CA); Allen Jiang, Fremont, CA (US)

(73) Assignee: Auris Surgical Robotics, Inc., San Carlos, CA (US)

( * ) Notice: Subject to any disclaimer, the term of this patent is extended or adjusted under 35 U.S.C. 154(b) by 29 days.

(21) Appl. No.: 14/871,253

(22) Filed: Sep. 30, 2015

(65) Prior Publication Data

US 2016/0184032 A1  Jun. 30, 2016

Related U.S. Application Data

(60) Provisional application No. 62/057,936, filed on Sep. 30, 2014, provisional application No. 62/096,825, (Continued)

(51) Int. Cl.
*B25J 9/16* (2006.01)
*B25J 13/08* (2006.01)
(Continued)

(52) U.S. Cl.
CPC .............. *A61B 34/30* (2016.02); *A61B 10/04* (2013.01); *A61B 34/32* (2016.02); *B25J 9/1676* (2013.01);
(Continued)

(58) Field of Classification Search
CPC ......... A61B 34/30; A61B 34/32; A61B 34/37; A61B 2034/301; A61B 2034/302;
(Continued)

(56) References Cited

U.S. PATENT DOCUMENTS 9,226,796 B2 * 1/2016 Bowling ................ A61B 34/32
2004/0257021 A1  12/2004 Chang et al.
(Continued)

FOREIGN PATENT DOCUMENTS

EP  2392435 A2 *  6/2011  ................ B25J 9/16

OTHER PUBLICATIONS

PCT International Search Report and Written Opinion, PCT Application No. PCT/US15/53306, Feb. 4, 2016, 19 pages.

*Primary Examiner* — Spencer Patton
(74) *Attorney, Agent, or Firm* — Knobbe Martens Olson & Bear LLP

(57) ABSTRACT

Systems and methods for moving or manipulating robotic arms are provided. A group of robotic arms are configured to form a virtual rail or line between the end effectors of the robotic arms. The robotic arms are responsive to outside force such as from a user. When a user moves a single one of the robotic arms, the other robotic arms will automatically move to maintain the virtual rail alignments. The virtual rail of the robotic arm end effectors may be translated in one or more of three dimensions. The virtual rail may be rotated about a point on the virtual rail line. The robotic arms can detect the nature of the contact from the user and move accordingly. Holding, shaking, tapping, pushing, pulling, and rotating different parts of the robotic arm elicits different movement responses from different parts of the robotic arm.

25 Claims, 80 Drawing Sheets

Related U.S. Application Data filed on Dec. 24, 2014, provisional application No. 62/211,135, filed on Aug. 28, 2015.

(51) Int. Cl.
*A61B 34/30* (2016.01)
*A61B 10/04* (2006.01)
*A61B 34/32* (2016.01)
*G01L 5/00* (2006.01)
*A61B 34/37* (2016.01)
*A61B 17/00* (2006.01)
*A61B 90/00* (2016.01)

(52) U.S. Cl.
CPC .......... *B25J 9/1694* (2013.01); *B25J 13/085* (2013.01); *G01L 5/0052* (2013.01); *A61B 34/37* (2016.02); *A61B 2017/00477* (2013.01); *A61B 2034/301* (2016.02); *A61B 2034/305* (2016.02); *A61B 2090/064* (2016.02); *G05B 2219/39109* (2013.01); *G05B 2219/39319* (2013.01); *Y10S 901/09* (2013.01); *Y10S 901/46* (2013.01)

(58) Field of Classification Search
CPC . A61B 2034/303; B25J 9/1682; B25J 9/1694; B25J 9/0084; B25J 9/0087; B25J 9/1669; B25J 3/00; B25J 3/04; B25J 13/085; G05B 2219/39109; G05B 2219/39122; G05B 2219/39319
See application file for complete search history.

(56) References Cited

U.S. PATENT DOCUMENTS

| | | |
|---|---|---|
| 2005/0222714 A1 | 10/2005 | Nihei et al. |
| 2008/0231221 A1* | 9/2008 | Ogawa ............... B25J 5/007 318/568.12 |
| 2009/0287354 A1* | 11/2009 | Choi ............... B25J 9/1633 700/261 |
| 2010/0256812 A1* | 10/2010 | Tsusaka ............... A47L 9/24 700/254 |
| 2012/0071752 A1* | 3/2012 | Sewell ............... A61B 6/12 600/424 |
| 2013/0325030 A1 | 12/2013 | Hourtash et al. |
| 2014/0135985 A1 | 5/2014 | Coste-Maniere et al. |
| 2014/0222207 A1* | 8/2014 | Bowling ............... A61B 34/32 700/261 |
| 2014/0296870 A1 | 10/2014 | Stern et al. |
| 2015/0104284 A1* | 4/2015 | Riedel ............... B25J 9/0087 414/738 |
| 2015/0342695 A1* | 12/2015 | He ............... A61B 17/00234 606/130 |
| 2015/0359597 A1* | 12/2015 | Gombert ............ A61B 19/2203 606/130 |

* cited by examiner

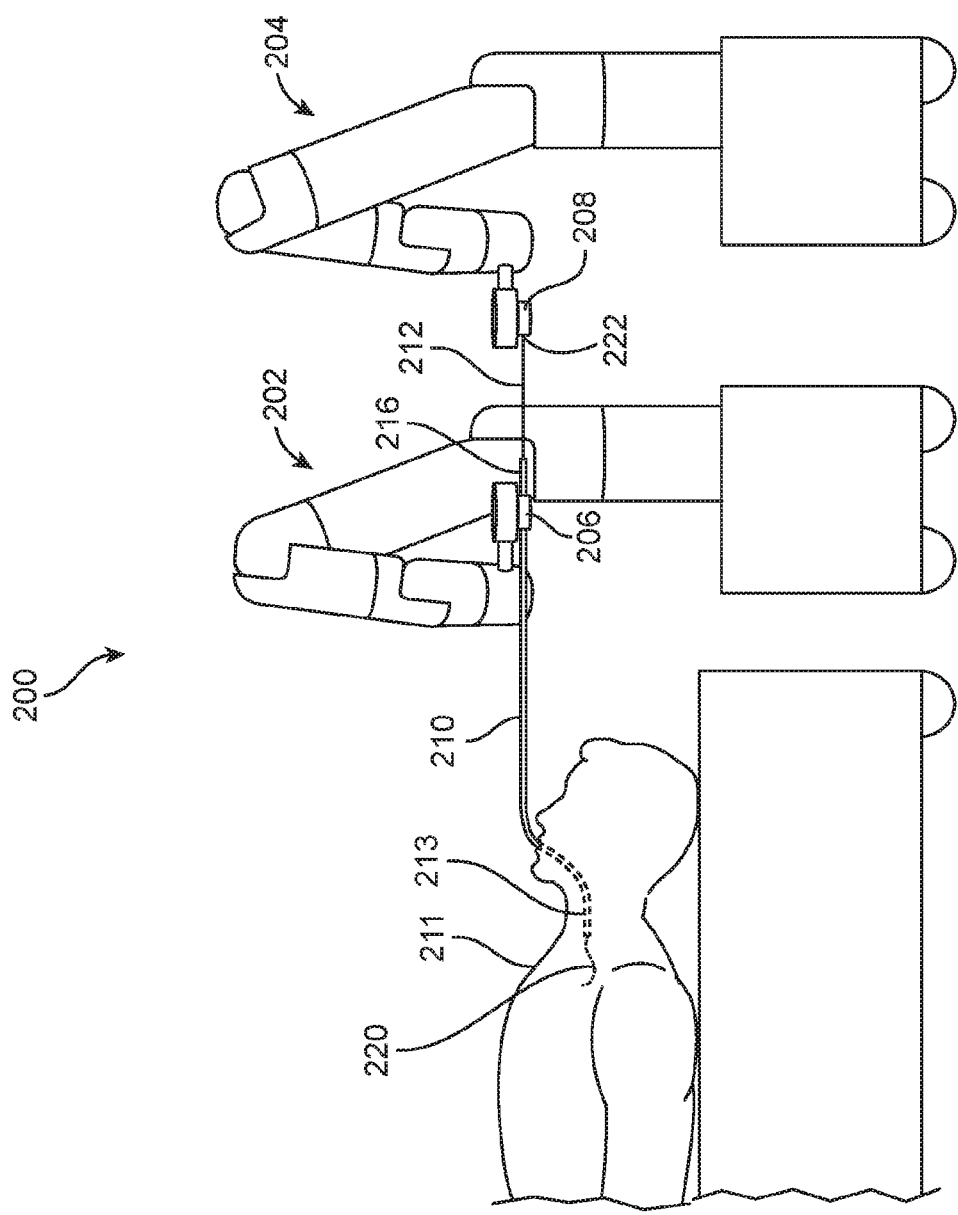

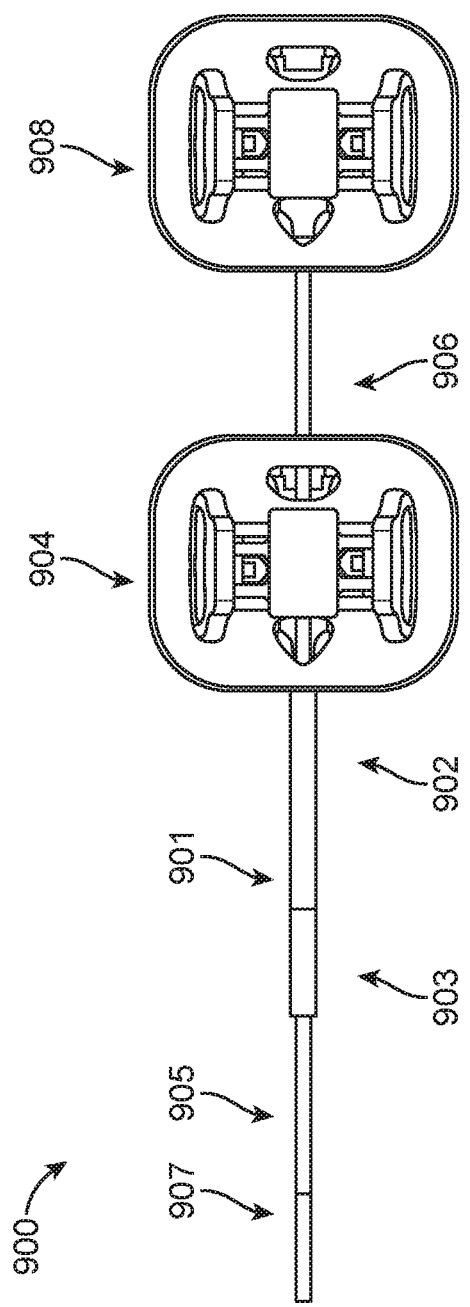

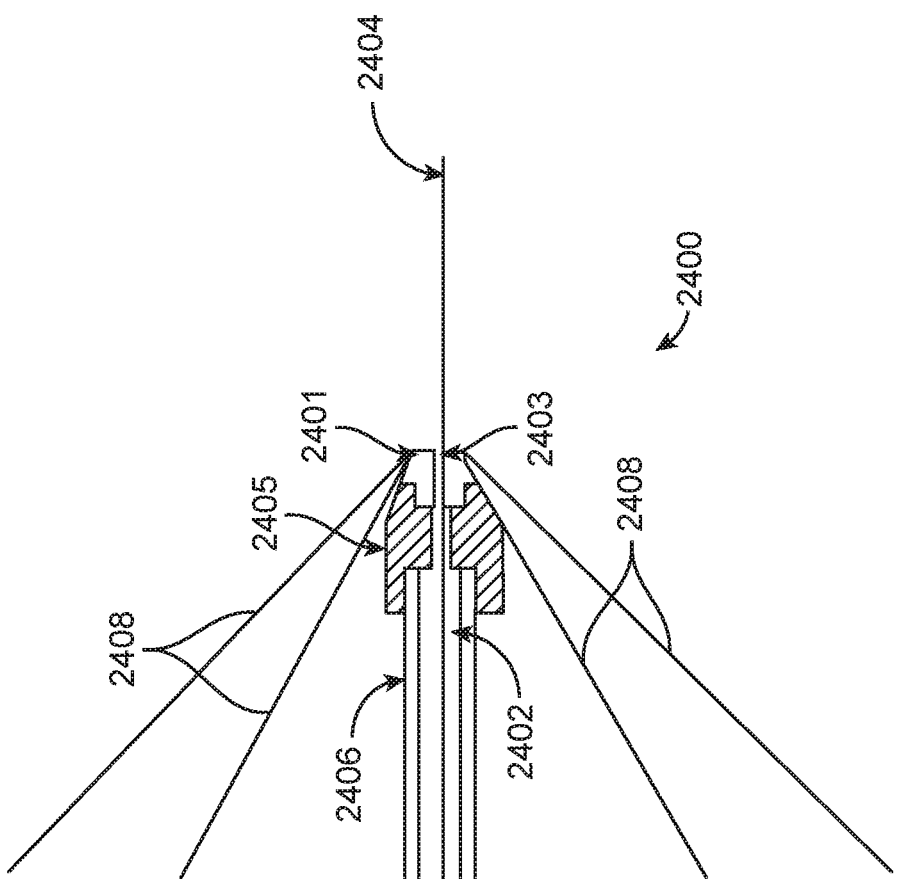
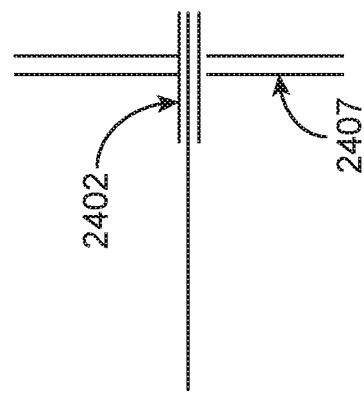
FIG. 24

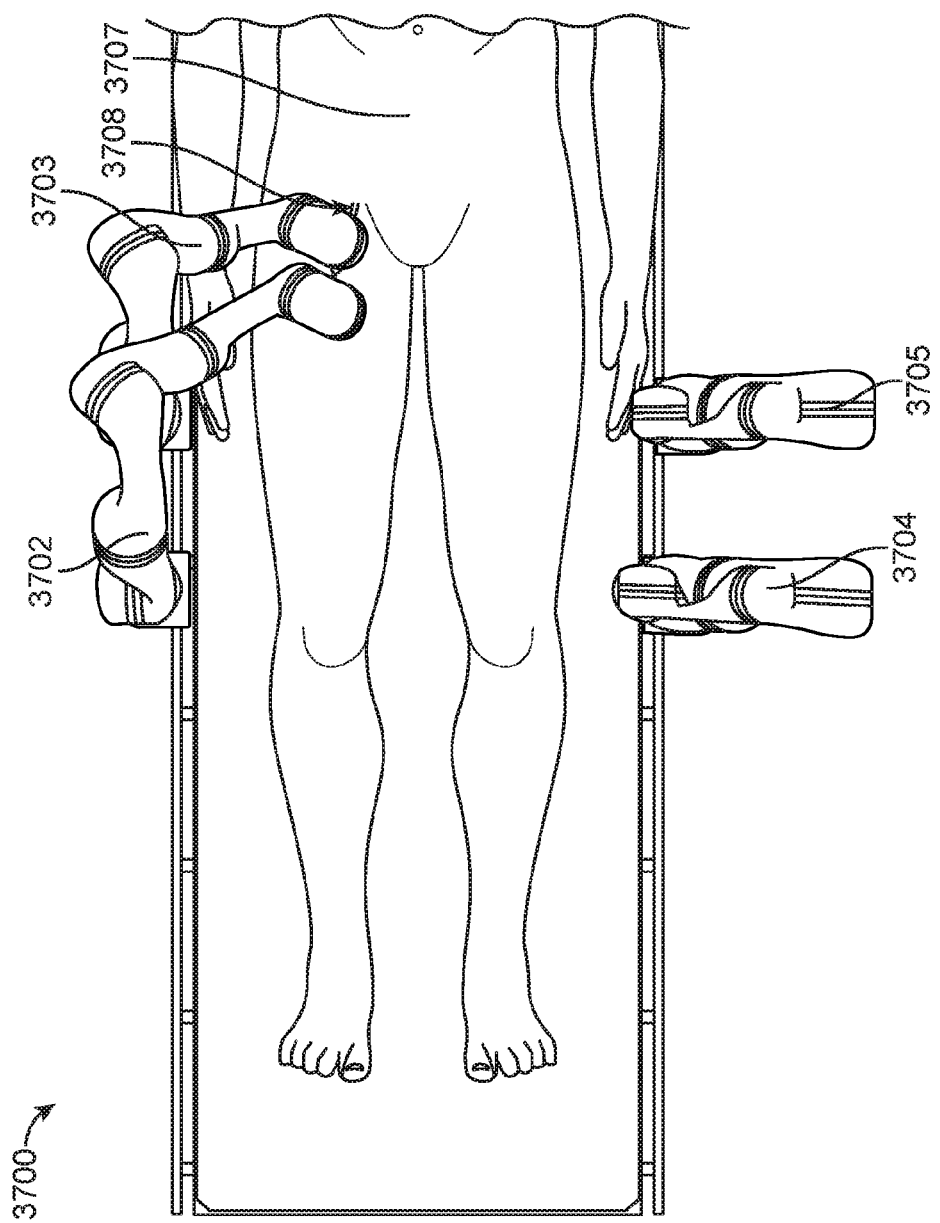

CONFIGURABLE ROBOTIC SURGICAL SYSTEM WITH VIRTUAL RAIL AND FLEXIBLE ENDOSCOPE

CROSS-REFERENCE

This application claims the benefit of U.S. Provisional Applications Nos. 62/057,936, filed Sep. 30, 2014, 62/096,825, filed Dec. 24, 2014, and 62/211,135, filed Aug. 28, 2015, which applications are incorporated herein by reference.

The subject matter of this application is related to the subject matter of the following patent applications: provisional application Ser. No. 62/096,825; provisional application Ser. No. 62/057,936; provisional application Ser. No. 61/940,180; application Ser. No. 14/523,760; application Ser. No. 14/542,373; application Ser. No. 14/542,387; application Ser. No. 14/542,403; and application Ser. No. 14/542,429, which are incorporated herein by reference.

FIELD OF THE INVENTION

The field of the present application pertains to medical devices. More particularly, the field of the invention pertains to a mechanical tool and manufacturing techniques for catheters and endoscopes for robotic assisted surgery as well as systems and tools for robotic-assisted endolumenal or other surgery.

BACKGROUND

Endoscopy is a widely-used, minimally invasive technique for both imaging and delivering therapeutics to anatomical locations within the human body. Typically a flexible endoscope is used to deliver tools to an operative site inside the body—e.g., through small incisions or a natural orifice in the body (nasal, anal, vaginal, urinary, throat, etc.)—where a procedure is performed. Endoscopes may have imaging, lighting and steering capabilities at the distal end of a flexible shaft enabling navigation of non-linear lumens or pathways.

Endolumenal surgical applications involve positioning and driving an endoscope to a desired anatomical position. To assist with endolumenal navigation, the endoscopes often have a means to articulate a small distal bending section. Today's endoscopic devices are typically hand held devices with numerous levers, dials, and buttons for various functionalities, but offer limited performance in terms of articulation. For control, physicians control the position and progress of the endoscope by manipulating the levers or dials in concert with twisting the shaft of the scope. These techniques require the physician to contort their hands and arms when using the device to deliver the scope to the desired position. The resulting arm motions and positions are awkward for physicians; maintaining those positions can also be physically taxing. Thus, manual actuation of bending sections is often constrained by low actuation force and poor ergonomics.

Today's endoscopes also require support personnel to both deliver, operate and remove operative, diagnostic or therapeutic devices from the scope while the physician maintains the desired position. Today's endoscopes also utilize pull wires that create issues with curve alignment and muscling. Some procedures require fluoroscopy or segmented CT scans to assist in navigating to the desired location, particularly for small lumen navigation.

Therefore, it would be beneficial to have a system and tools for endolumenal robotic procedures that provide improved ergonomics, usability, and navigation. Application of these technologies may also be applied to other surgical procedures, such as vascular surgeries. It would also be beneficial to have an improved control for catheters and endoscopes to have a controlled bend with a neutral axis remaining constant during bending operations. Additionally it would be beneficial to have an improved method for manufacturing such catheters and endoscopes, i.e., endoscopes and catheters that maintain a neutral axis despite the bending, stretching, and articulating that occurs during use in anatomical structures and spaces.

SUMMARY

An embodiment of the present invention provides a sheath with a lumen therethrough, having a controllable and articulable distal end, which is mounted to a first robotic arm having at least 3 DOF, but preferably 6 or more DOF. This embodiment also includes a flexible endoscope having a controllable and articulable distal end, a light source and video capture unit at the distal end thereof, and at least one working channel extending therethrough. The flexible endoscope is slidingly disposed in the lumen of the sheath, and is mounted to a second robotic arm having at least 3 DOF, but preferably 6 or more DOF. Further included are first and second modules, operatively coupled, respectfully, to the proximal ends of the sheath and flexible endoscope. The modules are mounted to the first and second robotic arms, thereby mounting the sheath and flexible endoscope to first and second robotic arms, respectively. The modules provide the mechanics to steer and operate the sheath and flexible endoscope, and receive power and other utilities from the robotic arms. The robotic arms are positioned such that the first module is distal to the second module and the proximal end of the sheath is distal to the proximal end of the flexible endoscope. Movement of the first and second robotic arms relative to each other and relative to the patient causes movement of the sheath relative to the flexible endoscope and movement of either relative to the patient.

In one embodiment the robots are positioned relative to each other such that the sheath and flexible endoscope are in a substantially straight (e.g., approximately 180 degree angle), co-axially aligned configuration between the first and second robotic arms, forming a "virtual rail" between the robotic arms. It is to be noted that the virtual rail may take on angles ranging from 90-180 degrees. Movement of the robotic arms relative to each other provide axial motion of the sheath and flexible endoscope relative to each other and the patient, while maintaining the virtual rail between the robotic arms.

The first and second robotic arms may be on separate mobile carts or on the same mobile cart. The mobile carts permit transporting the arms between procedure rooms or moving within a procedure room to better accommodate necessary equipment and the patient bead. Alternatively, though less preferred, the robotic arms could be fixed to the floor or bed.

The present invention alternatively provides multiple modules for different procedures, where the robotic arms retrieve a desired module from a storage place, e.g., a module exchange table or stand, located in the procedure room. Each module or module pair is designed for a specific type of procedure.

The modules with the sheath and flexible endoscope combination can navigate narrow lumens within the human body (e.g., bronchial and other lung airways, blood vessels, urinary tract inter alia). Additional modules may include laproscopic (single or dual port), microsurgical modules (which may also have a sheath and flexible endoscope arrangement, but sized appropriately for the eye or other microsurgical site). Alternatively the microsurgical modules may be configured to hold rigid instruments sized appropriately for the scale of the surgery.

In embodiments in accordance with the present invention the sheath and flexible endoscope comprising a shaft having a proximal end, a distal end and a controllable bending section, where preferably the controllable bending section is a distal bending section. At least one tendon-conduit, preferably four extend through a wall of the shaft wall from the proximal end to a distal portion of the controllable bending section, preferably the distal end. Preferably, the shaft has an approximate circular or elliptical cross section. At least one tendon, preferably four extend through each of the at least one tendon-conduits. The tendon-conduits extend through the shaft wall approximately parallel to a central axis of the shaft from the proximal end up to a helix section of the shaft, and where the tendon-conduits extend through the shaft wall in a helixed or spiral pattern relative to the central axis up to a proximal portion of the controllable bending sections, and where the tendon-conduits extend through the shaft wall approximately parallel to the central axis up to a distal portion of the controllable bending section. Preferably, the controllable bending section is at the distal end of the shaft. The at least on tendon is secured to the distal portion of the controllable bending section, such that tensioning the at least one tendon causes the controllable bending section to articulate.

Systems, devices, and methods for robotically assisted endoscopic surgery are disclosed. An exemplary robotic surgery system may comprise first and second robotic arms and a controller for operating the robotic arms. The first and second robotic arms may comprise first and second device manipulators, respectively, that can be coupled to endoscopic tool(s). The first and second device manipulators may be configured to align to form a virtual rail to operate the endoscopic tool(s). The first and/or second robotic arms may be movable in a way to preserve the virtual rail alignment, thereby maintaining the proper and/or desired alignment of the endoscopic tool(s). The controller may be configured to move the first and second device manipulators in a way to maintain the virtual rail alignment. One or more of the first or second robotic arms may be responsive to forces exerted on it by the user and forces exerted on one of the robotic arms may cause both arms to move in coordination with one another so that the virtual rail alignment is maintained. The virtual rail formed by the first and second robotic arms or device manipulators may be translated in one or more of the X-axis, Y-axis, or Z-axis (i.e., horizontally and/or vertically). The virtual rail may also be pivoted about any point along the virtual line formed by the first and second robotic arms or device manipulators such as at the center of one of the device manipulators, a point between the first and second device manipulators, or a point beyond the line segment formed by the first and second device manipulators. In some embodiments, the system may further comprise a third robotic arm which may be operated by the controller and may be configured to form the virtual rail with the first and second robotic arms. The system may further comprise additional robotic arms operable by the controller and configured to form the virtual rail.

Systems, devices, and methods for user manipulation of robotic surgery systems are also disclosed. A robotic arm may be responsive to a variety of different inputs from the forces exerted on it from a user. The user may exert a force on the robotic arm, such as a tap, a push, a pull, a double tap or plurality of taps, a hold, or a shake, to name a few. The robotic force may detect the force exerted and determine the intent of the user based on the characteristics of the detected force. Such characteristics may include the location, magnitude, direction, and timing of the exerted force. Based on the determined user intent, the robotic arm may move in a predetermined pattern.

Aspects of the present disclosure provide methods of moving a system of robotic arms. A system of robotic arms may be provided. The system may comprise a first robotic arm and a second robotic arm. The first and second robotic arms may be at a predetermined distance and orientation relative to one another. The first robotic arm may detect a force exerted thereon. The first robotic arm may automatically move in response to the detected force. The first robotic arm may move with a first movement vector. The second robotic arm may automatically move in response to the detected force such that the predetermined distance and orientation between the first and second robotic arms is maintained. The second robotic arm may move with a second movement vector.

The predetermined distance and orientation between the first and second robotic arms may comprise a linear alignment between the first and second robotic arms such as a linear alignment between interface ends of the first and second robotic arms. In automatically moving the first robotic arm, the interface end of the first robotic arm may be pivoted about a point on a line formed by the first and second robotic arms. In automatically moving the second robotic arm, the interface end of the second robotic arm may be pivoted about the point on the line formed by the first and second robotic arms. The point on the line may be between the interface ends of the first and second robotic arms or beyond the interface ends of the first and second robotic arms.

In automatically moving the second robotic arm in response to the detected force such that the predetermined distance and orientation between the first and second robotic arms is maintained, the first and second robotic arms may be translated in unison along one or more of an X-axis, a Y-axis, or a Z-axis. In some embodiments, the first movement vector and the second movement vector are the same. In other embodiments, the first movement vector and the second movement vector are different.

The system of robotic arms may further comprise a third robotic arm. The first, second, and third robotic arms which may be at the predetermined distance and orientation relative to one another. The third robotic arm may automatically move in response to the detected force such that the predetermined distance and orientation between the first, second, and third robotic arms is maintained. The third robotic arm may move with a third movement vector. The predetermined distance and orientation between the first, second, and third robotic arms may comprise a linear alignment between the first, second, and third robotic arms such as a linear alignment between interface ends of the first, second, and third robotic arms.

In automatically moving the first robotic arm, the interface end of the first robotic arm may be pivoted about a point on a line formed by the first, second, and third robotic arms. In automatically moving the second robotic arm, the interface end of the second robotic arm may be pivoted about the point on the line formed by the first, second, and third robotic arms. In automatically moving the third robotic arm, the interface end of the third robotic arm may be pivoted about the point on the line formed by the first, second, and third robotic arms. The point on the line may be between two or more of the interface ends of the first, second, or third robotic arms or beyond two or more of the interface ends of the first, second, or third robotic arms. In automatically moving the third robotic arm in response to the detected force such that the predetermined distance and orientation between the first, second, and third robotic arms is maintained, the first, second, and third robotic arms may be translated in unison along one or more of an X-axis, a Y-axis, or a Z-axis. In some embodiments, two or more of the first movement vector, the second movement vector, and the third movement vector are the same. In other embodiments, two or more of the first movement vector, the second movement vector, and third movement vector are different.

In some embodiments, the first robotic arm may detect the force exerted on the first robotic arm comprises by detecting a torque exerted on a joint of the first robotic arm. The force exerted on the first robotic arm may be detected during an operation on a patient.

In some embodiments, a movement mode of the system of robotic arms may be enabled in response to the detected force. The movement mode of the system of robotic arms may comprise one or more of an admittance mode or an impedance mode. The movement mode of the system may be disabled after the first and second robotic arms have moved.

Aspects of the present disclosure provide systems of robotic arms. An exemplary system may comprise a first robotic arm, a second robotic arm, and a controller. The first robotic arm may comprise a force sensor configured to detect a force exerted on the first robotic arm. The first and second robotic arms may be at a predetermined distance and orientation relative to one another. The controller may be coupled to the first and second robotic arms. The controller may be configured to (i) automatically move the first robotic arm with a first movement vector in response to the detected force and (ii) automatically move the second robotic arm with a second movement vector in response to the detected force such that the predetermined distance and orientation between the first and second robotic arms is maintained.

The predetermined distance and orientation between the first and second robotic arms may comprise a linear alignment between the first and second robotic arms, such as a linear alignment between interface ends of the first and second robotic arms. The controller may be configured to pivot the interface ends of the first and second robotic arms about a point on a line formed by the first and second robotic arms. The point on the line may be between the interface ends of the first and second robotic arms or beyond the interface ends of the first and second robotic arms.

The controller may be configured to translate the first and second robotic arms in unison along one or more of an X-axis, a Y-axis, or a Z-axis. In some embodiments, the first movement vector and the second movement vector are the same. In other embodiments, the first movement vector and the second movement vector are different.

The system may further comprise a third robotic arm. The first, second, and third robotic arms may be at the predetermined distance and orientation relative to one another. The controller may be configured to automatically move the third robotic arm with a third movement vector in response to the detected force such that the predetermined distance and orientation between the first, second, and third robotic arms is maintained. The predetermined distance and orientation between the first, second, and third robotic arms may comprise a linear alignment between the first, second, and third robotic arms such as a linear alignment between interface ends of the first, second, and third robotic arms.

The controller may be configured to pivot the interface ends of the first, second, and third robotic arms about a point on a line formed by the first, second, and third robotic arms. The point on the line may be between two or more of the interface ends of the first, second, or third robotic arms or beyond two or more of the interface ends of the first, second, or third robotic arms. The controller may be configured to translate the first, second, and third robotic arms in unison along one or more of an X-axis, a Y-axis, or a Z-axis. In some embodiments, two or more of the first movement vector, the second movement vector, and the third movement vector are the same. In other embodiments, two or more of the first movement vector, the second movement vector, and third movement vector are different.

The first robotic arm may comprise at least one joint and at least one link. The force sensor of the first robotic arm may comprise a torque sensor coupled to the at least one joint. The first robotic arm may comprise at least one joint and at least one link. The force sensor of the first robotic arm may comprise a tactile sensor coupled to the at least one link.

The controller may be configured to enable a movement mode of the system of robotic arms in response to the detected force. The movement mode of the system of robotic arms may comprise one or more of an admittance mode or an impedance mode. The controller may be configured to disable the movement mode of the system after the first and second robotic arms have moved.

Aspects of the present disclosure provide methods of moving a robotic arm.

A force exerted on the robotic arm may be detected. The exerted force may comprise a force vector and a timing characteristic. A user intent may be determined based on the force vector and timing characteristic of the detected force. The robotic arm may be automatically moved in response to the determined user intent. Detecting the force exerted on the robotic arm may include detecting whether the force is exerted on a joint, a link, or an interface end of the robotic arm or one or more of detecting the force with a torque sensor coupled to a joint of the robotic arm or detecting the force with a tactile sensor coupled to a link of the robotic arm. Determining the user intent may comprise determining whether the exerted force is one or more of a hold, a push, a pull, a tap, a plurality of taps, a rotation, or a shake of at least a portion of the robotic arm.

A movement mode of the robotic arm may be enabled before automatically moving the robotic arm. The movement mode of the robotic arm may be disabled after automatically moving the robotic arm. To enable the movement mode, an instruction may be received from a foot pedal in communication with the robotic arm, a joystick in communication with the robotic arm, a voice command, a detected light, or a computing device in communication with the robotic arm, to name a few examples. The movement mode may comprise one or more of an impedance mode or an admittance mode.

To determine the user intent, the gesture type of the user may be detected. Determining the user intent may include determining that the force exerted on the robotic arm comprises at least one tap on a joint of the robotic arm, and the joint of the robotic arm may be automatically moved while maintaining a position of at least one other joint or interface end of the arm in response to the at least one tap. Determining the user intent may include determining that the force exerted on the robotic arm comprises a pull on an interface end of the robotic arm while a position of a joint of the robotic arm is maintained, and the interface end of the robotic arm may be rotated. Determining the user intent may include determining that the force exerted on the robotic arm comprises a push or pull on an interface end of the robotic arm, and the interface end of the robotic arm may be automatically moved in response to the push or pull on the interface end and the whole robotic arm may be automatically moved to follow the movement of the interface end.

In some embodiments, an initial position of the robotic arm may be memorized before moving the robotic arm. The robotic arm may be moved back to the initial position after moving the robotic arm in response to the determined user intent.

Aspects of the present disclosure may provide robotic arm systems. An exemplary robotic arm system may comprise a robotic arm and a controller. The robotic arm may comprise a force sensor configured to detect a force exerted on the robotic arm. The exerted force may comprise a force vector and a timing characteristic. The controller may be coupled to the robotic arm. The controller may be configured to (i) determine a user intent based on the force vector and timing characteristic of the detected force and (ii) automatically move the robotic arm in response to the determined user intent.

The force sensor may be configured to detect whether the force is exerted on a joint, a link, or an interface end of the robotic arm. The force sensor may comprise one or more of a torque sensor coupled to a joint of the robotic arm or a tactile sensor coupled to a link of the robotic arm.

The controller may be configured to determine the user intent by determining whether the exerted force is one or more of a hold, a push, a pull, a tap, a plurality of taps, a rotation, or a shake of at least a portion of the robotic arm. The controller may be configured to enable a movement mode of the robotic arm before automatically moving the robotic arm. The controller may be configured to disable the movement mode of the robotic arm after automatically moving the robotic arm.

The system may further comprise an external control unit in communication with the controller to enable the movement mode. The external control unit may comprise one or more of a foot pedal, a joystick, a microphone, a light detector, or a computing device. The movement mode may comprise one or more of an impedance mode or an admittance mode.

The robotic arm may comprise a joint, a link, and an interface end.

The controller may be configured to determine the user intent in many ways through gesture sensing for example. The controller may be configured to determine the user intent by determining that the force exerted on the robotic arm comprises at least one tap on the joint and automatically move the robotic arm by automatically moving the joint of the robotic arm while maintaining a position of at least one other joint or the interface end of the arm in response to the at least one tap. The controller may be configured to determine the user intent by determining that the force exerted on the robotic arm comprises a pull on the interface end of the robotic arm while a position of the joint of the robotic arm is maintained and automatically move the robotic arm by rotating the interface end of the robotic arm. The controller may be configured to determine the user intent by determining that the force exerted on the robotic arm comprises a push or pull on the interface end of the robotic arm and automatically move the robotic arm by automatically moving the interface end of the robotic arm in response to the push or pull on the interface end and by automatically moving the whole robotic arm to follow the movement of the interface end.

The controller may be configured to memorize an initial position of the robotic arm before moving the robotic arm. The controller may be configured to move the robotic arm back to the initial position after moving the robotic arm in response to the determined user intent.

BRIEF DESCRIPTION OF THE DRAWINGS

FIG. 2A illustrates a robotic surgery system, in accordance with many embodiments.

FIG. 9 is an illustration of a robotic catheter that may be used in conjunction with robotic system 100 from FIG. 1, in accordance with an embodiment of the present invention.

FIGS. 12A, 12B, 12C, 12D, 12E, 12F, 12G, 12H, 12I, 12J, and 12K illustrate muscling and curve alignment phenomena that manifest in previous flexible instruments and the improvement shown by an embodiment of the present invention.

FIG. 24 illustrates a system for manufacturing a flexible endoscopic device, in accordance with an embodiment of the present invention.

FIGS. 37A, 37B, 37C, and 37D illustrate a series of top views of a vascular procedure where the use of mechanical arms reduces catheter buckling and wasted length, in accordance with an embodiment of the present invention.

DETAILED DESCRIPTION

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview.

An endolumenal surgical robotic system provides the surgeon with the ability to sit down in an ergonomic position and control a robotic endoscopic tool to the desired anatomical location within a patient without the need for awkward arm motions and positions.

The robotic endoscopic tool has the ability to navigate lumens within the human body with ease by providing multiple degrees of freedom at least two points along its length. The tool's control points provide the surgeon with significantly more instinctive control of the device as it navigates a tortuous path within the human body. The tip of the tool is also capable of articulation from zero to ninety degrees for all three hundred and sixty degrees of roll angles.

The surgical robotic system may incorporate both external sensor-based and internal vision-based navigation technologies in order to assist the physician with guidance to the desired anatomical location within the patient. The navigational information may be conveyed in either two-dimensional display means or three-dimensional display means.

System Components.

Figure 1:
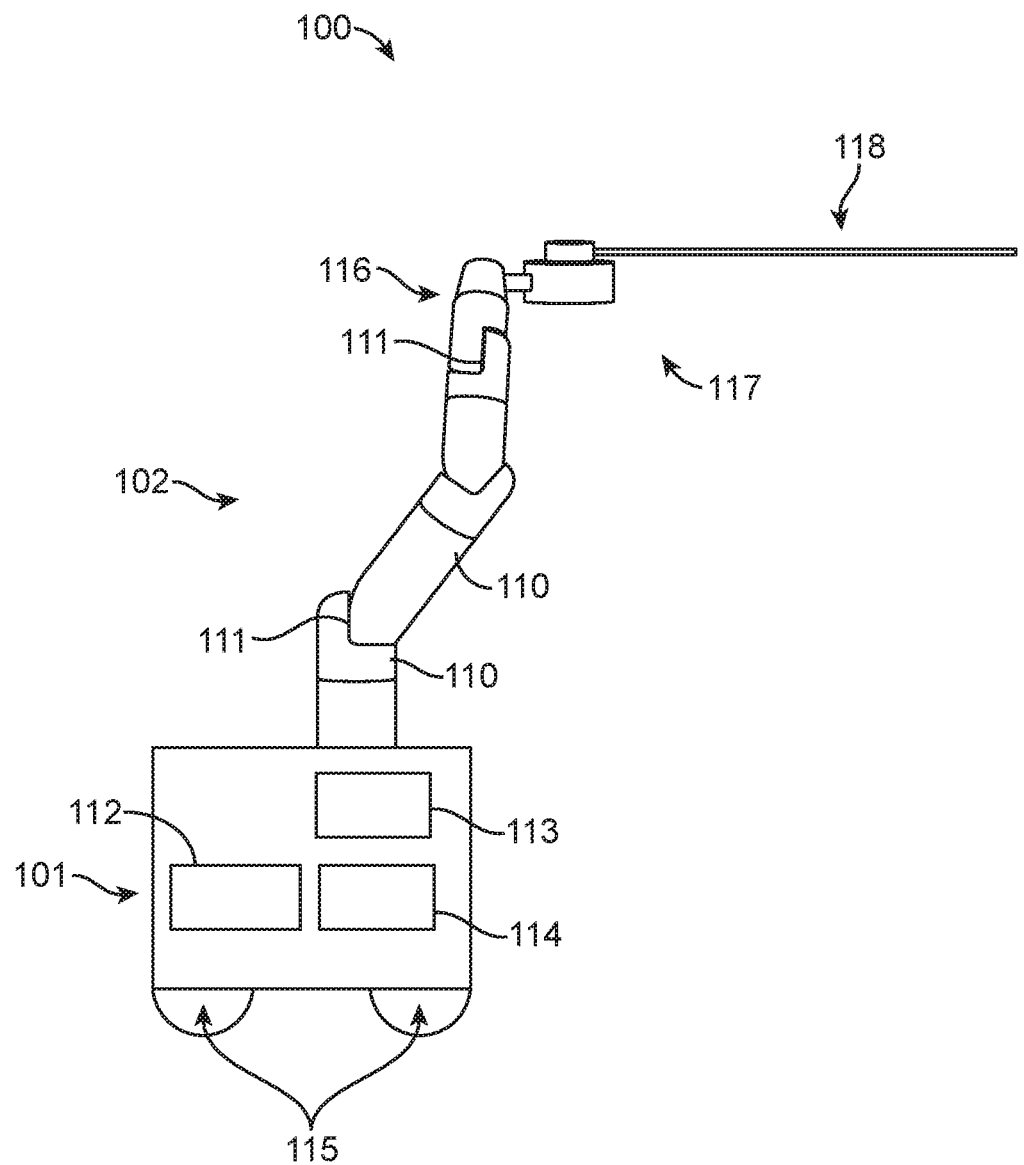
FIG. 1 illustrates a robotic endoscopic system, in accordance with many embodiments.

FIG. 1 is a robotic endoscopic system, in accordance with an embodiment of the present invention. As shown in FIG. 1, robotic system 100 may comprises a system cart 101 with at least one mechanical arm, such as arm 102. The system cart 101 may be in communication with a remotely-located command console (not shown). In practice, the system cart 101 may be arranged to provide access to a patient, while a physician may control the system 100 from the comfort of the command console. In some embodiments, the system 100 may be integrated into the operating table or bed for stability and access to the patient.

Within system 100, arm 102 may be fixedly coupled to a system cart 101 that contains a variety of support systems, including control electronics, power sources and optical sources in some embodiments. The arm 102 may be formed from a plurality of linkages 110 and joints 111 to enable access to the patient's operative region. The system cart 101 may contain source of power 112, pneumatic pressure 113, and control and sensor electronics 114—including components such as central processing unit, data bus, control circuitry, and memory—and related actuators or motors that may drive arms such as arm 102. Power may be conveyed from the system cart 101 to the arm 102 using a variety of means known to one skilled in the art such as electrical wiring, gear heads, air chambers. The electronics 114 in system cart 101 may also process and transmit control signals communicated from a command console.

The system cart 101 may also be mobile, as shown by the wheels 115. In some embodiments, the system cart may capable of being wheeled to the desired location near the patient. System cart(s) 101 may be located in various locations in the operating room in order to accommodate space needs and facilitate appropriate placement and motion of modules and instruments with respect to a patient. This capability enables the arms to be positioned in locations where they do not interfere with the patient, doctor, anesthesiologist or any supportive surgical equipment required for the selected procedure. During procedures, the arms with instruments will work collaboratively via user control through separate control devices, which may include a command console with haptic devices, joystick, or customized pendants.

Mechanical Arms.

The proximal end of arm 102 may be fixedly mounted or coupled to the cart 101. Mechanical arm 102 comprises a plurality of linkages 110, connected by at least one joint per arm, such as joints 111. If mechanical arm 102 is robotic, joints 111 may comprise one or more actuators in order to affect movement in at least one degree of freedom. The arm 102, as a whole, preferably has more than three degrees of freedom. Through a combination of wires and circuits, each arm may also convey both power and control signals from system cart 101 to the instruments located at the end of their extremities.

In some embodiments, the arms may be fixedly coupled to the operating table with the patient. In some embodiments, the arms may be coupled to the base of the operating table and reach around to access patient.

In some embodiments, the mechanical arms may not be robotic ally-driven. In those embodiments, the mechanical arms are comprised of linkages and set up joints that use a combination of brakes and counter-balances to hold the position of the arms in place. In some embodiments, counter-balances may be constructed from gas springs or coil springs. Brakes, such as fail safe brakes, may be mechanical or electro-mechanical. In some embodiments, the arms may be gravity-assisted passive support arms.

Distally, each arm may be coupled to an Instrument Device Manipulator (IDM), such as 117, through a Mechanism Changer Interface (MCI), such as 116. In the preferred embodiment, the MCI 116 may contain connectors to pass pneumatic pressure, electrical power, electrical signals, and optical signals from the arm to the IDM 117. In some embodiments, MCI 116 may be as simple as a set screw or base plate connection.

IDM 117 may have a variety of means for manipulating a surgical instrument including, direct drive, harmonic drive, geared drives, belts and pulleys, or magnetic drives. One skilled in the art would appreciate that a variety of methods may be used control actuators on instrument devices.

In some embodiments, the IDM may be removable. Within the robotic system, the MCIs, such as 116, may be interchangeable with a variety of procedure-specific IDMs, such as 117. In this embodiment, the interchangeability of the IDMs allows robotic system 100 to perform different procedures.

Preferred embodiments may use a robotic arm with joint level torque sensing having a wrist at the distal end, such as Kuka AG's LBR5. These embodiments have a robotic arm with seven joints, with redundant joints provided to avoid potential arm collision with a patient, other robot arms, operating table, medical personal or equipment proximate to the operative field, while maintaining the wrist at the same pose so as not to interrupt an ongoing procedure. The skilled artisan will appreciate that a robotic arm with at least three degrees of freedom, and more preferably six or more degrees of freedom, will fall within the inventive concepts described herein, and further appreciate that more than one arm may be provided with additional modules, where each arm may be commonly or separately mounted on either a cart, multiple carts, or a surgical bed or table.

Virtual Rail Configuration.

Arm 102 in system 100 may be arranged in a variety of postures for use in a variety of procedures. For example, in combination with another robotic system with at least one robotic arm, the arm 102 of system 100 may be arranged to align distally-mounted IDMs to form a "virtual rail" that facilitates the insertion and manipulation of an endoscopic tool 118. For other procedures, the arms may be arranged differently. Thus, the use of arms in system 100 provides flexibility not found in robotic systems whose design is directly tied to specific medical procedure. The arms of system 100 provide potentially much greater stroke and stowage. In other embodiments, where multiple arms are coupled to surgical bed/table platform, a multiplicity of virtual rail arrangements may be configured for a variety of different procedures.

FIG. 2A illustrates a robotic surgery system 200 in accordance with an embodiment of the present invention. System 200 comprises two system carts that collectively comprise first arm 202 and second arm 204 holding endoscopic tool bases 206 and 208, respectively. Tool base 206 has controllable endoscope sheath 210 operatively connected thereto. Tool base 208 has flexible endoscope leader 212 operatively connected thereto. In some embodiments, the tool bases may be coupled to arms 202 and 204 through IDMs and/or MCIs as disclosed earlier.

Arms 202 and 204 align tool bases 206 and 208 such that proximal end 216 of sheath 210 is distal of the proximal end 222 of leader 212, and such that leader 212 remains axially aligned with sheath 210 at an approximate angle of 180 degrees between the two arms, resulting in a "virtual rail" where the rail comprising of sheath 210 and leader 212 is approximately straight, or at 180 degrees. As will be described later, the virtual rail may have angles between 90-180 degrees. In one embodiment, sheath 210, with leader 212 slidingly disposed therethrough, is robotically inserted through, for example, a tracheal tube (not shown) in the mouth of and into patient 211, and ultimately into the patient's bronchial system, while continually maintaining the virtual rail during insertion and navigation. The arms may move sheath 210 and endoscope 212 axially relative to each other and in to or out of patient 211 under the control of a doctor (not shown) at a control console 203 (from FIG. 2B). In another embodiment, the sheath 210, with leader 212 slidingly disposed therethrough, may be robotically inserted through a patient's urethra and ultimately into the patient's urinary tract.

Navigation is achieved, for example, by advancing sheath 210 along with leader 212 into the patient 211, then leader 212 may be advanced beyond distal end 213 of the sheath, and the sheath 210 may then be brought even with the leader 212, until a desired destination is reached. Other modes of navigation may be used, such as and not by way of limitation using a guidewire through the working channel of the leader 212. The physician may be using any number of visual guidance modalities or combination thereof to aid navigation and performing the medical procedure, e.g., fluoroscopy, video, CT, MR etc. Moreover, in some embodiments, imaging means, such as a distal camera and lens may be mounted at the distal end of the leader 212. Distal end 220 of leader 212 may then be navigated to an operative site and tools are deployed through a longitudinally-aligned working channel within leader 212 to perform desired procedures. The virtual rail may be maintained during the navigation procedure and any subsequent operative procedures. Any number of alternative procedures that may require a tool or no tool at all can be performed using the flexible endoscope sliding through the sheath, as the skilled artisan will appreciate.

Figure 2B:
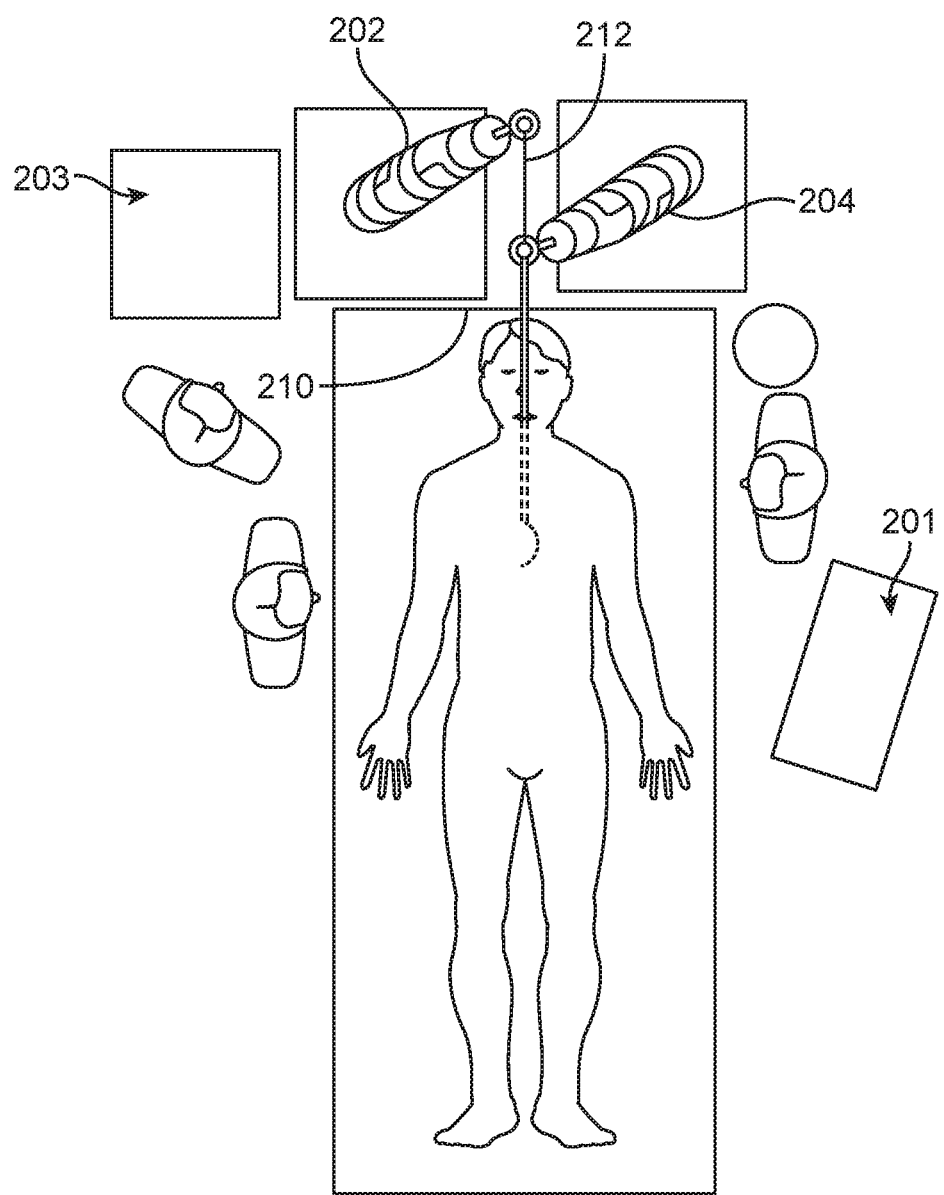
FIG. 2B illustrates an overhead view of the system of FIG. 2A, where an anesthesia cart is provided towards the head of the patient, in accordance with many embodiments.

FIG. 2B illustrates an overhead view of system 200 where anesthesia cart 201 is provided towards the head of the patient. Additionally, control console 203 with a user interface is provided to control sheath 210, endoscope leader 212, and the associated arms 202 and 204 and tool bases 206 and 208 (see FIG. 2A).

Figure 2C:
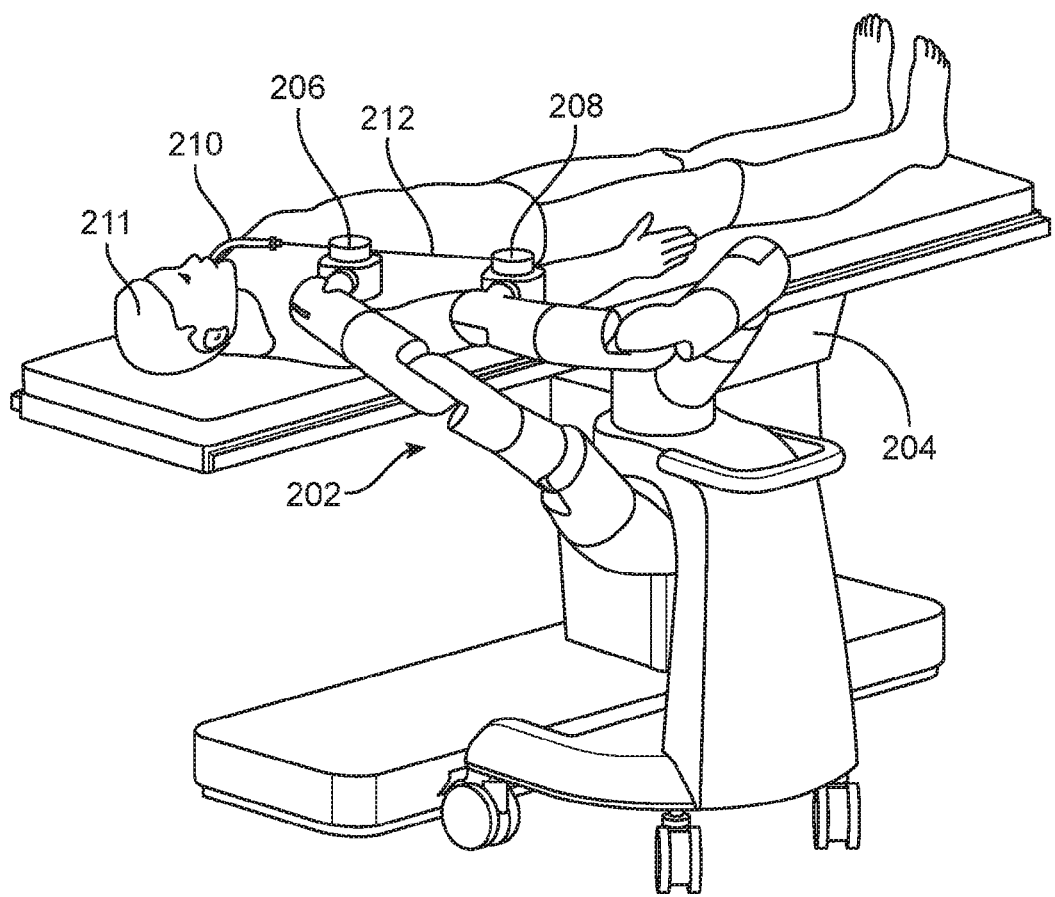
FIG. 2C shows a view of the system of FIG. 2A.

FIG. 2C shows an angled view of system 200 in FIG. 2A. Tool modules 206 and 208 with associated sheath 210 and leader 212 are attached to arms 202 and 204 and arranged in a 180 degree virtual rail. The arms are shown on a single cart, which provides added compactness and mobility. Tool bases 206 and 208 have pulley systems or other actuation systems to tension tendons in sheath 210 and leader 212 to steer their respective distal ends. Tool bases 206 and 208 may provide other desired utilities for the sheath and endoscope, such as pneumatic pressure, electrical, data communication (e.g., for vision), mechanical actuation (e.g., motor driven axels) and the like. These utilities may be provided to the tool bases through the arms, from a separate source or a combination of both.

Figure 2D:
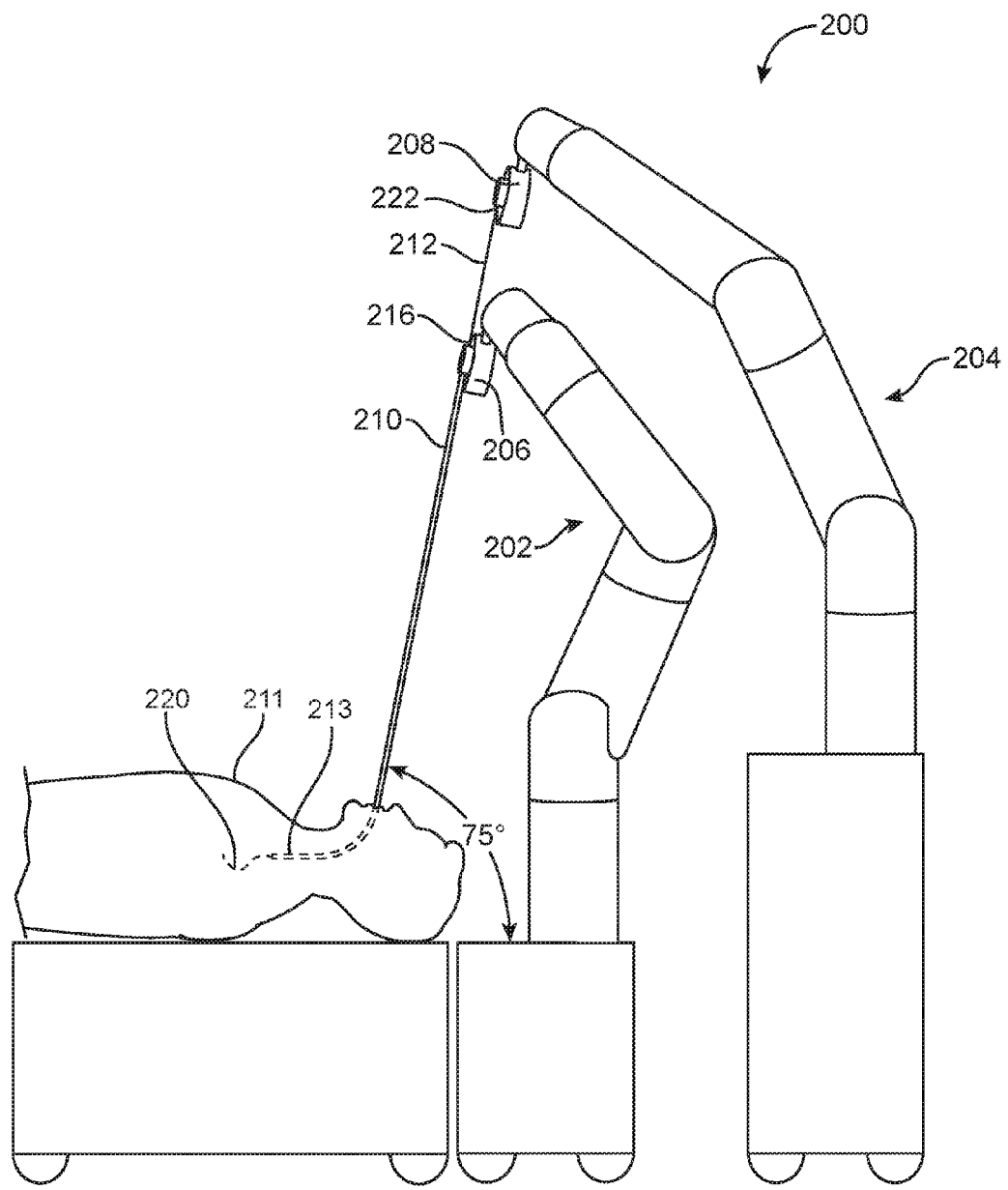
FIGS. 2D and 2E illustrate alternative arrangements of the arms 202 and 204 of the system of FIG. 2A, showing the versatility of the robotic surgical system of FIG. 2A, in accordance with many embodiments.
Figure 2E:
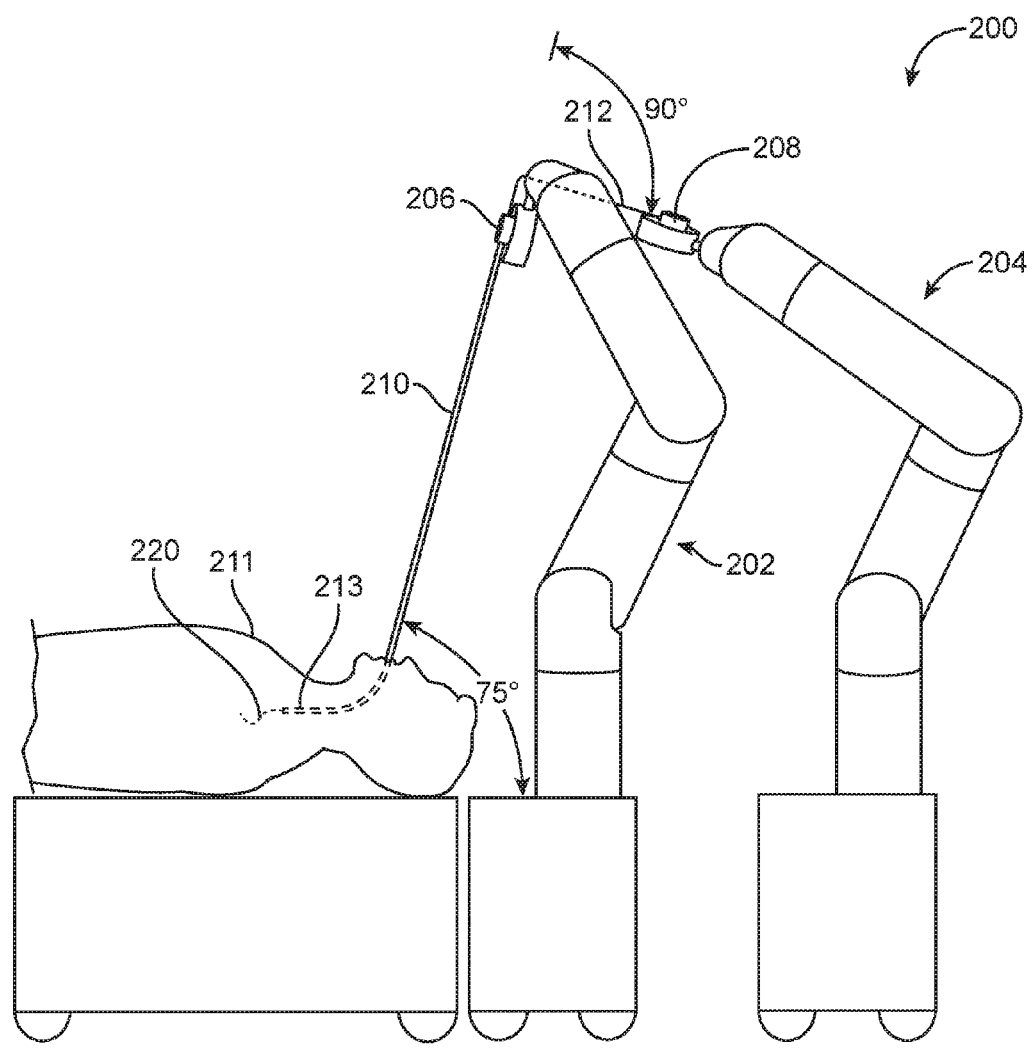

FIGS. 2D and 2E illustrate alternative arrangements of arms 202 and 204 showing the versatility of the robotic surgical system in accordance with embodiments of the present invention. In FIG. 2D, arms 202 and 204 may be extended to position the instrument (comprising sheath 210 and leader 212) to enter the mouth of patient 211 at 75 degrees from horizontal, while still maintaining a 180 degree virtual rail. This may be done during the procedure if required to accommodate space requirements within the room. The 75 degree angle was chosen for demonstrative purposes, not by way of limitation.

FIG. 2E shows an alternative arrangement of arms 202 and 204 where the tool bases 206 and 208 are aligned to create a virtual rail with a 90 degree angle, in accordance with an embodiment of the present invention. In this embodiment, the instrument (comprising sheath 210 and leader 212) enters the mouth of patient 213 at 75 degrees from horizontal. Tool bases 206 and 208 are aligned such that the leader 212 bends 90 degrees at tool base 206 prior to entering the mouth of patient 213. To facilitate the bend of leader 212, a rigid or semi-rigid patient interface, such as a tube, may be used to ensure smooth extension and retraction of the leader 212 within sheath 210. In some embodiments, an additional mechanical or robotic arm may be used to hold the patient interface in a fixed position relative to the patient.

Extension and retraction of leader 212 within sheath 210 may be controlled by moving tool base 208 either closer or farther from tool base 206 along the linear path tracked by leader 212. Extension and retraction of sheath 210 may be controlled by moving tool base 206 closer or farther from patient 213 along the linear path tracked by sheath 210. To avoid unintended extension or retraction of leader 212 while extending or retracting sheath 210, tool base 208 may also be moved along a linear path parallel to sheath 210.

Virtual rails are useful in driving both rigid instrument and flexible instruments, and especially where there are telescoping requirements. The use of a virtual rail is not limited to a single rail but can consist of multiple virtual rails where the arms act in concert to maintain the individual virtual rails in performance of one or more procedures.

Figure 3A:
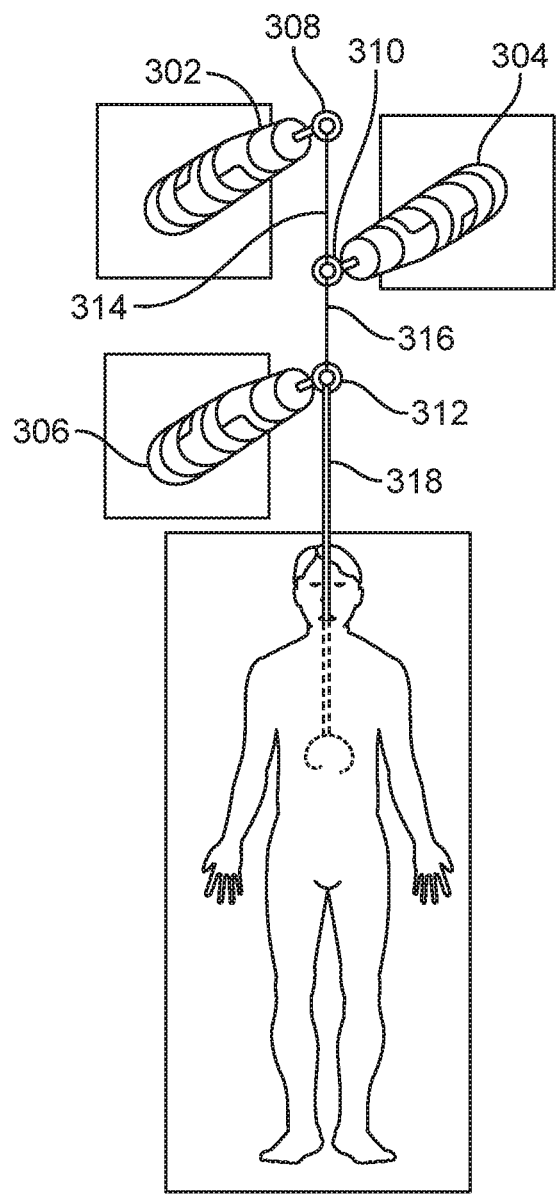
FIG. 3A illustrates an overhead view of a system with multiple virtual rails, in accordance with many embodiments.

FIG. 3A illustrates an overhead view of a system with multiple virtual rails, in accordance with an embodiment of the present invention. In FIG. 3A, robot arms 302, 304 and 306 respectively hold tool bases 308, 310, and 312. Tool bases 308 and 310 may be operatively coupled to flexible tool 314 and tool 316. Tool 314 and tool 316 may be a telerobotically-controlled flexible endoscopic instruments. Tool base 312 may be operatively coupled to a dual lumen sheath 318, where each lumen receives tools 314 and 316. Arms 302 and 304 may each maintain a virtual rail with robotic arm 306, and movements of all three arms may be coordinated to maintain virtual rails and move tools 314, 316 and sheath 318 relative to each other and the patient.

Figure 3B:
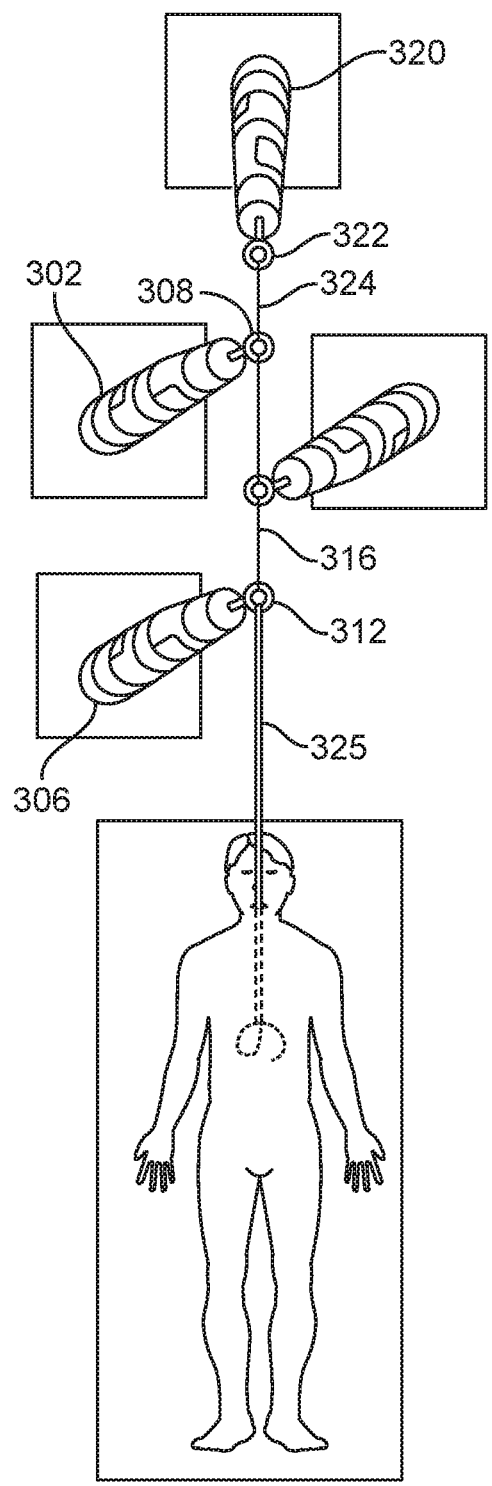
FIG. 3B illustrates the use of the robotic surgery system FIG. 3A with an additional robotic arm, associated tool base, and tool, in accordance with many embodiments.

FIG. 3B illustrates the use of the robotic surgery system from FIG. 3A with an additional robotic arm 320 and associated tool base 322 and tool 324. In this embodiment sheath 325 may have three lumens. Alternatively, sheath 325 may comprise more than one sheath to provide access to tools 314, 316, and 324. As will be appreciated, the ability to increase or reduce the number of arms with associated modules and instruments permits a great number and flexibility of surgical configurations, which, in turn, permits re-purposing of expensive arms and use of multiple relatively-inexpensive modules to achieve great versatility at reduced expense.

To create the virtual rail, a plurality of arms and/or platforms may be utilized. Each platform/arm must be registered to the others, which can be achieved by a plurality of modalities including, vision, laser, mechanical, magnetic, or rigid attachment. In one embodiment, registration may be achieved by a multi-armed device with a single base using mechanical registration. In mechanical registration, an embodiment may register arm/platform placement, position, and orientation based on their position, orientation and placement relative to the single base. In another embodiment, registration may be achieved by a system with multiple base using individual base registration and "handshaking" between multiple robot arms. In embodiments with multiple bases, registration may be achieved by touching together arms from different bases, and calculating locations, orientation and placement based on (i) the physical contact and (ii) the relative locations of those bases. In some embodiments, registration targets may be used to match the position and orientations of the arms relative to each other. Through such registration, the arms and instrument driving mechanisms may be calculated in space relative to each other. The skilled artisan will be able to use many different methods to register the robotic platforms.

System Modularity & Flexibility.

Returning to FIG. 1, robotic surgical system 100 may be configured in a manner to provide a plurality of surgical system configurations, such as by changing IDM 117 and tool 118 (also known as an end effector). The system may comprise one or more mobile robotic platforms staged at different locations in the operative room, or at a convenient nearby location. Each platform may provide some or all of power, pneumatic pressure, illumination sources, data communication cables and control electronics for a robotic arm that is coupled to the platform, and the module may draw from these utilities as well. System 100 may alternatively have multiple arms 102 mounted on one or more mobile carts 101, or the arms may be mounted to the floor in order to provide a plurality of surgical configurations.

In addition to multiple arms and platforms, certain embodiments of the present invention are designed to readily exchange between multiple modules or end effector mechanisms. Various surgical procedures or steps within a procedure may require the use of different modules and the associated instrument sets, for example, exchanging between different sized sheath and endoscope combinations. The interchangeability allows the system to reconfigure for different clinical procedures or adjustments to surgical approaches.

Figure 4A:
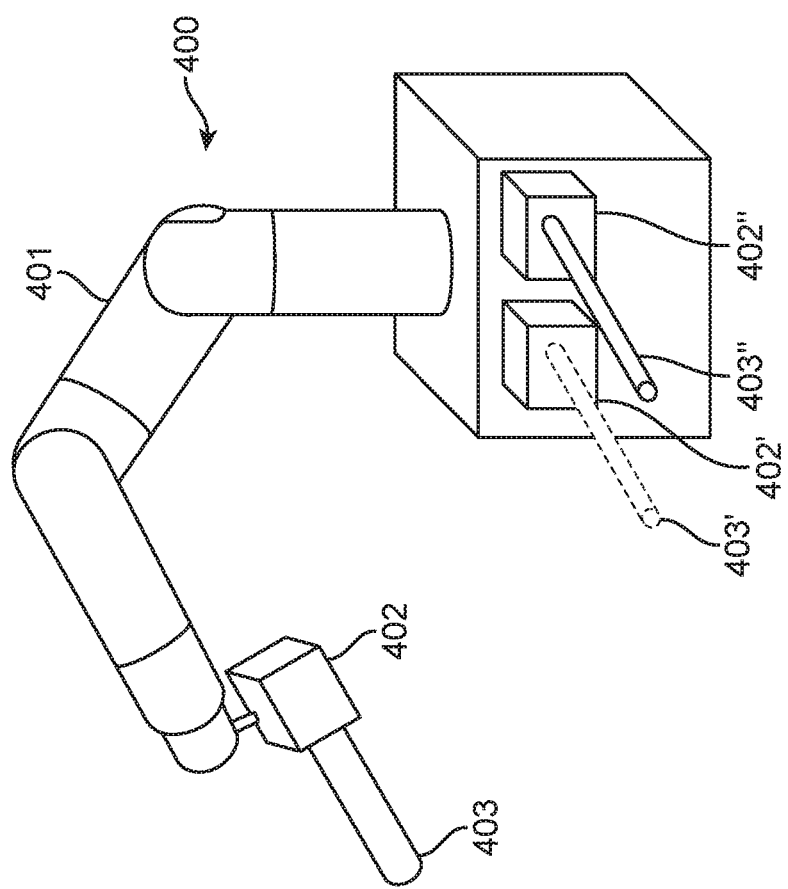
FIGS. 4A and 4B illustrate the modularity of embodiments of the present invention.

FIG. 4A illustrates an embodiment compatible with interchangeable modules and instruments. Surgical system 400, like those shown and described previously, has one or more robotic arms 401 to which IDM or module 402 with tool or instrument 403 is attached. Modules 402' and 402", and associated instruments 403' and 403", can be exchanged onto robotic arm 401 or picked up by a different robotic arm (not shown) to be used alone in concert with another module. Each module is a dedicated electromechanical system which is used to drive various types of instruments for specified procedures. To drive instruments, each IDM or module may comprise an independent drive system, which may include a motor. They may contain sensors (e.g., RFID) or memory chips that record their calibration and application related information. A system calibration check may be required after a new mechanism is connected to the robot arm. In some embodiments, a module may control an associated sheath, catheter leader, or flexible endoscope.

In FIG. 4A, system 400 may exchange IDM 402 for IDMs 402' and 402" by itself through the use of global registration and sensors. In some embodiments, IDMs 402" and 403" are stored on system cart 404 at predetermined "docking stations" which are configured with identification and proximity sensors. Sensors at these stations may make use of technologies such as RFID, optical scanners (e.g., bar codes), EEPROMs, and physical proximity sensors to register and identify which IDMs are "docked" at the docking station. As robotic arm 401 and the IDM docking stations reside on system cart 404, the identification and proximity sensors allow the IDMs that are resting in the docking stations to be registered relative to the robotic arm(s). Similarly, in embodiments with multiple arms on a single system cart, multiple arms may access the IDMs on the docking station using the combination of registration system and sensors discussed above.

Figure 4B:
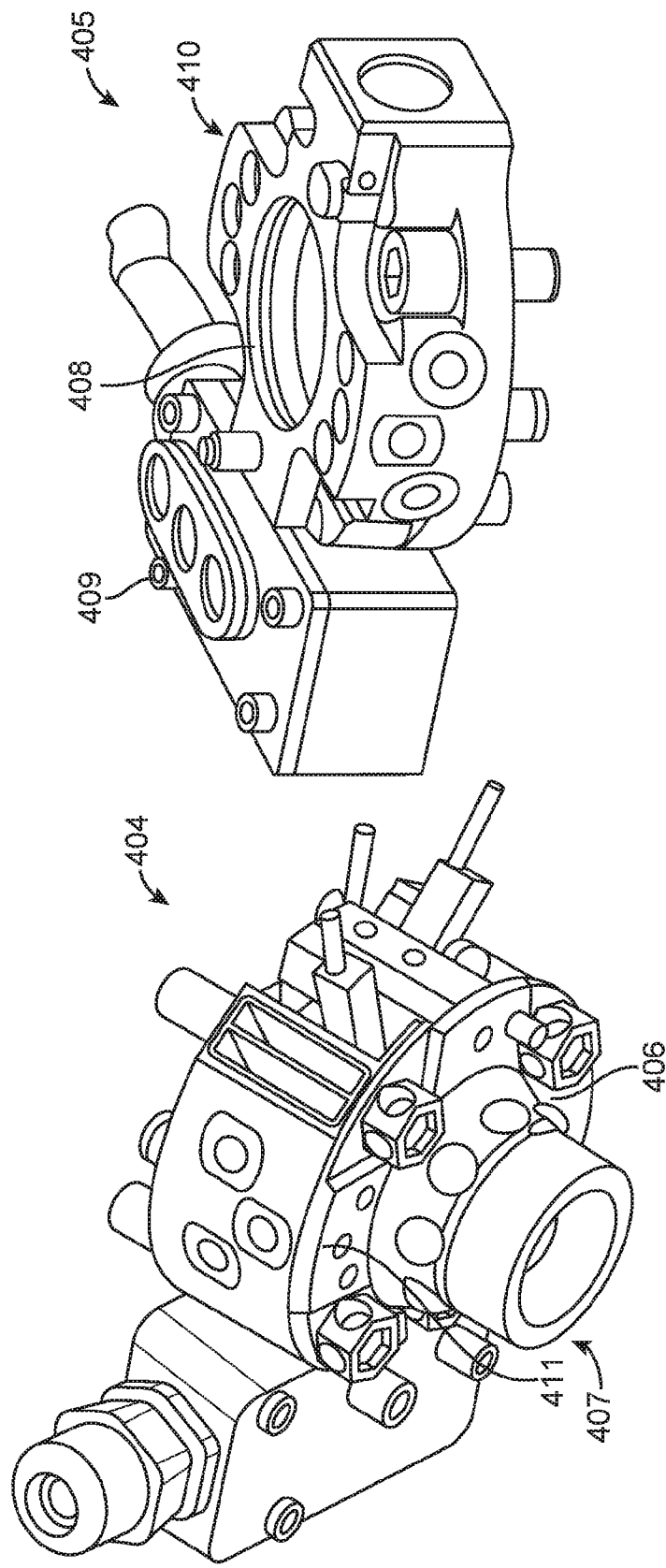

FIG. 4B shows two different perspectives on exchange mechanisms 404 and 405 that may be used to exchange and attach modules 402 to robotic arm 401. Exchange mechanisms 404 and 405 provide the connection between a module, such as module 402 in FIG. 4A, and a robotic arm, such as robotic arm 401 in FIG. 4A. In some embodiments, the mechanism 404 may be the interface on a module, such as an instrument driving mechanism, for connection to mechanism 405, which may be the interface on a robotic arm. Mechanism 404 may provide a mechanism interface 411 for connecting flange 407 into ring 408 of mechanism 405. Similarly, the interface may provide for transmitting power (409), fiber optics, data connections, pneumatic connections (410, 411), motors to drive pulley systems to control a tool, such as a sheath and flexible endoscope. As described for the sheath and flexible endoscope embodiment, the sheath and flexible endoscope would be operatively coupled to the exchange mechanism.

Figure 5A:
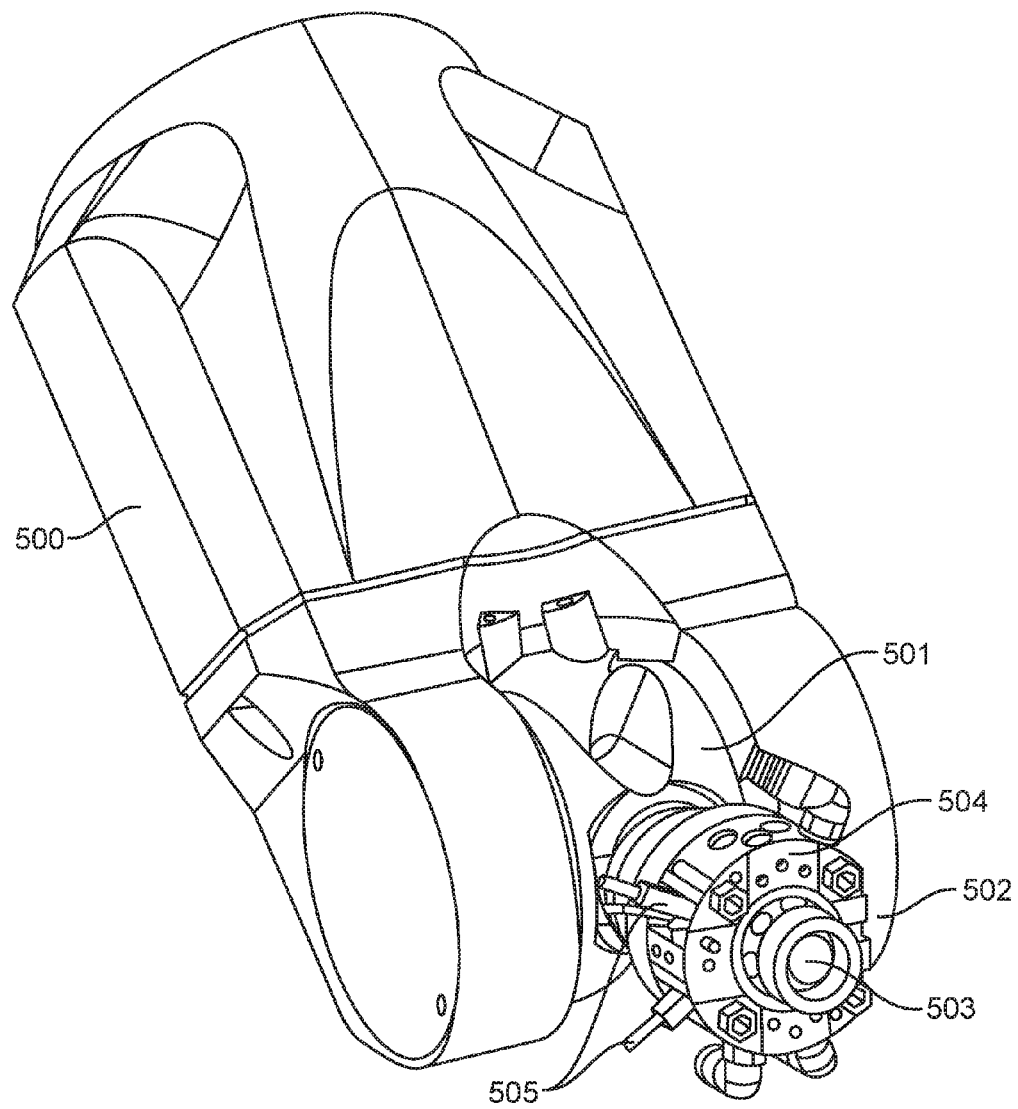
FIG. 5A illustrates an implementation of a mechanism changer interface coupled to a mechanical arm in a robotic system, in accordance with an embodiment of the present invention.

FIGS. 5A-5D illustrate a mechanism changer interface in a robotic system, in accordance with an embodiment of the present invention. FIG. 5A specifically illustrates an implementation of a mechanism changer interface coupled to a robotic arm in a robotic system, in accordance with an embodiment of the present invention. As shown in FIG. 5A, the distal portion of robotic arm 500 comprises an articulating joint 501 coupled to a "male" mechanism changer interface 502. Articulating joint 501 provides an additional degree of freedom with respect to manipulating an instrument device mechanism (not shown) that is configured to couple to robotic arm 500. Male mechanism changer interface 502 provides a male connector interface 503 that provides a strong, physical connection to the reciprocal female receptacle connector interface on the IDM (not shown). The spherical indentations on the male connector interface 503 physically couple to reciprocal indentations on the female receptacle interface on the IDM. The spherical indentations may be extended when pneumatic pressure is conveyed along robotic arm 500 into male mechanism changer interface 502. The male mechanism changer interface 502 also provides connections 504 for transferring for pneumatic pressure to the IDM. Additionally, this embodiment of the mechanism changer interface provides for alignment sensors 505 that ensure that the male mechanism changer interface 502 and its reciprocal female interface are properly aligned.

Figure 5B:
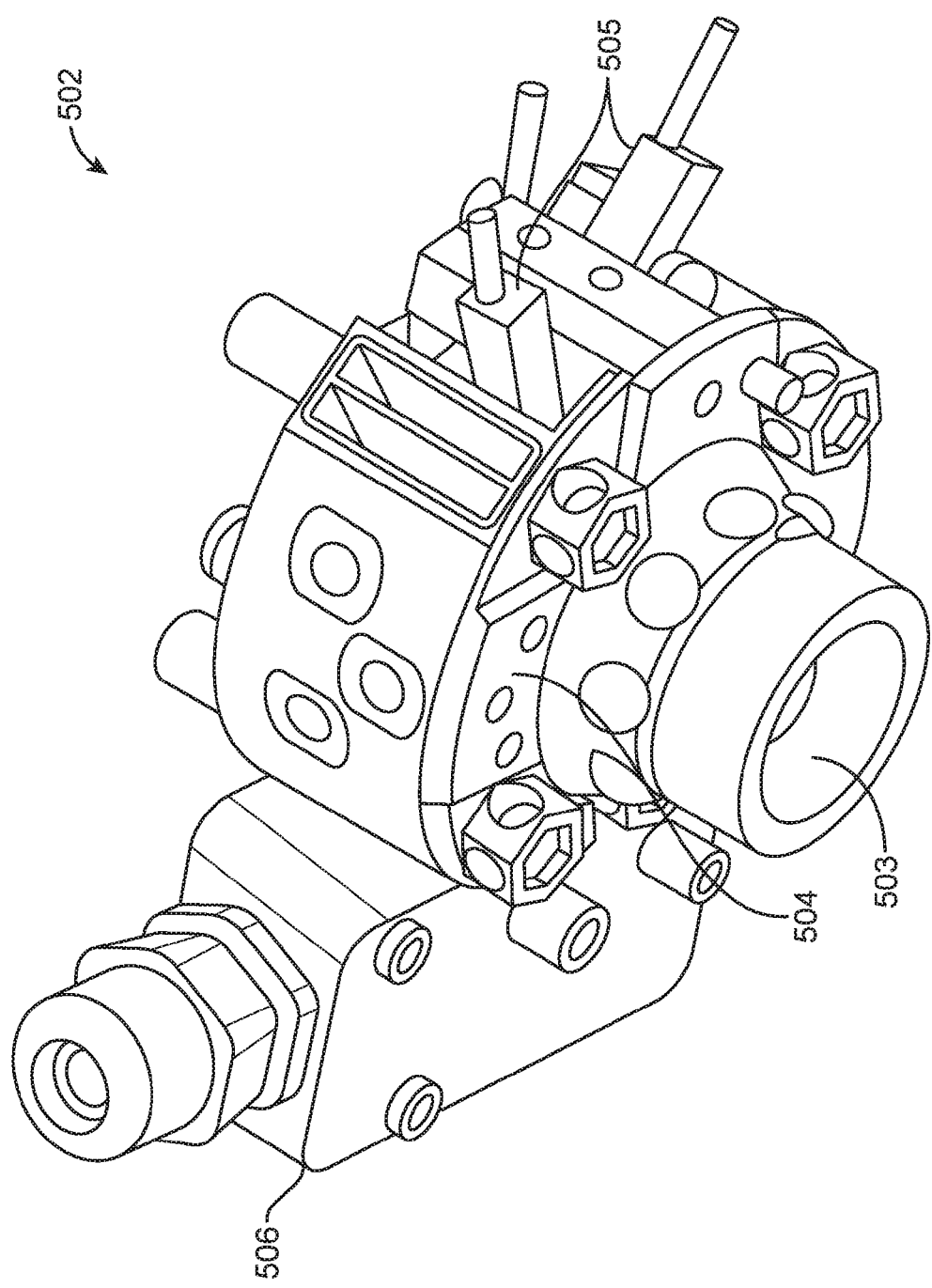
FIG. 5B illustrates an alternative view of male mechanism changer interface 502 from FIG. 5A.

FIG. 5B illustrates an alternative view of male mechanism changer interface 502 separated from robotic arm 500. As discussed with respect to FIG. 5A, male mechanism changer interface 502 provides for a flange-like male connector interface 503, pneumatic connectors 504, and alignment sensors 505. Additionally, an electrical interface 506 for connecting electrical signals to the reciprocal interface on the IDM (not shown).

Figure 5C:
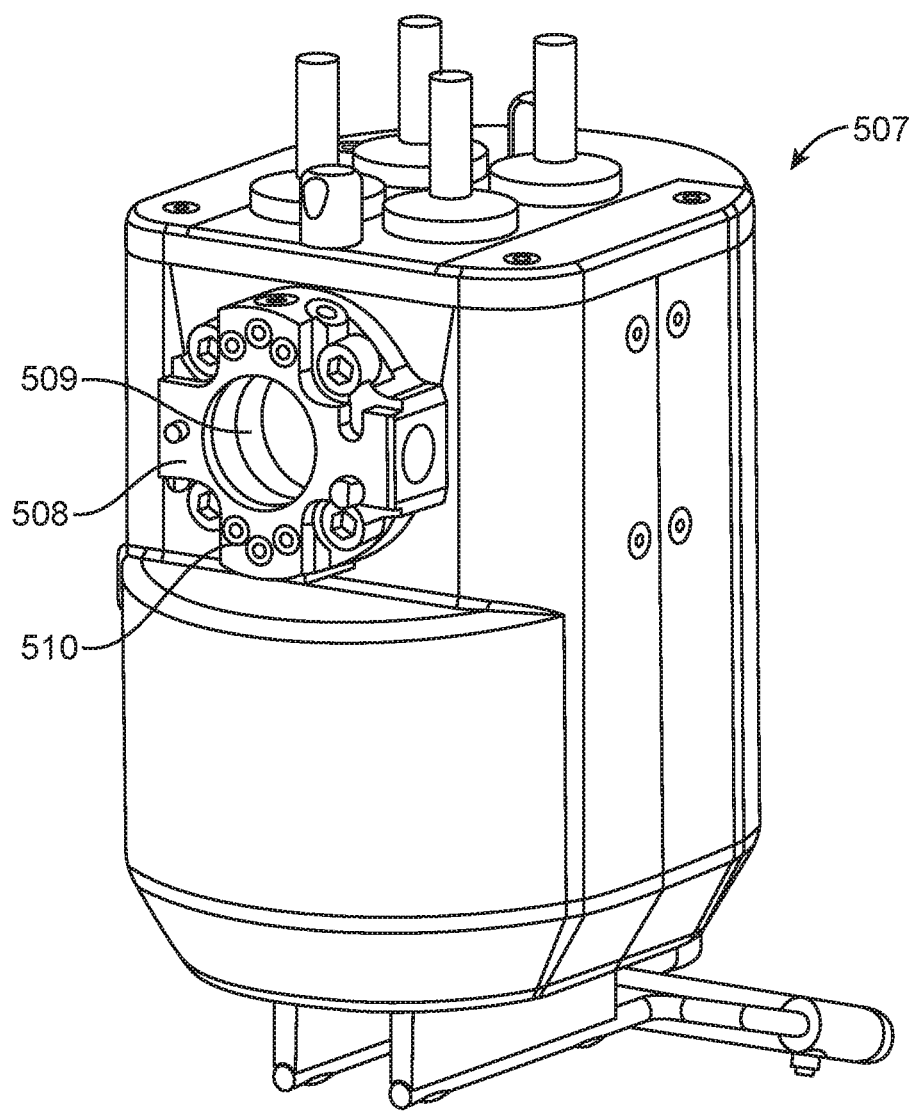
FIG. 5C illustrates a reciprocal female mechanism changer interface coupled to an instrument device manipulator for connecting with male mechanism changer interface 502 from FIGS. 5A and 5B.

FIG. 5C illustrates a reciprocal female mechanism changer interface coupled to an instrument device manipulator for connecting with male mechanism changer interface 502 from FIGS. 5A and 5B. As shown in FIG. 5C, instrument device manipulator 507 is coupled to a female mechanism changer interface 508 that is configured to connect to male mechanism changer interface 502 on robotic arm 500. Female mechanism changer interface 508 provides for female receptacle interface 509 that is designed to couple to the flange-like male connector interface 503 of male mechanism changer interface 502. The female receptacle interface 509 also provides a groove to grip the spherical indentations on the male connector interface 503. When pneumatic pressure is applied, spherical indentations on male connector 503 are extended, and male connector 503 and receptacle interfaces 509 securely couple the IDM 507 to the robotic arm 500. Reciprocal female mechanism changer interface 508 also provides with pneumatic connectors 510 to accept the pneumatic pressure conveyed from connectors 504.

Figure 5D:
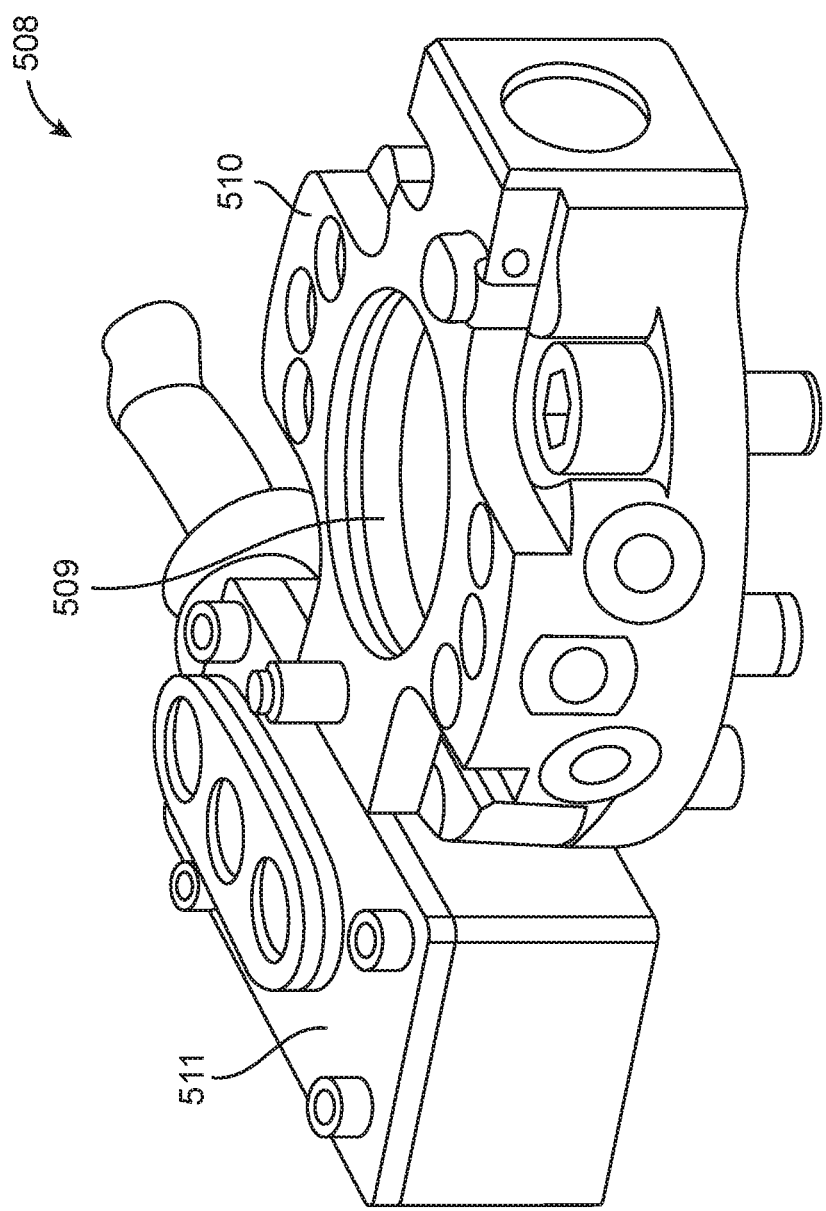
FIG. 5D illustrates an alternative view of a female mechanism changer interface 508 from FIG. 5C.

FIG. 5D illustrates an alternative view of female mechanism changer interface 508 from FIG. 5C. As discussed earlier, reciprocal mechanism changer interface 508 contains a receptacle interface 509, pneumatic connectors 510 for interfacing with mechanism changer interface 502 on robotic arm 500. In addition, mechanism changer interface 508 also provides for an electrical module 511 for transmitting electrical signals—power, controls, sensors—to module 506 in mechanism changer interface 502.

Figure 6:
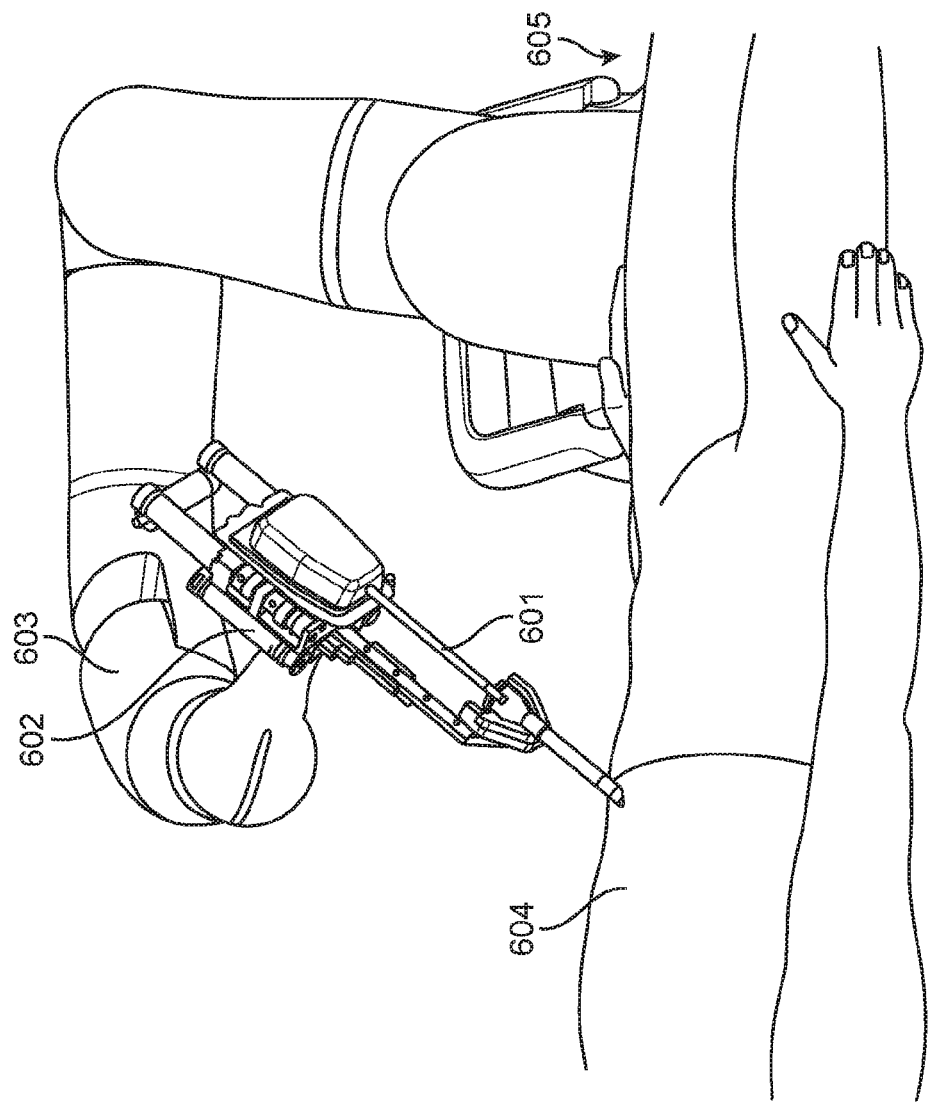
FIGS. 6, 7, 8A, and 8B illustrate alternative embodiments of modules for a robotic surgical system of the present invention.

FIGS. 6-9B illustrate additional, interchangeable modules that may be operated using system 400 from FIG. 4. FIG. 6 illustrates an embodiment of the present invention that uses a single port laparoscopic instrument 601 connected through an instrument interface 602 on a single robotic arm 603 that is directed at the abdomen 604 of a patient 605.

Figure 7:
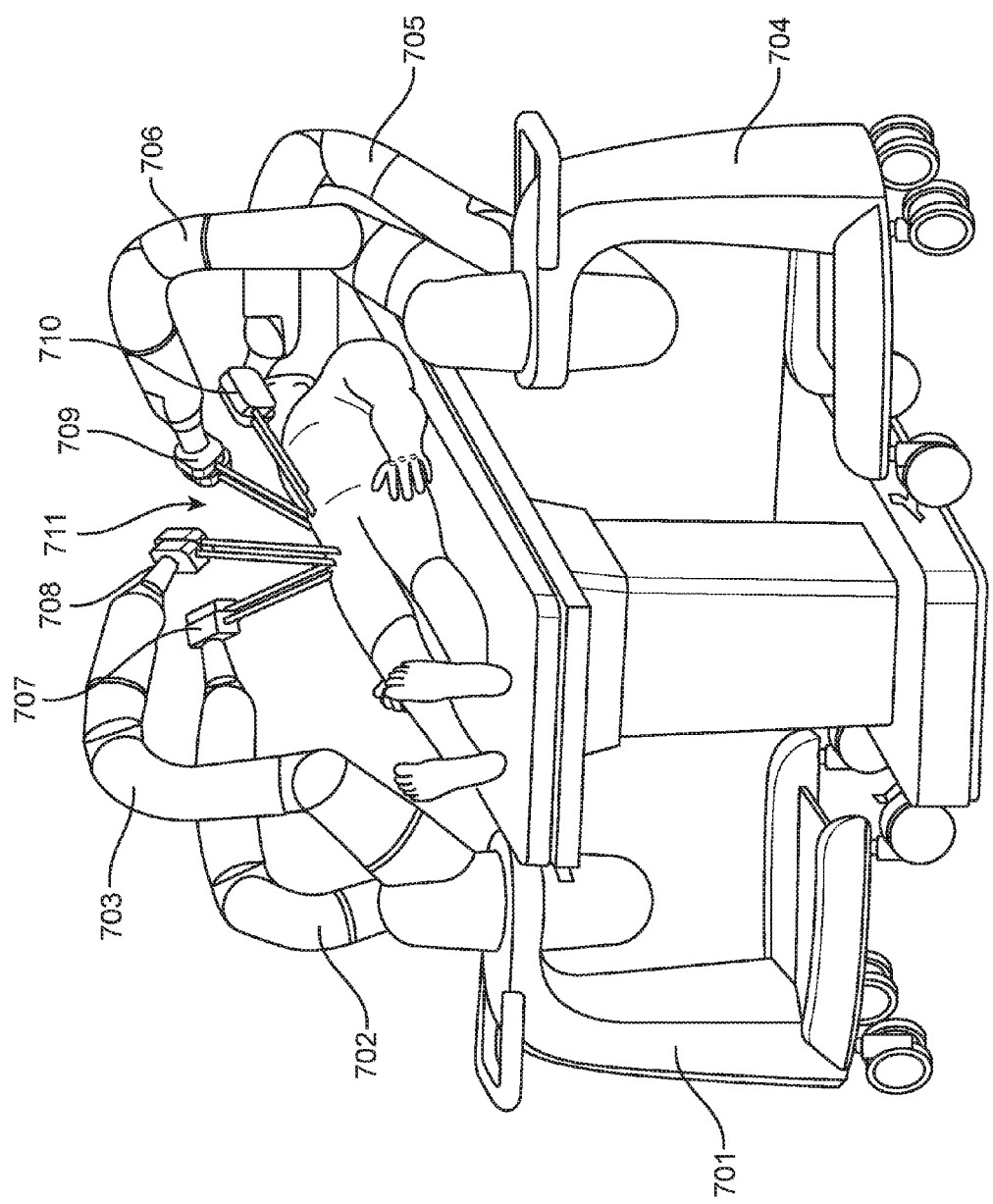

FIG. 7 illustrates an embodiment of the present invention with two sets of robotic subsystems 701 and 704, each with a pair of robotic arms 702, 703 and 705, 706 respectively. Connected through instrument interfaces at the distal end of each robotic arm are laparoscopic instruments 707, 708, 709, 710, respectively, all instruments working together to perform the procedures in an individual patient 711.

Figure 8A:
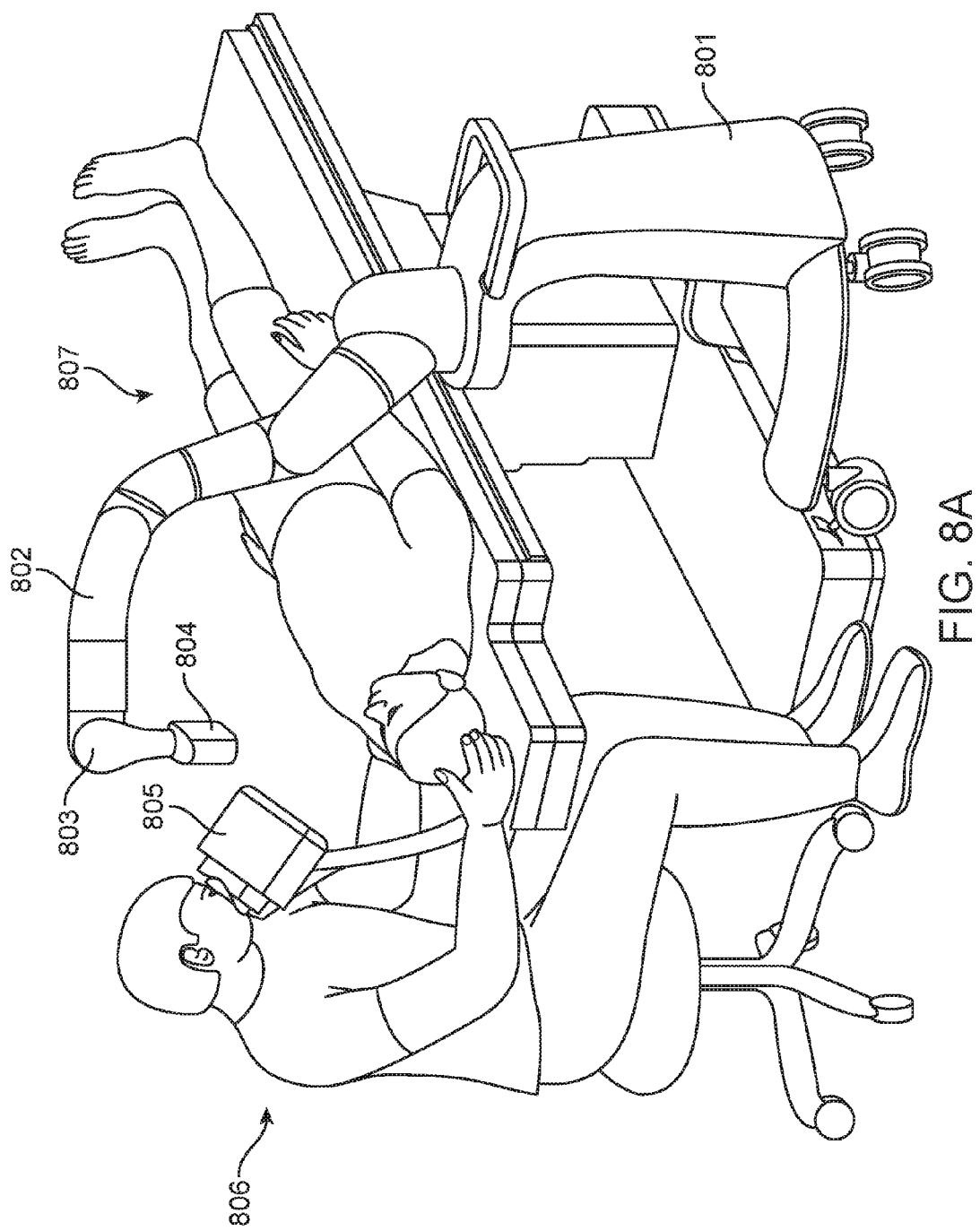

FIG. 8A illustrates an embodiment of the present invention with a subsystem 801 with a single robotic arm 802, where a microscope tool 804 connected to the robotic arm 802 through an instrument interface 803. In some embodiments, the microscopic tool 804 may be used in conjunction with a second microscope tool 805 used by a physician 806 to aid in visualizing the operational area of a patient 807.

Figure 8B:
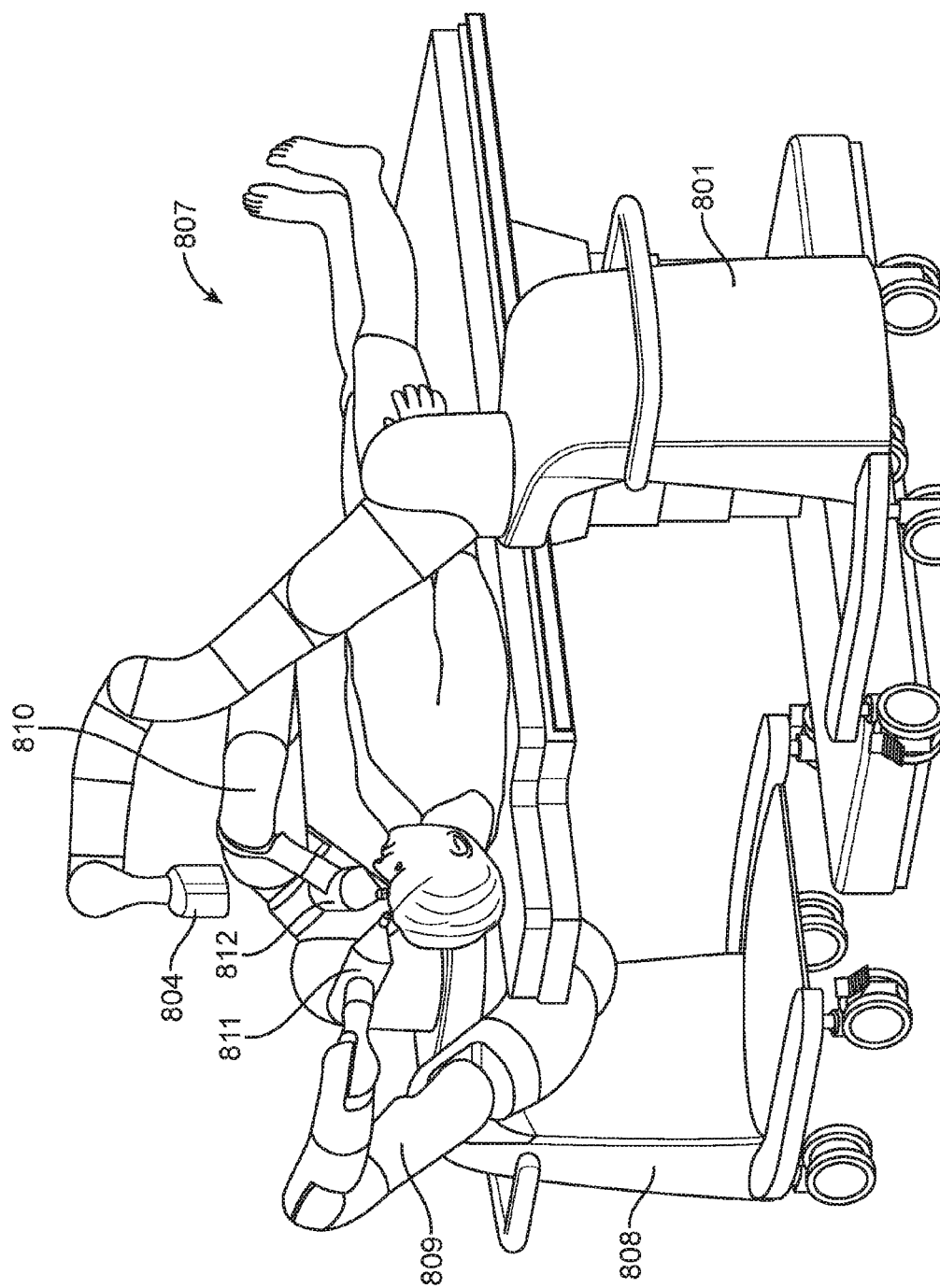

FIG. 8B illustrates an embodiment of the present invention where subsystem 801 from FIG. 8A may be used in conjunction with subsystem 808 to perform microsurgery. Subsystem 808 provides robotic arms 809 and 810, each with microsurgical tools 811 and 812 connected through instrument interfaces on each respective arm. In some embodiments, the one or more robotic arms can pick up and exchange tools at a table or other suitable holding mechanism within reach of the robotic arm, such as a docking station. In FIG. 8A, shows the interchangeable modules are stored on the side of the cart on which the robotic arm is mounted.

Robotic Catheter Design.

In a preferred embodiment, robotic system 100 from FIG. 1 may drive a tool customized for various surgical procedures, such as robotic catheter 118. FIG. 9 is an illustration of a robotic catheter that may be used in conjunction with a robotic system 100 from FIG. 1, in accordance with an embodiment of the present invention. Robotic catheter 900 may be arranged around nested longitudinally-aligned tubular bodies, referred to as a "sheath" and a "leader". The sheath 901, the tubular tool with the larger outer diameter, may be comprised of a proximal sheath section 902, a distal sheath section 903, and a central sheath lumen (not shown). Through signals received in the sheath base 904, the distal sheath portion 903 may be articulated in the operator's desired direction. Nested within the sheath 901 may be a leader 905 with a smaller outer diameter. The leader 905 may comprise a proximal leader section 906 and a distal leader section 907, and a central working channel. Similar to sheath base 904, leader base 908 controls articulation of the distal leader section 907 based on control signals communicated to leader base 908, often from the IDMs (e.g., 117 from FIG. 1).

Both the sheath base 904 and leader base 908 may have similar drive mechanisms, to which control tendons within sheath 901 and leader 905 are anchored. For example, manipulation of the sheath base 904 may place tensile loads on tendons in the sheath 901, therein causing deflection of distal sheath section 903 in a controlled manner. Similarly, manipulation of the leader base 908 may place tensile loads on the tendons in leader 905 to cause deflection of distal leader section 907. Both the sheath base 904 and leader base 908 may also contains couplings for the routing of pneumatic pressure, electrical power, electrical signals or optical signals from the IDMs to the sheath 901 and leader 904.

Control tendons within the sheath 901 and leader 905 may be routed through the articulation section to an anchor positioned distal to the articulation section. In a preferred embodiment, the tendons within sheath 901 and leader 905 may consist of a stainless steel control tendon routed through a stainless steel coil, such as a coil pipe. One skilled in the arts would appreciate that other materials may be used for the tendons, such as Kevlar, Tungsten and Carbon Fiber. Placing loads on these tendons causes the distal sections of sheath 901 and leader 905 to deflect in a controllable manner. The inclusion of coil pipes along the length of the tendons within the sheath 901 and leader 905 may transfer the axial compression back to the origin of the load.

Using a plurality of tendons, the robotic catheter 900 has the ability to navigate lumens within the human body with ease by providing a plurality of degrees of freedom (each corresponding to an individual tendon) control at two points—distal sheath section 903 and distal leader section 907—along its length. In some embodiments, up to four tendons may be used in either the sheath 901 and/or leader 905, providing up to eight degrees of freedom combined. In other embodiments, up to three tendons may be used, providing up to six degrees of freedom.

In some embodiments, the sheath 901 and leader 905 may be rolled 360 degrees, providing for even more tool flexibility. The combination of roll angles, multiple degrees of articulation, and multiple articulation points provides the surgeon with a significant improvement to the instinctive control of the device as it navigates a tortuous path within the human body.

Sheath and Endoscope Structure.

Figure 10A:
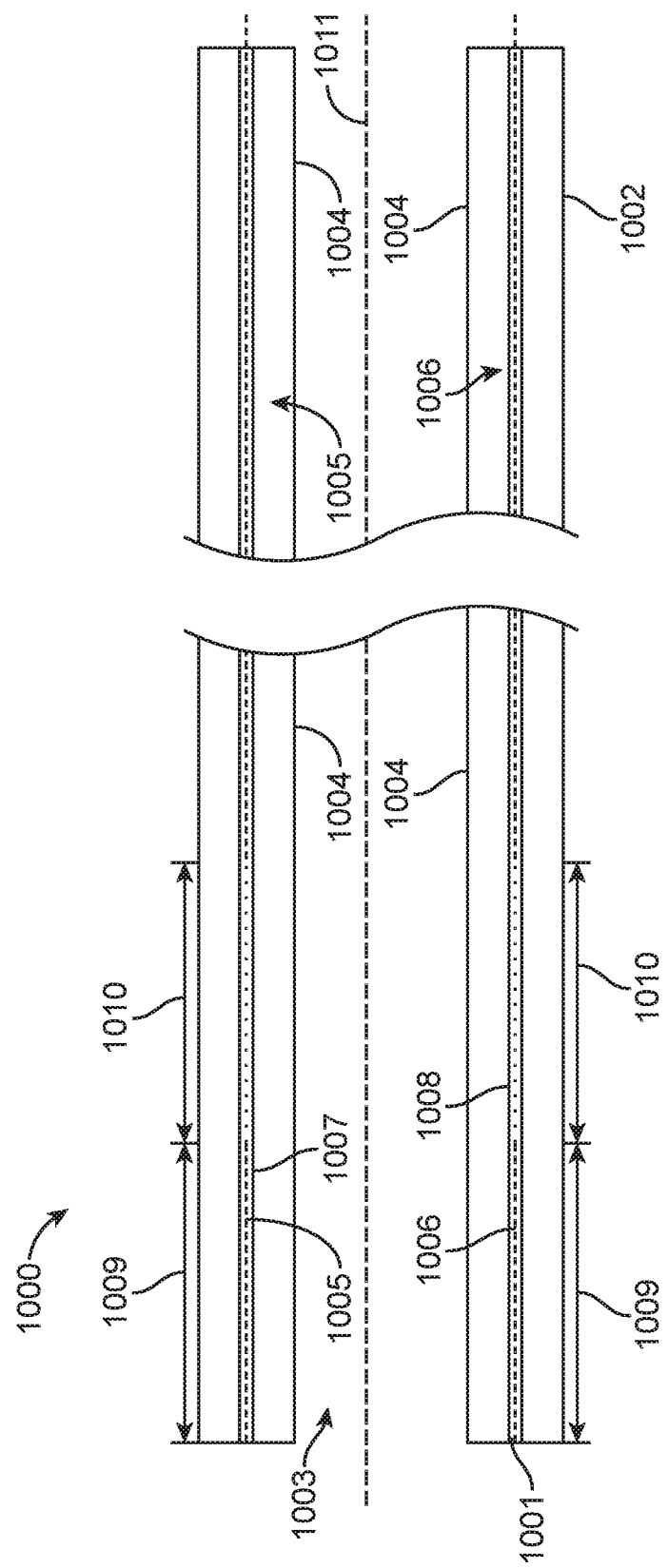
FIGS. 10A, 10B, and 10C illustrate the structure of a sheath of a flexible endoscopic device, in accordance with an embodiment of the present invention.

FIGS. 10A, 10B, 10C, 11A, and 11B provide details of a sheath (similar to that of sheath 210 described above) and a flexible endoscope (similar to that of flexible endoscope 212 described above) in accordance with an embodiment of the present invention. FIG. 10A shows sheath 1000 with distal end 1001 and proximal end 1002 and lumen 1003 running between the two ends. Lumen 1003 is preferably sized to slidingly receive a flexible endoscope (such as endoscope 1100 from FIGS. 11A and 11B). Sheath 1000 has walls 1004 with tendons 1005 and 1006 running inside the length of walls 1004 of sheath 1000. Tendons 1005 and 1006 slidingly pass through conduits 1007 and 1008 in walls 1004 and terminate at distal end 1001. In some embodiments, the tendons may be formed from steel. Appropriate tensioning of tendon 1005 compresses distal end 1001 towards conduit 1007, while minimizing bending of the helixed section 1010. Similarly, appropriate tensioning of tendon 1006 compresses distal end 1001 towards conduit 1008. In some embodiments, lumen 1003 may not be concentric with sheath 1000.

Tendons 1005 and 1006 and associated conduits 1007 and 1008 from sheath 1000 from FIG. 10A preferably do not run straight down the length of sheath 1000, but helix along a helixed section 1010 and then run longitudinally straight (i.e., approximately parallel to the neutral axis) along distal section 1009. It will be appreciated that helixed section 1010 may begin from the proximal end of distal section 1009 extending proximally down sheath 1010 and may terminate at any desired length for any desired or variable pitch. The length and pitch of helixed section 1010 is determined based on the desired properties of sheath 1000, taking into account desired flexibility of the shaft, and increased friction in the helixed section 1010. Tendons 1005 and 1006 run approximately parallel to central axis 1011 of sheath 1000 when not in the helixed section, such as the proximal section of the endoscope 1000.

In some embodiments, the tendon conduits may be at ninety degrees to each other (e.g., 3-, 6-, 9- and 12-o'clock). In some embodiments, the tendons may be spaced one hundred and twenty degrees from each other, e.g., three total tendons. In some embodiments, the tendons may be not be equally spaced. In some embodiments, they may be all to one side of the central lumen. In some embodiments, the tendon count may differ from three or four.

Figure 10B:
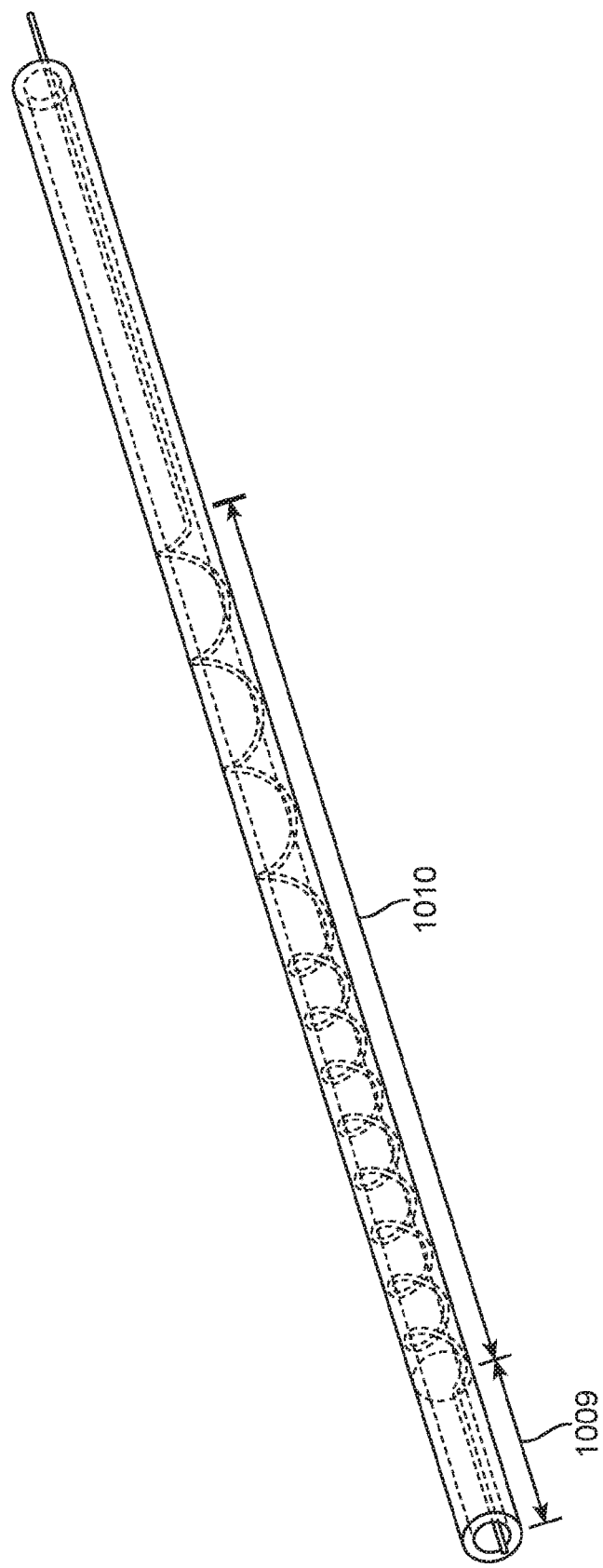
Figure 10C:
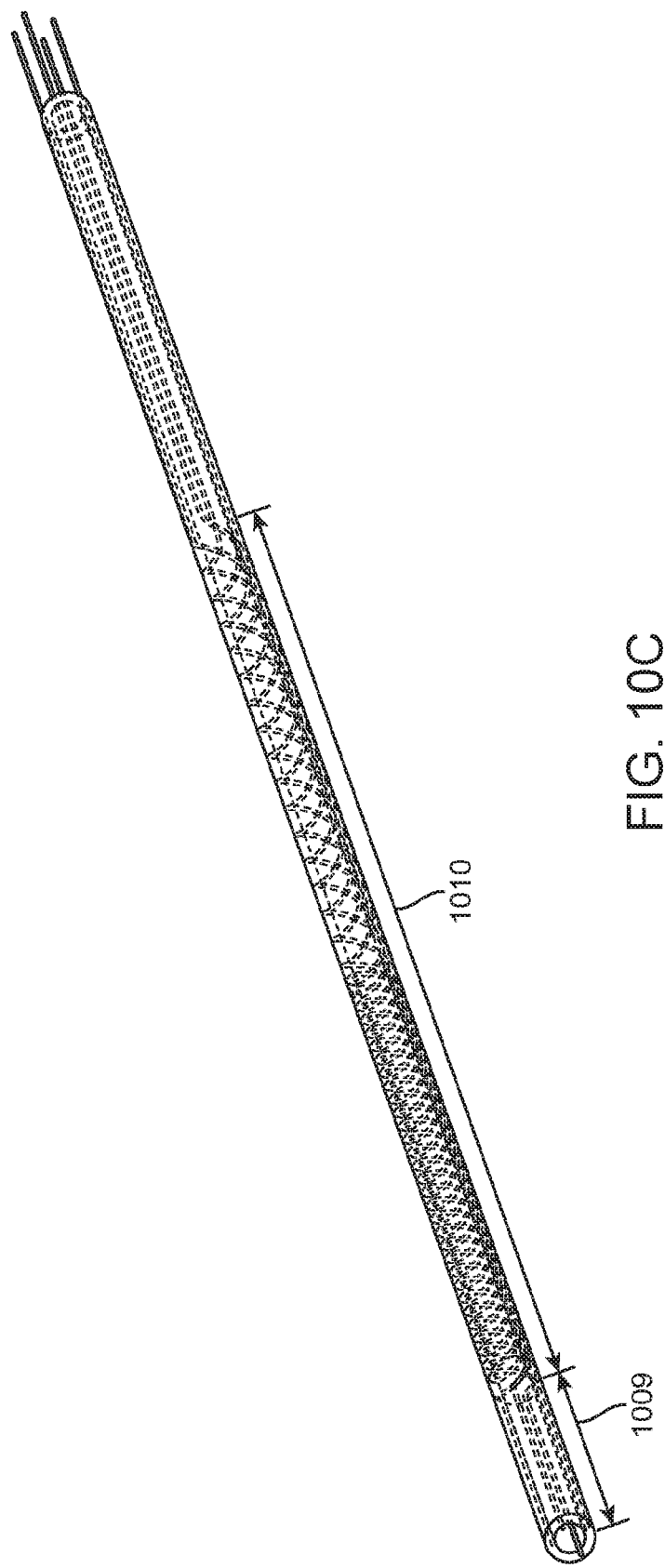

FIG. 10B shows a three-dimensional illustration of an embodiment of sheath 1000 with only one tendon for the purpose of clarifying the distinction between non-helixed section 1009 and a variable pitch helixed section 1010. While one tendon may be used, it is preferred to use multiple tendons. FIG. 10C shows a three-dimensional illustration of an embodiment of sheath 1000 with four tendons extending along distal section 1009, helixed section 1010 and then proximal to helixed section 1010.

Figure 11A:
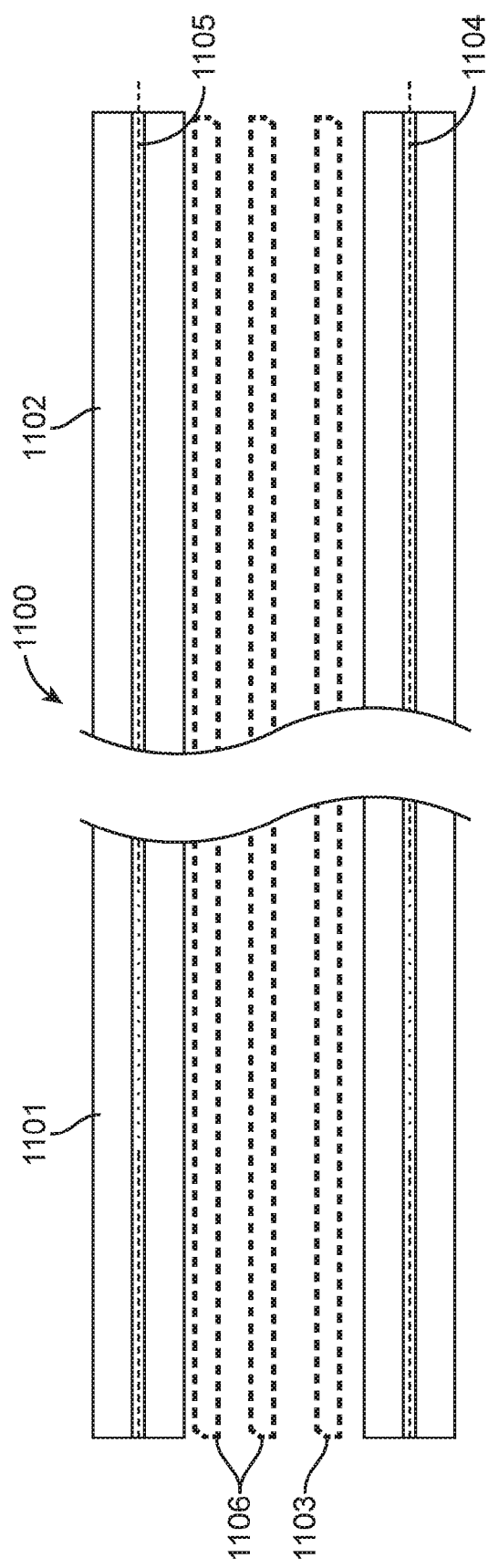
FIGS. 11A and 11B illustrate the structure of a flexible endoscopic device in accordance with an embodiment of the present invention.

FIG. 11A shows a flexible endoscope 1100 with distal end 1101 and proximal end 1102, that may be sized to slidingly reside within the sheath 1000 from FIGS. 10A-10C. Endoscope 1100 may include at least one working channel 1103 passing through it. Proximal end 1002 of sheath 1000 and proximal end 1102 of flexible endoscope 1100 are, respectively, operatively connected to modules 206 and 208 from FIG. 2 respectively. Tendons 1104 and 1105 slidingly pass through conduits 1106 and 1107 respectively in walls 1108 and terminate at distal end 1101.

Figure 11B:
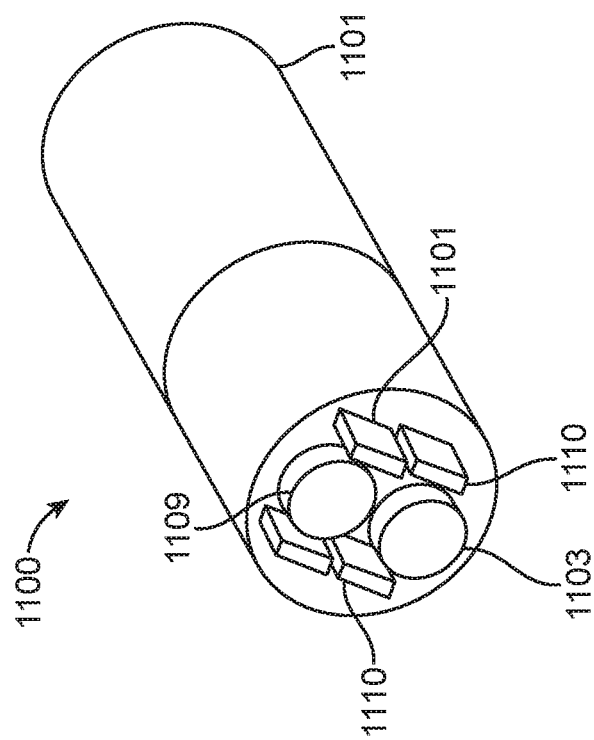

FIG. 11B shows the distal end 1101 of flexible endoscope 1100, an exemplary embodiment, that has imaging 1109 (e.g., CCD or CMOS camera, terminal end of imaging fiber bundle etc.), light sources 1110 (e.g., LED, optic fiber etc.) and may include at least one working channel opening 1103. Other channels or operating electronics 1106 may be provided along flexible endoscope 1100 to provide various known capabilities at the distal end, such as wiring to camera, insufflation, suction, electricity, fiber optics, ultrasound transducer, EM sensing, and OCT sensing.

In some embodiments, the distal end 1101 of endoscope 1100 may include a "pocket" for insertion of a tool, such as those disclosed above. In some embodiments, the pocket may include an interface for control over the tool. In some embodiments, a cable, such as an electrical or optical cable, may be present in the endoscope in order communicate with the interface.

In some embodiments, sheath 1000 from FIG. 10A and flexible endoscope 1100 from FIG. 11A both, preferably, may have robotically controlled steerable distal ends. The structure of sheath 1000 and flexible endoscope 1100 enabling this control is thus substantially the same for both, and thus discussion for the construction of sheath 1000 will be limited to that of the sheath 1000 with the understanding that the same principles apply to the structure of the flexible endoscope 1100.

Therefore, tendons 1104 and 1105 and associated conduits 1106 and 1107 from the endoscope 1100 from FIG. 11A do not run longitudinally straight (i.e., approximately parallel to the neutral axis) down the length of endoscope 1100, but helix along different portions of endoscope 1100. As with the helixed tendons and conduits in sheath 1000, the helixed sections of endoscope 1100 may be determined based on the desired properties of the endoscope, taking into account desired flexibility of the shaft, and increased friction in the helixed section. Tendons 1104 and 1105 run approximately parallel to central axis of endoscope 1000 when not in the helixed section.

The purpose of the helixed section, as described more fully below, is to help isolate the bending to the distal section, while minimizing bending that occurs along the shaft proximal to the distal section. In some embodiments of the present invention, the helix pitch of the conduits in sheath 1000 and endoscope 1100 may be varied along the length of the helixed section, which, as more fully described below will alter the stiffness/rigidity of the shaft.

The use of helixed conduits and helixed tendons in sheath 1000 and endoscope 1100 present significant advantages over previous flexible instruments without helixed conduits, particularly when navigating non-linear pathways in anatomical structures. When navigating curved pathways, it is preferable for sheath 1000 and endoscope 1100 to remain flexible over most of the lengths thereof, and to have a controllably steerable distal end section, while also minimal secondary bending of the instrument proximal to the distal bending section. In previous flexible instruments, tensioning the tendons in order to articulate the distal end resulted in unwanted bending and torqueing along the entire length of the flexible instrument, which may be referred to as "muscling" and "curve alignment" respectively.

Figure 12A:
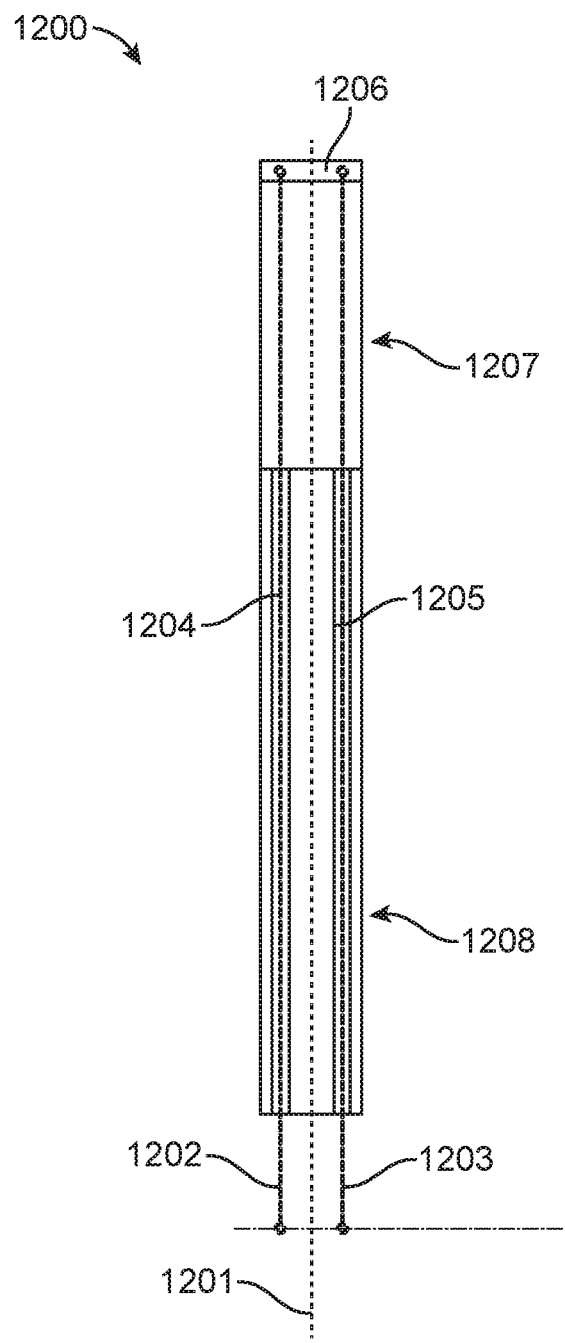
Figure 12B:
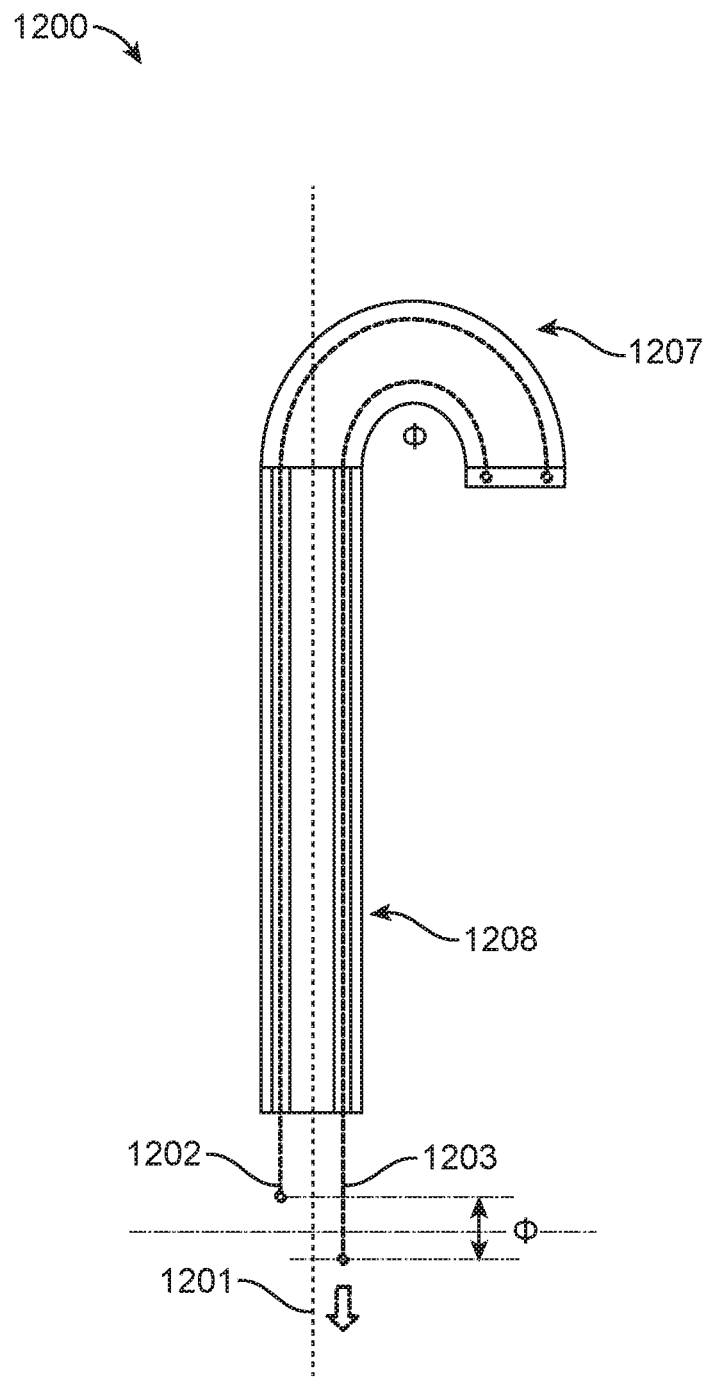
Figure 12C:
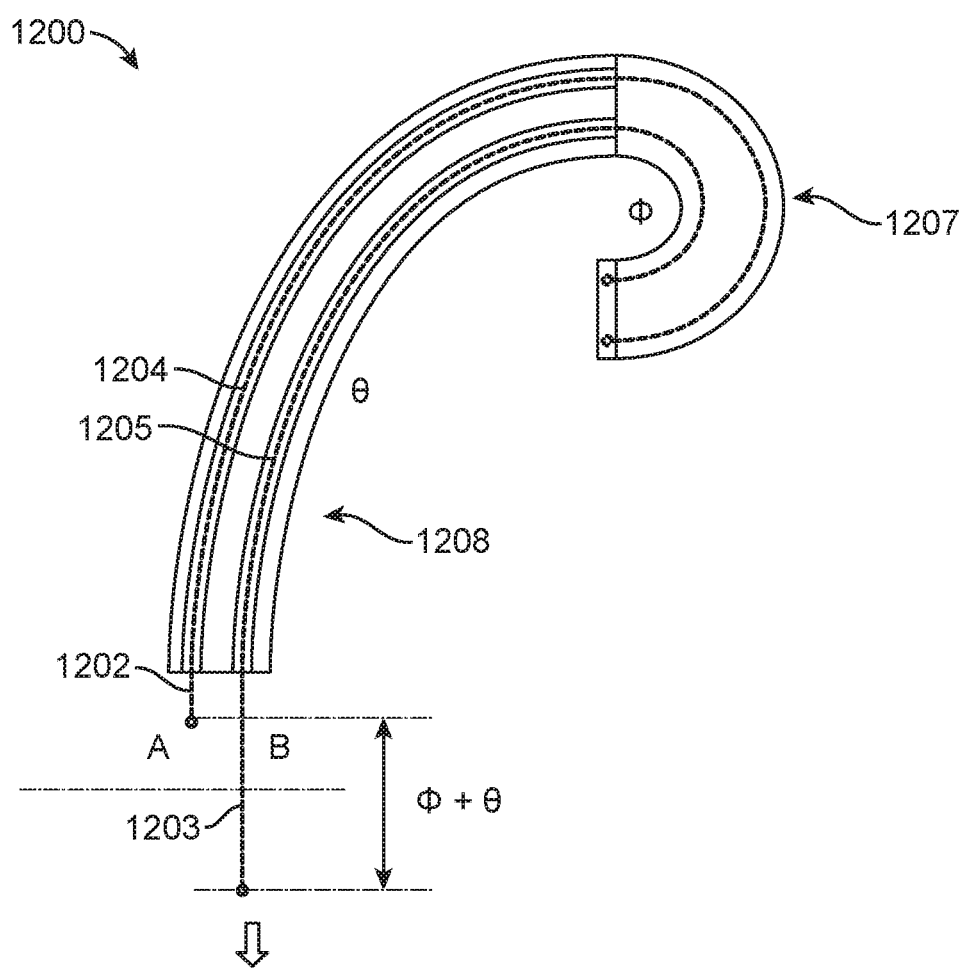

FIGS. 12A to 12C illustrates how the prior flexible instruments exhibit undesirable "muscling" phenomenon when tendons are pulled. In FIG. 12A, a previous flexible instrument 1200 may have four tendons or control wires along the length of the instrument 1200 that run approximately parallel to the neutral axis 1201. Only tendons 1202 and 1203 are shown in cross section traveling through conduits 1204 and 1205 (also known as control lumens) in the shaft wall, each of which are fixed connected to a control ring 1206 on the distal end of the instrument 1200. Instrument 1200 is intentionally designed to have a bending section 1207 and shaft 1207. In some flexible instruments, the shaft 1208 may incorporate stiffer materials, such as stiffeners.

FIG. 12B illustrates an idealized articulation of the bending section 1207. By pulling or exerting tension on tendon 1203, articulation of only the distal bending section 1207 results an amount represented by $\phi$, where the length difference at the proximal ends of tendons 1202 and 1203 would be a $f(\phi)$. In contrast, the shaft 1208 remains straight along the neutral axis 1201. This is achieved by having a proximal region 1208 of a significantly higher stiffness than the distal region of 1207.

FIG. 12C illustrates the real world result from tensioning tendon 1203. As shown in FIG. 12C, pulling tendon 1203 results in compressive forces along the entire length of the shaft as the tension is non-localized. In an idealized situation, were tendon 1203 along the neutral axis 1201, the entire compressive load would transmit equally down the central axis and most or all bending would occur at the bending section 1207. However, where the tendon 1203 runs along the periphery of the shaft 1208, such as in instrument 1200, the axial load is transferred off the neutral axis 1201 in the same radial orientation of the neutral axis which creates a cumulative moment along the neutral axis. This causes the shaft 1208 to bend (depicted as $\theta$), where the bend in the shaft 1208 will be in the same direction as the bend in the bending section 1207. The length along conduit 1204 and conduit 1205 must change as the instrument 1200 and distal bend section 1207 bend. The amount tendons 1202 and 1203 extend from the proximal end is $f(\phi,\theta)$, as tendon 1203 will need to shorten and tendon 1202 will need to lengthen. This phenomenon, where the shaft 1207 and distal bending section 1208 bend from pulling tendon 1203, is referred to as "muscling."

Figure 12D:
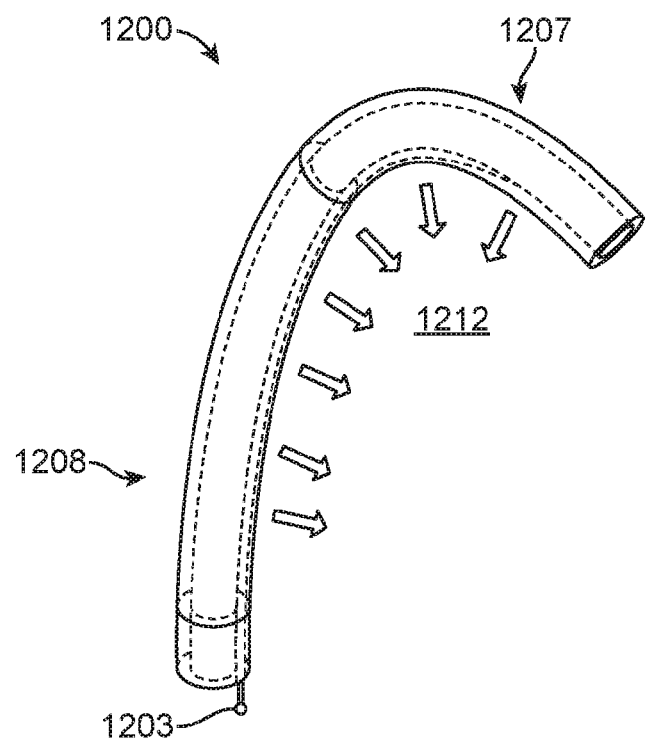
Figure 12E:
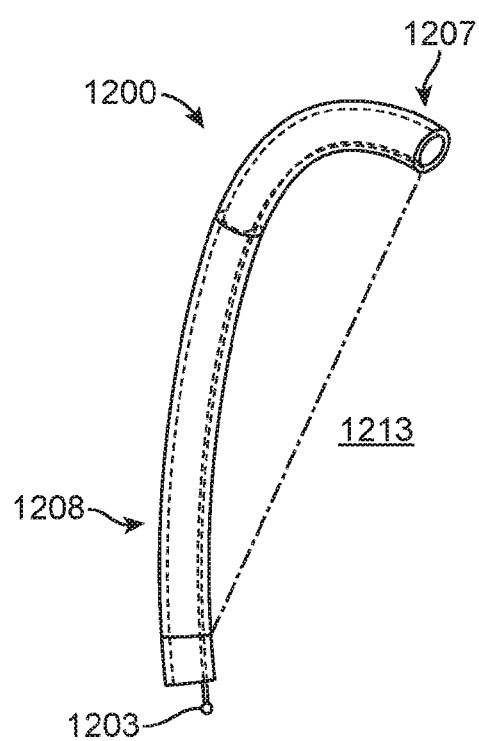

FIG. 12D illustrates the forces that contribute to muscling in three-dimensions. As shown by FIG. 12D, tensioning tendon 1203 along instrument 1200 causes the tendon 1203 to directionally exert forces 1212 towards one side of the instrument. The direction of forces 1212 reflect that the tension in tendon 1203 causes the tendon to seek to follow a straight line from the tip of the distal bending section 1207 to the base of the shaft 1208, i.e., the lowest energy state as represented by the dotted line 1213 in FIG. 12E. As will be appreciated, if the shaft 1208 is rigid (i.e., not susceptible to bending under the applicable forces), only the distal bending section 1207 will bend. However, in many applications it is not desirable to make the shaft rigidity sufficiently different from the distal end to adequately minimize the muscling phenomenon.

Figure 12F:
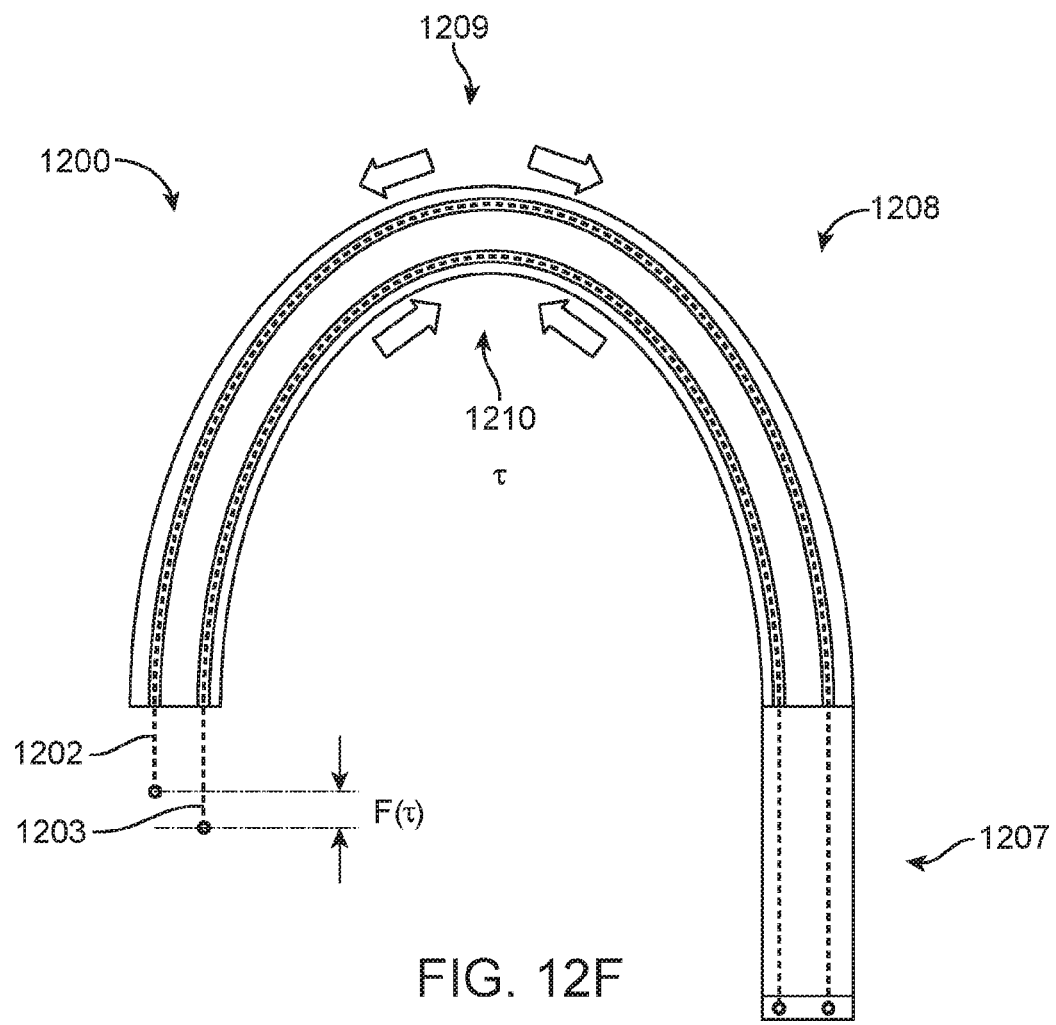

FIGS. 12F to 12I illustrate how previous flexible instruments suffer from curve alignment phenomenon during use in non-linear pathways. FIG. 12F shows a previous flexible instrument 1200 at rest within a non-linear path, represented by having a bend $\tau$ along the shaft 1208 of instrument 1200. For example, this may result from the instrument navigating past a bend in the bronchial lumens. Due to the non-linear bend, tendons 1202 and 1203 in instrument 1200 need to lengthen or shorten at the proximal end by a length to accommodate the non-linear bend, which length is represented by $F(\tau)$. Extension and compressive forces exist on the lumens/conduits at the top and bottom of the bend, as depicted by arrows 1209 (extension forces) and 1210 (compressive forces) respectively. These forces exist because the distance along the top of the bend is longer than the neutral axis, and the distance along the inside of the bend is shorter than the neutral axis.

Figure 12G:
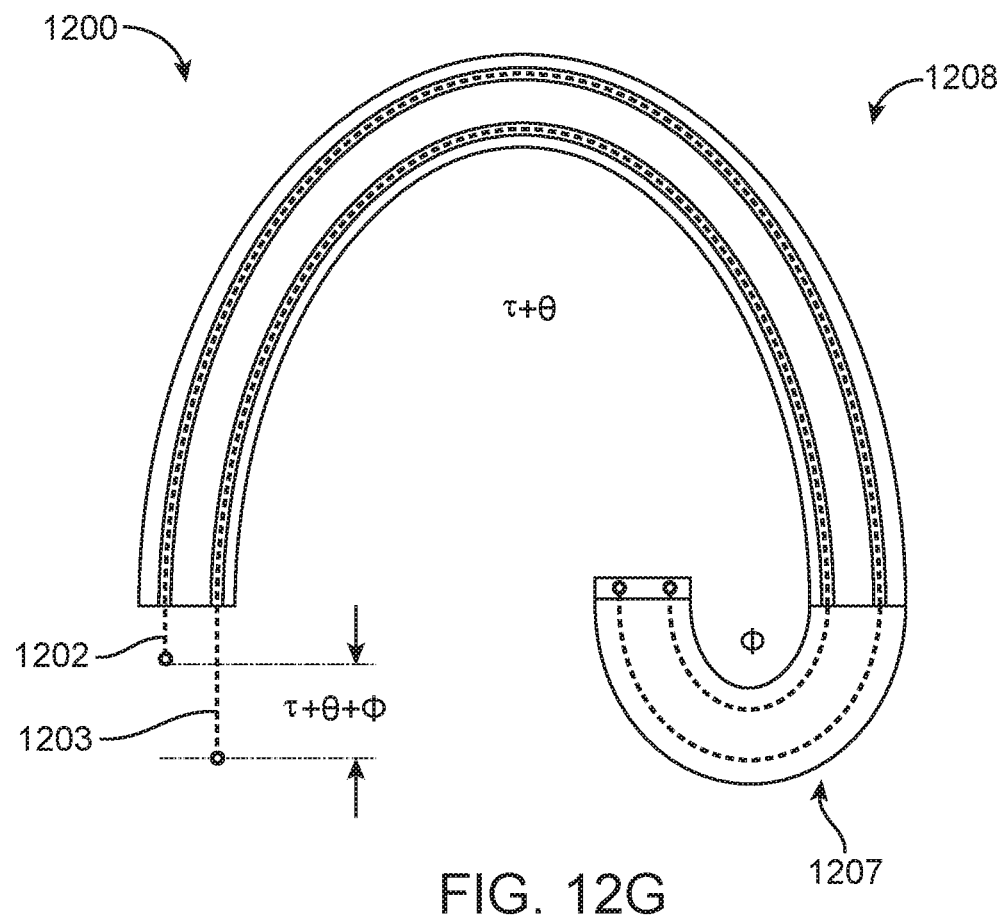
Figure 17H:
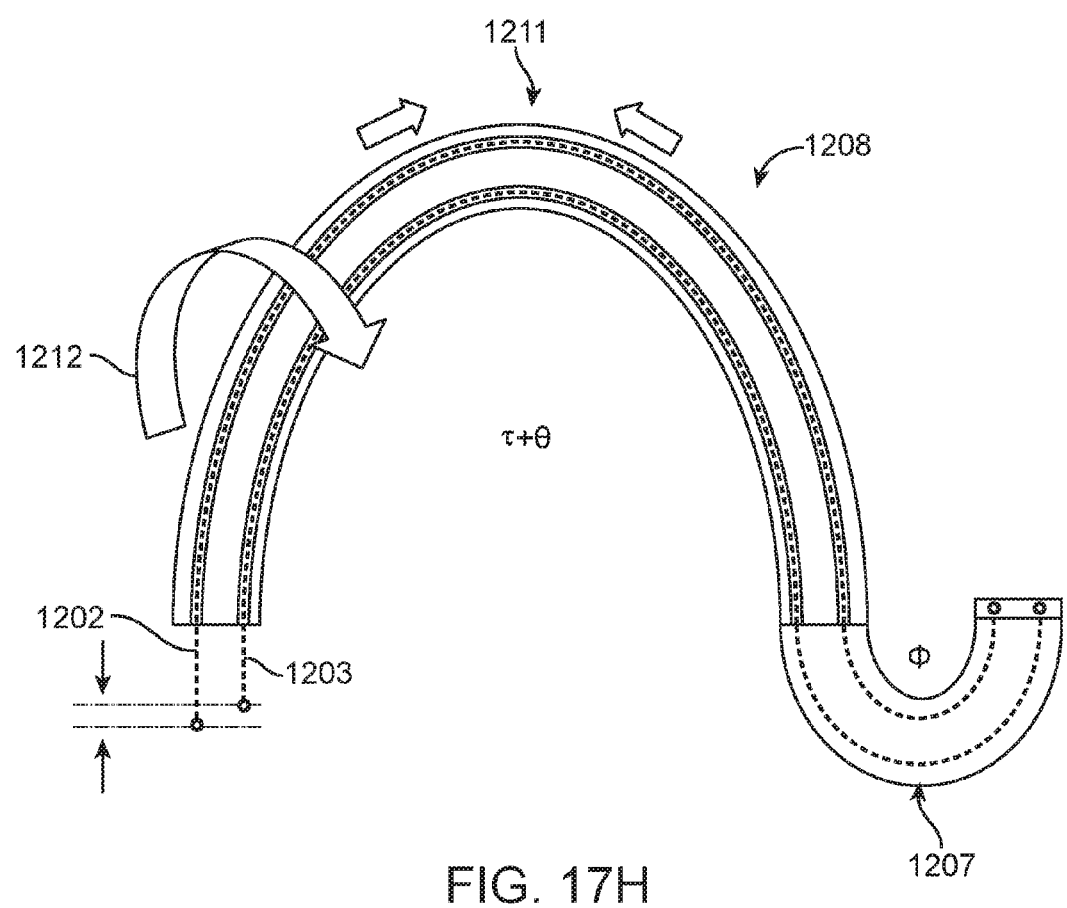
FIGS. 17A and 17B illustrate independent drive mechanisms of the present invention.

FIG. 12G illustrates the mechanics of articulating the distal bending section 1207 of the instrument 1200 in the same direction as bend $\tau$, where one would pull tendon 1203. This results in compressive forces along the length of the flexible instrument (as previously described), and tendon 1203 also exerts downward forces against the non-linear conduit through which it passes, which applies an additive compression in the shaft 1208 previously compressed by the anatomical tortuosity. Since these compressive leads are additive, the shaft 1208 will further bend in the same direction as the distal bending section 1207. The additional compressive force along the non-linear conduit is highly undesirable because: (i) it forces the flexible instrument against the anatomy causing potential injury; (ii) potential for injury distracts the operator because he/she has to constantly monitor what the shaft is doing, when he/she should be able to "assume" the anatomy is governing the profile of the instrument shaft; (iii) it is an inefficient way to bend the instrument, (iv) it is desired to isolate bending at the distal section to aid in predictability and controllability (i.e., ideal instrument will have bending section that bends as commanded and is not a function of the anatomical non-linear path), and (v) it forces a user to pull on a tendon 1103 an unpredictable additional length ($\phi+\theta+\tau$).

Figure 12I:
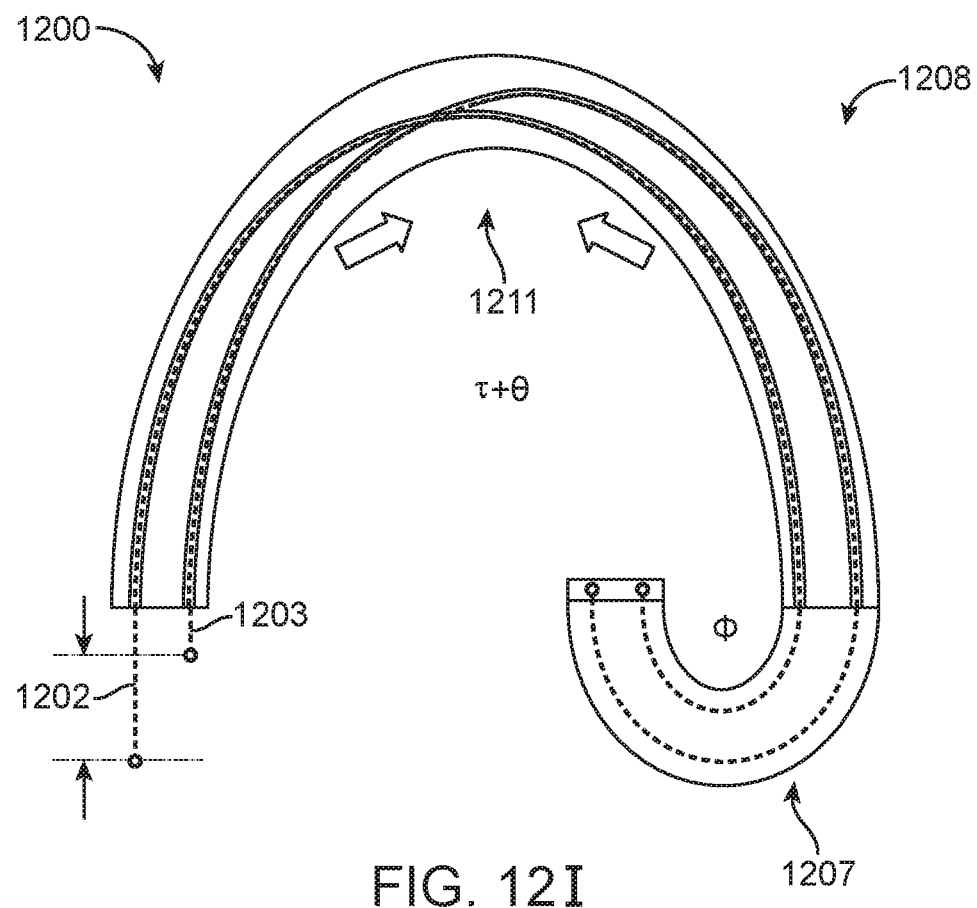

FIG. 12H illustrates a scenario where one desires to articulate the distal end opposite to bend $\tau$, requiring pulling tendon 1202. Pulling tendon 1202 applies a compressive load 1211 along the top of the curve, which is in contrast to the extension loads for the bend in its resting state as shown in FIG. 12D. Tendons 1202 will attempt to return to its lowest energy state, i.e., where the compressive load 1211 rests on the inside of the bend $\tau$, and cause the shaft 1208 to rotate in the direction of the arrow 1212 so that the tendon 1202 rests on the inside of the bend $\tau$. As shown in FIG. 12I, the rotation 1212 from tension on tendon 1202 moves the compressive load 1211 to return to the inside of the bend and causes the distal bending section 1207 to curl back in the direction of bend $\tau$, resulting in articulation opposite to that intended. The tension on tendon 1202, and the ensuing rotation 1212, in practice returns instrument 1200 to the same state as in FIG. 12G. The phenomenon where the distal end articulation curves back towards bend $\tau$ is known as "curve alignment." It will be appreciated that curve alignment results from the same forces that cause muscling, wherein those forces result in undesirable lateral motion in the case of muscling and undesirable rotational motion in the case of curve alignment. It is noted that the discussions of the theory of muscling and curve alignment is provided not by way of limitation, and embodiments of the present invention are not in any way limited by this explanation.

Figures 12J, 12K:
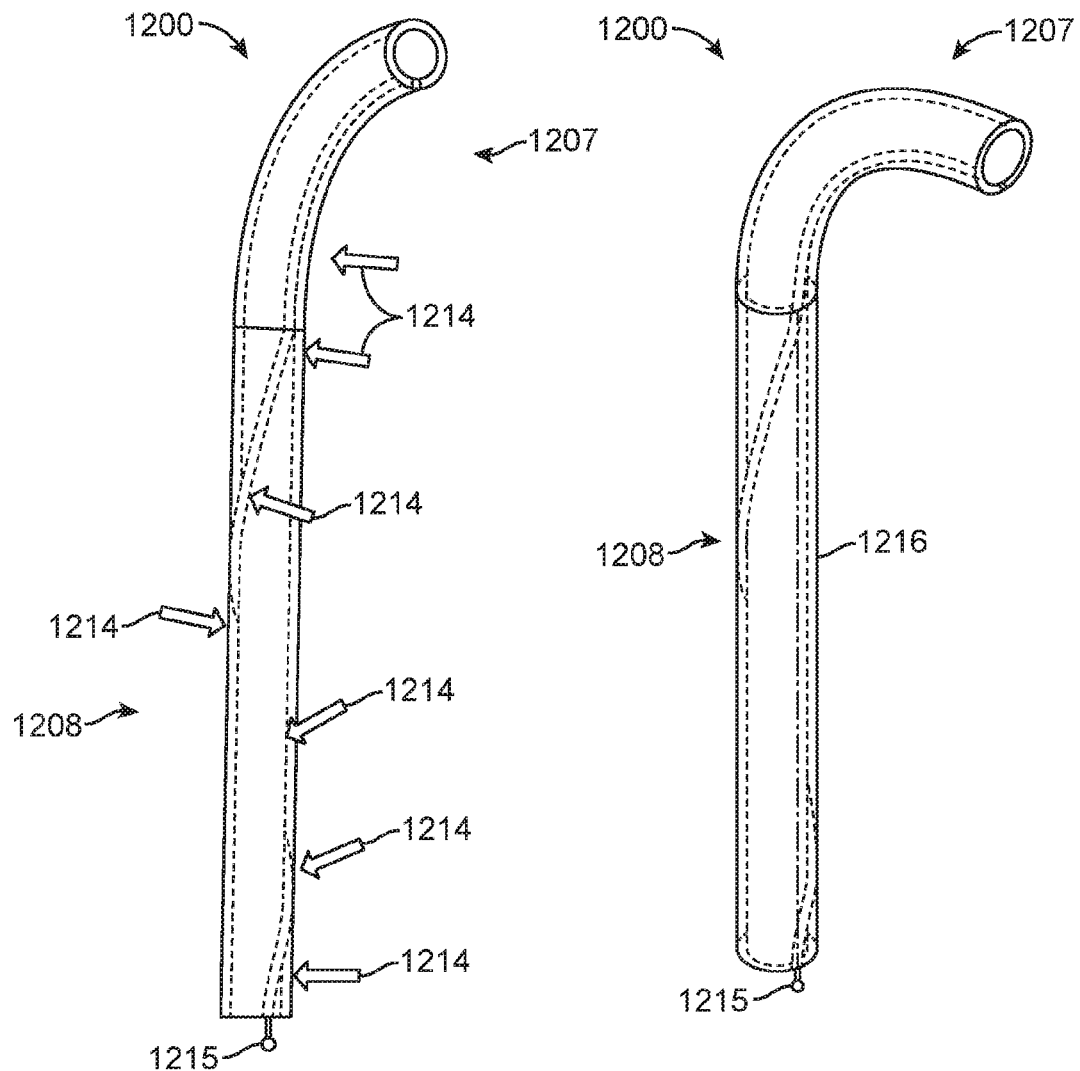

The preferred embodiment disclosed in FIGS. 10 and 11 substantially resolves the muscling and curve alignment phenomena through the provision of helixed section 1010. As shown in FIG. 12J, helixing the control lumens around instrument 1200, such as in helixed section 1010 from FIGS. 10B and 10C, radially distributes compressive loads 1214 from a single tendon 1215 around instrument 1200. Because a tensioned tendon 1215 symmetrically transmits the compressive load 1214 in multiple directions around the neutral axis, the bending moments imposed on the shaft are also symmetrically distributed around the longitudinal axis of the shaft, which counterbalance and offset opposing compressive and tensile forces. The distribution of the bending moments results in minimal net bending and rotational forces, creating a lowest energy state that is longitudinally parallel to the neutral axis, as represented by the dotted line 1216. This eliminates or substantially reduces the muscling and curve alignment phenomena.

In some embodiments, the pitch of helixing can be varied to affect friction and the stiffness of the helixed section. For example, the helixed section 1010 may be shorter to allow for a larger non-helixed section 1009, resulting in a larger articulating section and possibly less friction.

Helical control lumens, however, create several trade-offs. Helical control lumens still do not prevent buckling from tension in the tendons. Additionally, while muscling is greatly reduced, "spiraling"—the curving of the shaft into a spiral, spring-like pattern due to tension in the tendons—is very common. Moreover, helical control lumens requires compensation for additional frictional forces as the tendon travels through the lumen for longer distances.

Figure 13:
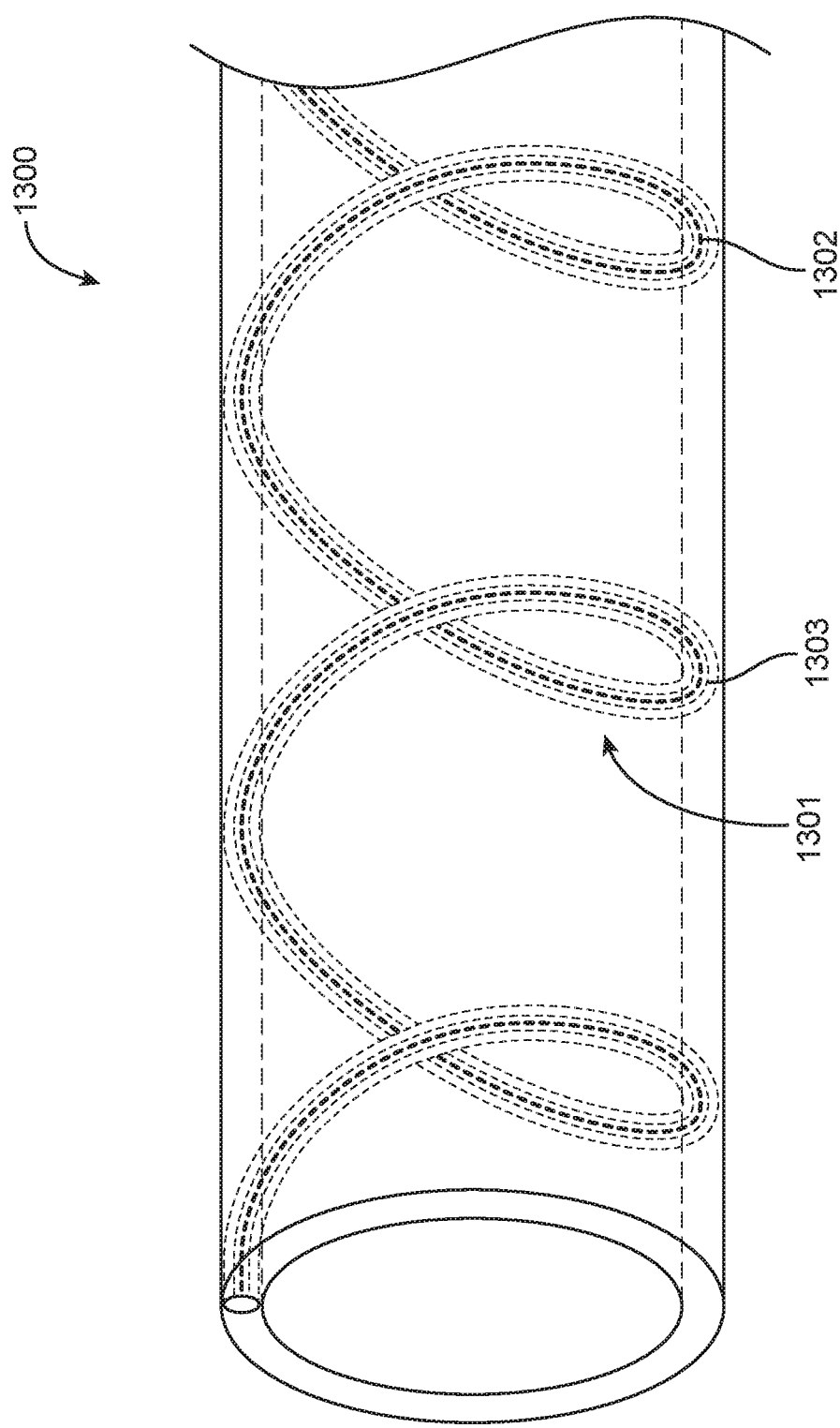
FIG. 13 illustrates the structure of flexible endoscopic device with an axially stiff tube within a lumen, in accordance with an embodiment of the present invention.

FIG. 13 illustrates the structure of a flexible endoscopic device with an axially stiff tube within a lumen, in accordance with an embodiment of the present invention. In FIG. 13, a section of an endoscopic device has a single lumen 1301 with a pull wire 1302 wrapped in a helical pattern around the shaft 1300. Inside the lumen, an axially stiff tube 1303 "floats" around the pull wire 1302 and within the lumen 1301. Anchored at the beginning and end of the helical portion of the shaft 1300, the floating tube 1303 extends and compresses in response to tension in pull wire 1302 and external tortuosity, relieving the walls of lumen 1301 from the extension and compression forces. In some embodiments, the tube 1303 may be anchored by pull rings at the beginning and end of the lumen. Alternatively, tube 1303 may be anchored using solder, welding, gluing, bonding, or fusing methods to the beginning and end of the lumen. In some embodiments, geometric engagement, such as flared geometries, may be used to anchor tube 1303. In various embodiments, the tube 1303 may be formed from hypodermic tubes, coil pipes, Bowden cables, torque tubes, stainless steel tubes, or nitinol tubes.

The embodiment in FIG. 13 may be constructed by fixedly attaching the tubes to a distal end piece and proximal end piece and collectively twisting the tubes by rotating either or both end pieces. In this embodiment, the rotation of the end piece(s) ensures that the tubes are helixed in the same pitch, manner, and orientation. After rotation, the end pieces may be fixedly attached to the lumen to prevent further rotation and restrict changes to the pitch of the helixing.

Figure 14:
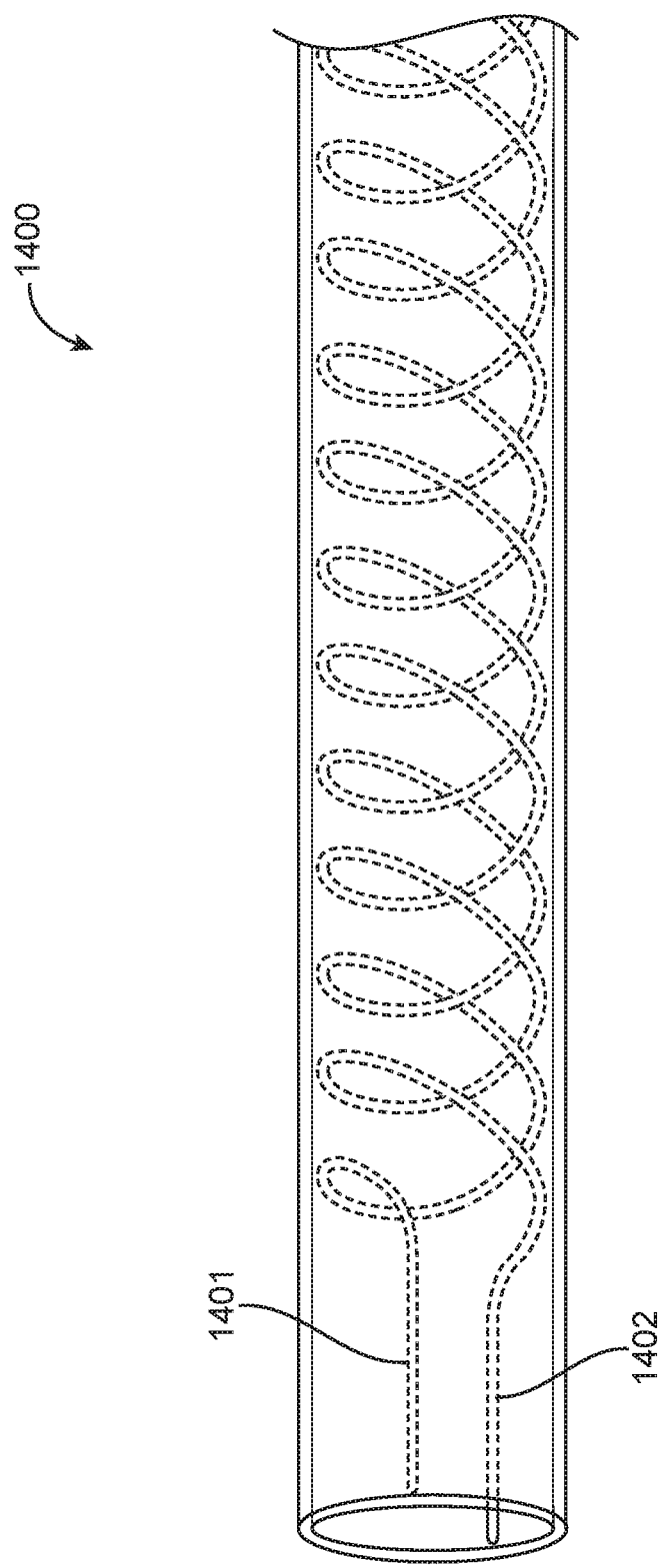
FIG. 14 illustrates the structure of a helical pattern within a lumen of a flexible endoscopic device, in accordance with an embodiment of the present invention.

FIG. 14 illustrates the structure of a helical pattern within a lumen of a flexible endoscopic device, in accordance with an embodiment of the present invention. In FIG. 14, lumen 1400 contains structures 1401 and 1402 that form a helical or spiraled pattern along its walls. In preferred embodiments, the structures are formed from materials that are axially stiff and tube-like in shape. In some embodiments, the structures may be formed from hypodermic tubes ("hypo tube"), coil pipes, or torque tubes. As shown by structures 1401 and 1402, the structures may have different starting points along the walls of lumen 1400. The materials, composition, and characteristics of structures 1401 and 1402 may also be selected and configured for desired stiffness and length. The pitch of the helical pattern formed by structures 1401 and 1402 may also be configured for a desired stiffness and flexibility of lumen 1400. In some embodiments, lumen 1400 may be the main central lumen of a flexible endoscope, such as endoscope 1100 from FIG. 11.

Robotic Catheter System.

Figure 15A:
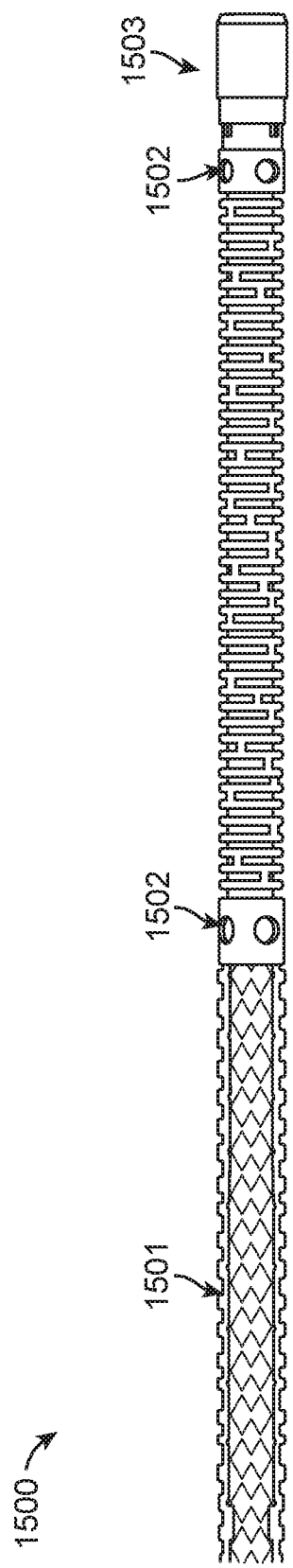
FIG. 15A illustrates a robotic catheter from a robotic catheter system, in accordance with an embodiment of the present invention.

FIG. 15A illustrates a robotic catheter from a robotic catheter system, in accordance with an embodiment of the present invention. Robotic catheter 1500 may comprise of a flexible shaft section 1501 proximal to a support base (not shown) and a flexible articulating section 1502 coupled to a distal tip 1503. Similar to the leader 1505, robotic catheter 1500 may be articulated by placing tensile loads on tendons within the shaft.

Figure 15B:
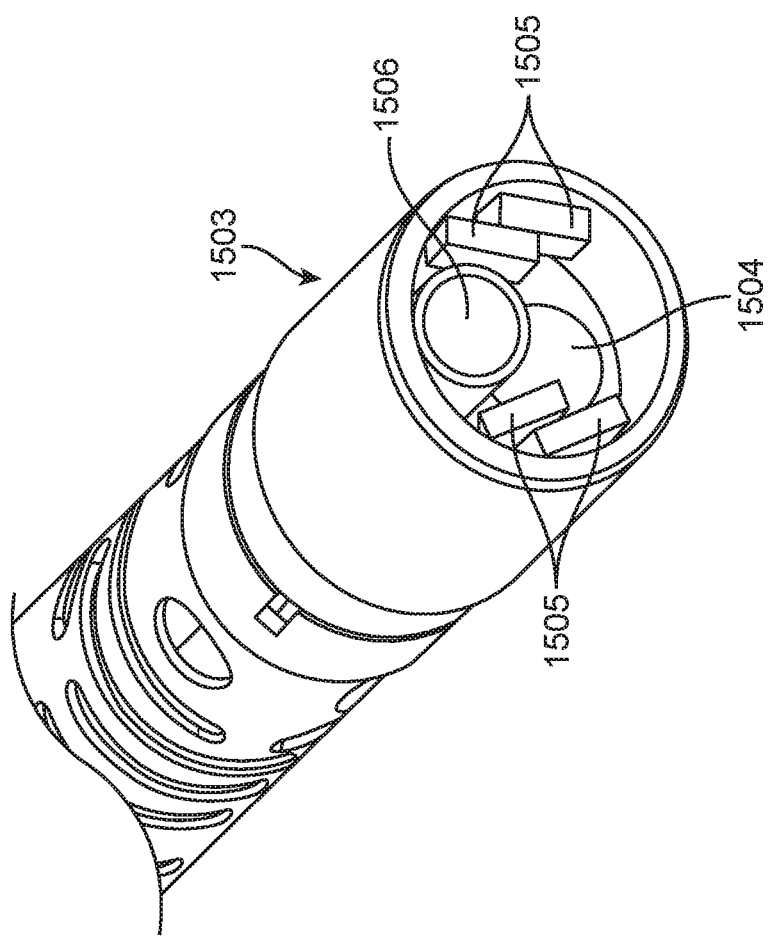
FIG. 15B illustrates an alternative view of robotic catheter 1500 from FIG. 15A.

FIG. 15B illustrates an alternative view of robotic catheter 1500 from FIG. 15A. As shown in FIG. 15B, the distal tip 1503 may comprise a working channel 1504, four light emitting diodes 1505, and a digital camera 1506. In conjunction with the LEDs 1505, the digital camera 1506 may be used, for example, to capture real-time video to assist with navigation within anatomical lumens. In some embodiments, the distal tip 1503 may comprise an integrated camera assembly which houses a digital imaging means and illumination means.

The working channel 1504 may be used for the passage of intraoperative instruments, such as bending flexures for precise articulation at an operative site. In other embodiments, working channels may be incorporated to provide additional capabilities such as flush, aspiration, illumination or laser energy. The working channel may also facilitate the routing of control tendon assemblies and other lumens needed for the aforementioned additional capabilities. The working channel of the robotic catheter may also be configured to deliver a variety of other therapeutic substances. Such substances may be cryogenic for ablation, radiation, or stem cells. These substances may be precisely delivered precisely to a target site using the insertion, articulation, and capability of the robotic catheter of the present invention. In some embodiments, the working channel may be as small at 1.2 millimeters in diameter.

In some embodiments, an electromagnetic (EM) tracker may be incorporated into the distal tip 1503 in order to assist with localization. As will be discussed later, in a static EM field generator may be used to determine the location of the EM tracker, and thus distal tip 1503 in real-time.

Images from camera 1506 may be ideal for navigating through anatomical spaces. Thus, obscuring of the camera 1506 from internal bodily fluids, such as mucus, may cause problems when navigating. Accordingly, the distal end 1503 of robotic catheter 1500 may also include means for cleaning the camera 1506, such as means for irrigation and aspiration of the camera lens. In some embodiments, the working channel may contain a balloon that may be inflated with fluid around the camera lens and aspirated once the lens was clear.

The robotic catheter 1500 enables the delivery and manipulation of small instruments within a small anatomical space. In a preferred embodiment, the distal tip may be miniaturized in order to perform endolumenal procedures, maintaining an outer diameter of no more than three millimeters (i.e., nine French).

Figure 16:
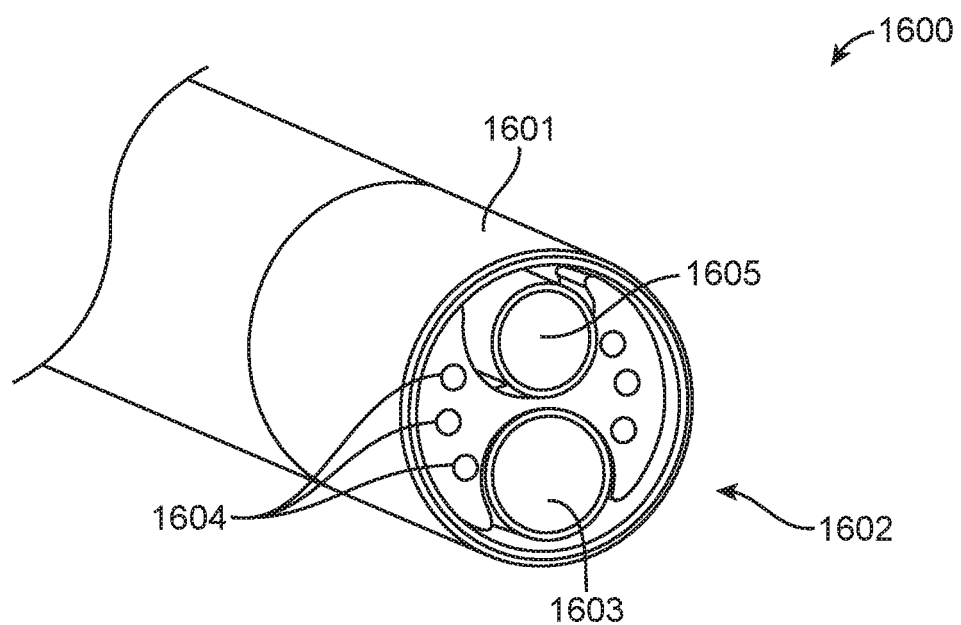
FIG. 16 illustrates the distal end of a robotic catheter, in accordance with an embodiment of the present invention.

FIG. 16 illustrates the distal end of a robotic catheter, in accordance with an embodiment of the present invention. As in FIG. 15A, robotic catheter 1600 similarly includes a distal end 1601 with an outer casing 1602. Casing 1602 may be constructed from a number of materials including stainless steel and polyether ether ketone (PEEK). The distal end 1601 may be packed with a working channel 1603 for slidingly providing tool access and control. The distal end 1601 may also provide for an array of light emitting diodes 1604 for illumination with use of the camera 1605. In some embodiments, the camera may be part of a larger sensor assembly that includes one or more computer processors, a printed circuit board, and memory. In some embodiments, the sensor assembly may also include other electronic sensors such as gyroscopes and accelerometers (usage discussed later).

Instrument Device Manipulator (IDM).

In some embodiments, the mechanism changer interface may be a simple screw to secure an associated IDM. In other embodiments, the mechanism changer interface may be a bolt plate with an electrical connector.

Figure 17A:
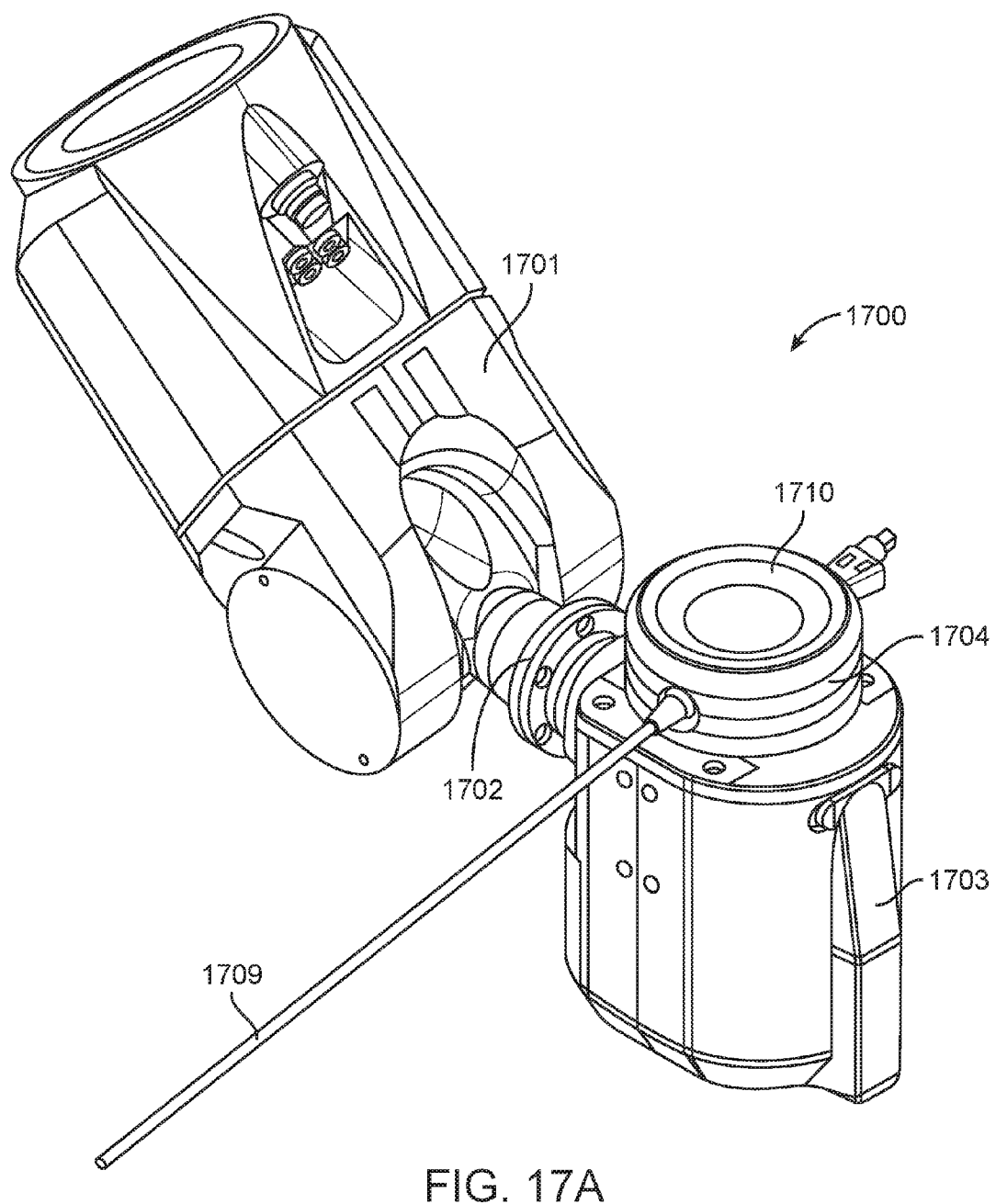

FIG. 17A illustrates a portion of a robotic medical system that includes a manipulator, in accordance with an embodiment of the present invention. System 1700 includes a partial view of a robotic arm 1701, an articulating interface 1702, an instrument device manipulator ("IDM") 1703, and a robotic catheter 1704. In some embodiments, the robotic arm 1701 may be only a linkage in a larger robotic arm with multiple joints and linkages. The articulating interface 1702 couples IDM 1703 to robotic arm 1701. In addition to coupling, the articulating interface 1702 may also transfer pneumatic pressure, power signals, control signals, and feedback signals to and from the arm 1701 and the IDM 1703.

The IDM 1703 drives and controls the robotic catheter 1704. In some embodiments, the IDM 1703 uses angular motion transmitted via output shafts in order to control the robotic catheter 1704. As discussed later, the IDM 1703 may comprise a gear head, motor, rotary encoder, power circuits, control circuits.

Robotic catheter 1704 may comprise a shaft 1709 with a distal tip and proximal end. A tool base 1710 for receiving the control signals and drive from IDM 1703 may be coupled to the proximal end of the shaft 1709. Through the signals received by the tool base 1710, the shaft 1709 of robotic catheter 1704 may be controlled, manipulated, and directed based on the angular motion transmitted via output shafts 1705, 1706, 1707, and 1708 (see FIG. 17B) to the tool base 1710 of the robotic catheter 1704.

Figure 17B:
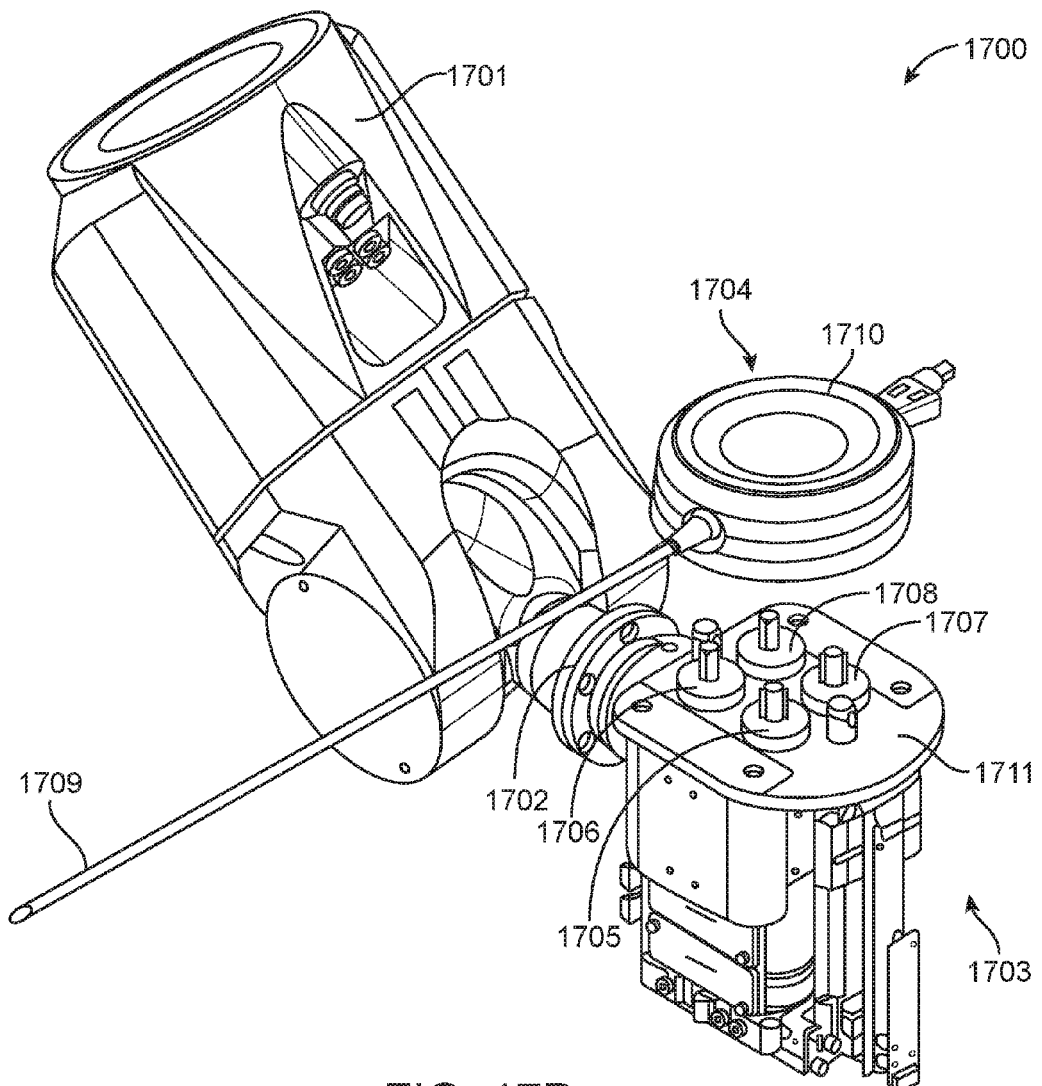

FIG. 17B illustrates an alternative view of the robotic medical system disclosed in FIG. 17A. In FIG. 17B, the robotic catheter 1704 has been removed from the IDM 1703, to reveal the output shafts 1705, 1706, 1707, and 1708. Additionally, removal of the outer skin/shell of IDM 1703 reveals the components below the IDM top cover 1711.

Figure 18:
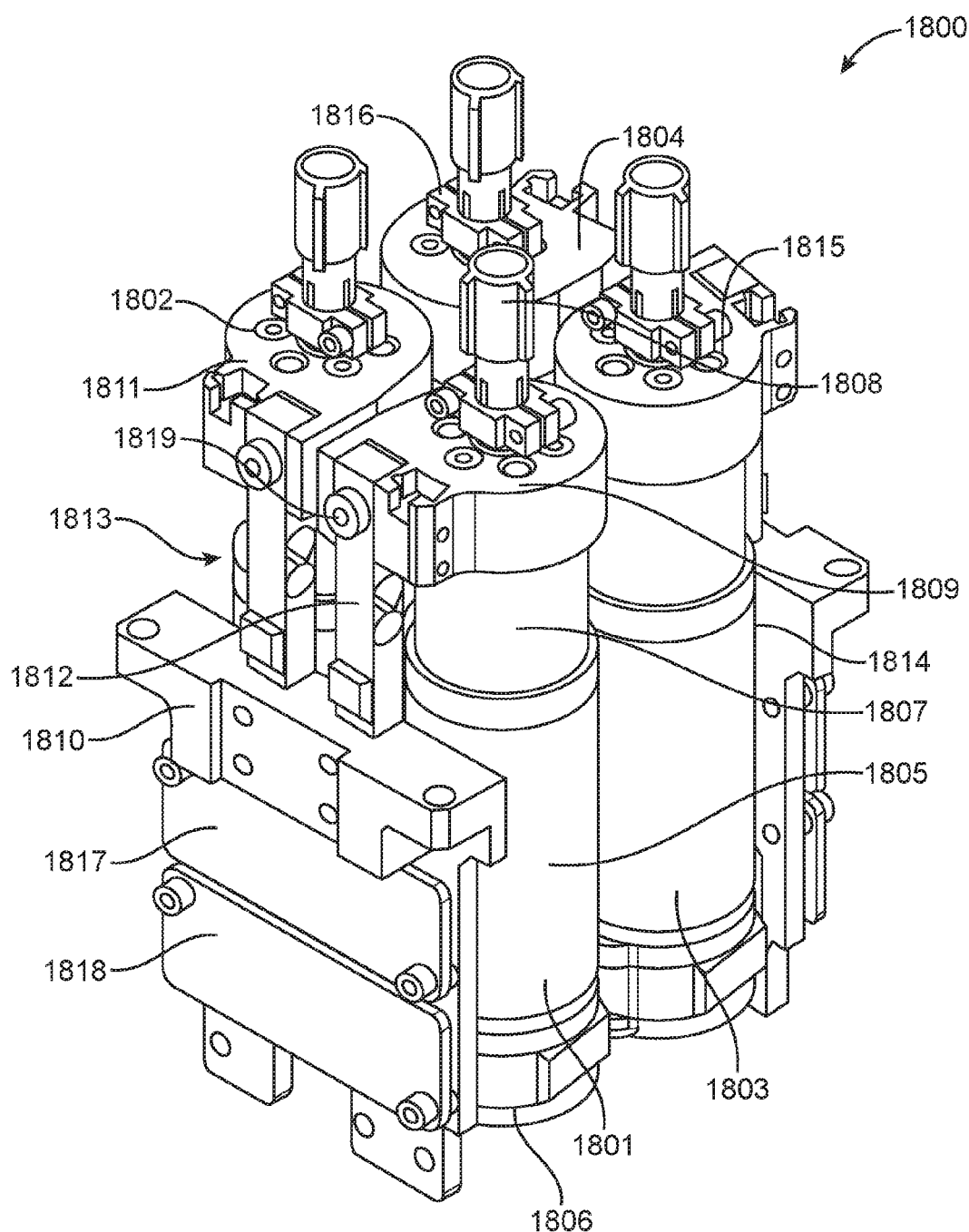
FIG. 18 illustrates an alternative view of the independent drive mechanism from FIGS. 17A and 17B illustrate the structure of a sheath of a flexible endoscopic device, with a tension sensing apparatus in accordance with an embodiment of the present invention.

FIG. 18 illustrates an alternative view of the independent drive mechanism from FIGS. 17A, 17B with a tension sensing apparatus in accordance with an embodiment of the present invention. In cutaway view 1800 of IDM 1703, parallel drive units 1801, 1802, 1803, and 1804 are the structurally largest components in the IDM 1703. In some embodiments, from the proximal to the distal end, a drive unit 1801 may be comprised of a rotary encoder 1806, a motor 1805, and a gear head 1807. Drive units 1802, 1803, and 1804 may be constructed similarly—comprising of motors, encoders, and gear heads underneath the top cover 1711. In some embodiments, the motor used in the drive unit is a brushless motor. In other embodiments, the motor may be a direct current servo motor.

Rotary encoder 1806 monitors and measures the angular speed of the driveshaft of motor 1805. In some embodiments, rotary encoder 1806 may be a redundant rotary encoder. The structure, capabilities, and use of an appropriate redundant encoder is disclosed in U.S. Provisional Patent Application No. 62/037,520, filed Aug. 14, 2014, the entire contents of which are incorporated by reference.

The torque generated by the motor 1805 may be transmitted to gear head 1807 through a shaft coupled to the rotor of motor 1805. In some embodiments, the gear head 1807 may be attached to the motor 1805 in order to increase torque of the motor output, at the cost of the rotational speed. The increased torque generated by gear head 1807 may be transmitted into gear head shaft 1808. Similarly, drive units 1802, 1803, and 1804 transmit their respective torque out through gear head shafts 1706, 1707, and 1708.

Each individual drive unit may be coupled to a motor mount at its distal end and a strain gauge mount towards its proximal end. For example, the distal end of drive unit 1801 may be clamped to motor mount 1809 and strain gauge mount 1810. Similarly, drive unit 1802 may be clamped to motor mount 1811, while also both being clamped to strain gauge mount 1810. In some embodiments, the motor mounts are constructed from aluminum to reduce weight. In some embodiments, the strain gauge mounts may be adhered to a side of the drive unit. In some embodiments, the strain gauge mounts may be constructed from aluminum to reduce weight.

Electrical strain gauges 1812 and 1813 are potted and soldered to the strain gauge mount 1810 and attached using screws to motor mounts 1809 and 1811 respectively. Similarly, a pair of strain gauges (not shown) proximal to drive units 1803 and 1804 are potted and soldered to strain gauge mount 1814 and attached to motor mounts 1815 and 1816 respectively using screws. In some embodiments, the electrical strain gauges may be held in place to their respective motor mount using side screws. For example, side screws 1819 may be inserted into motor mount 1809 to hold in place strain gauge 1812. In some embodiments, the gauge wiring in the electrical strain gauges may be vertically arranged in order to detect any vertical strain or flex in the drive unit which may be measured as horizontal displacement by the motor mount (1809, 1811) relative to the strain gauge mount (1810).

The strain gauge wiring may be routed to circuits on the strain gauge mounts. For example, strain gauge 1812 may be routed to circuit board 1817 which may be mounted on strain gauge mount 1810. Similarly, strain gauge 1813 may be routed to circuit board 1818 which may be also mounted on strain gauge mount 1810. In some embodiments, circuit boards 1817 and 1818 may process or amplify the signals from strain gauges 1812 and 1813 respectively. The close proximity of circuit boards 1817 and 1818 to strain gauges 1812 and 1813 helps to reduce the signal to noise ratio in order to obtain more accurate readings.

Figure 19A:
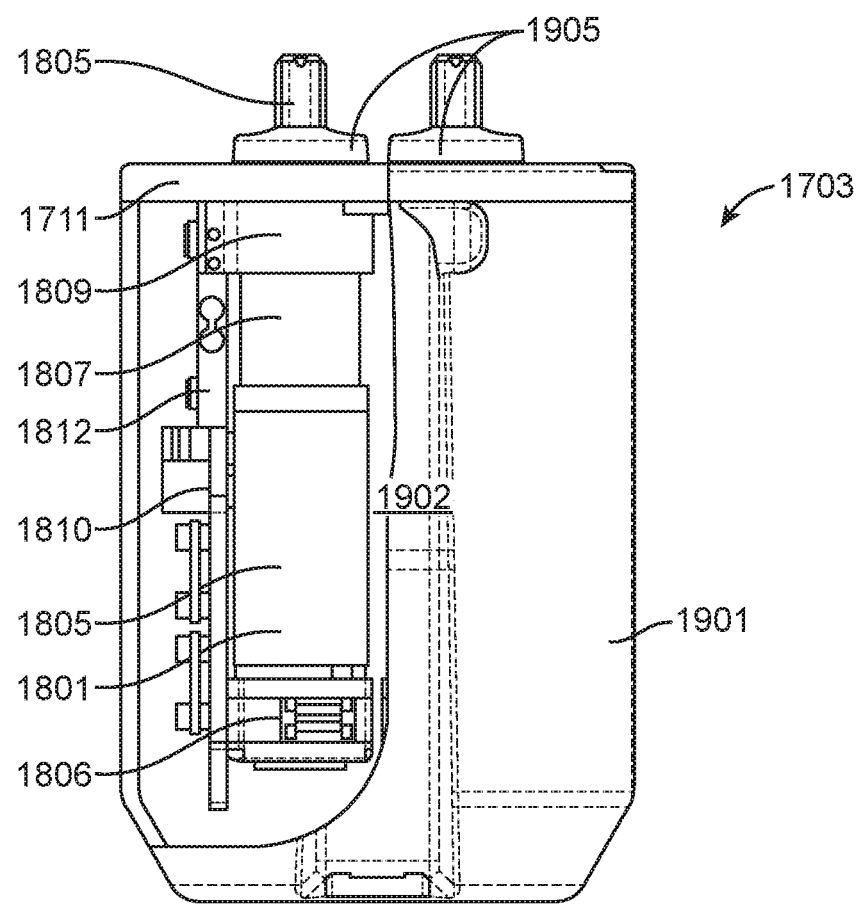
FIG. 19A illustrates a cutaway view of the independent drive mechanism from FIGS. 17A, 17B, and 18 from an alternate angle.

FIG. 19A illustrates a cutaway view of the independent drive mechanism from FIGS. 17A, 17B, and 18 from an alternate angle. As shown in FIG. 19A, a portion of outer shell/skin 1901 has been cut away to reveal the innards of IDM 1703. As discussed earlier, the drive unit 1801 comprises of motor 1805, rotary encoder 1806, and gear head 1807. The drive unit 1801 may be coupled to the motor mount 1809 and passes through the top cover 1711 through which the output shaft 1705 may be driven at the desired angular speed and torque. The motor mount 1809 may be coupled to a vertically aligned strain gauge 1812 using side screws. In addition to coupling to motor mount 1809, the stain gauge 1812 may be potted into the strain gauge mount 1810. In some embodiments, the output shaft 1705 includes a labyrinth seal over a gear head shaft.

Figure 19B:
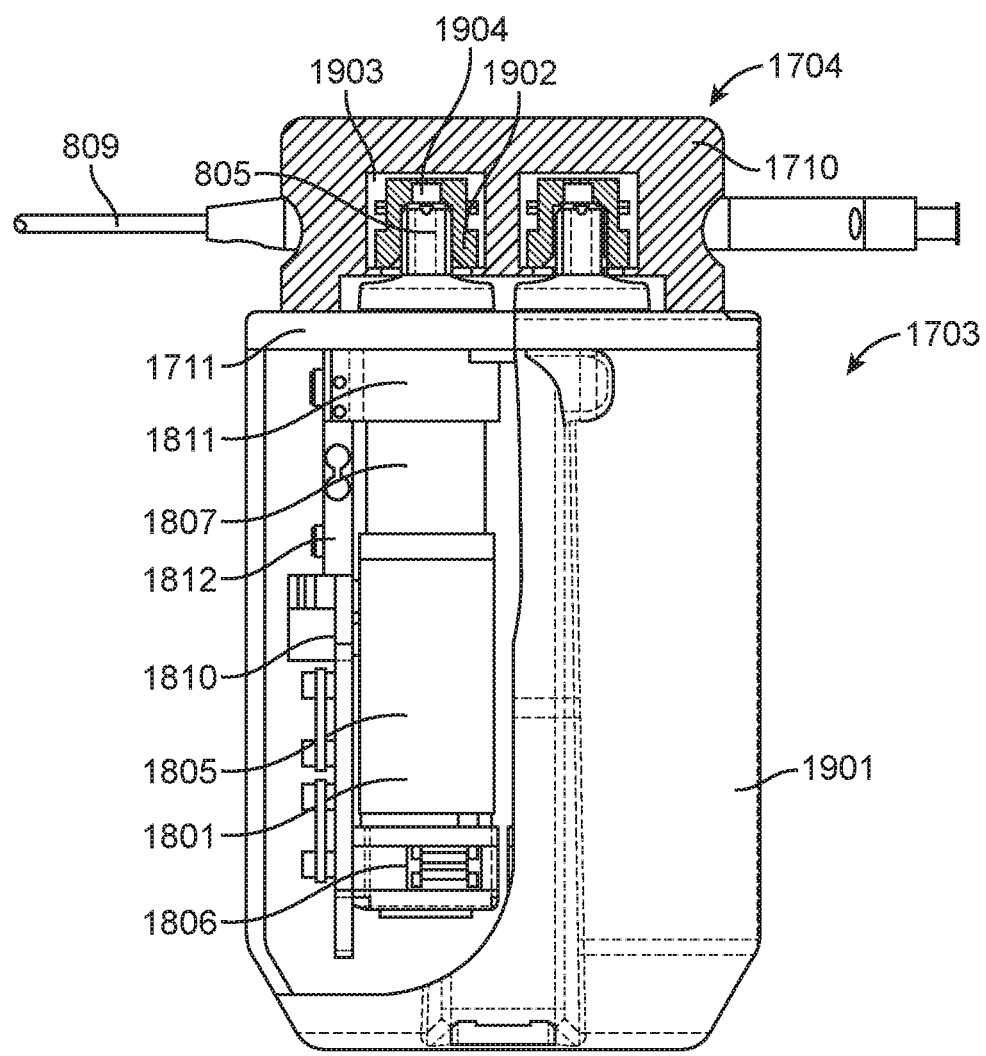
FIG. 19B illustrates a cutaway view of the previously discussed independent drive mechanism in combination with a robotic catheter, in accordance with an embodiment of the present invention.

FIG. 19B illustrates a cutaway view of the previously discussed independent drive mechanism in combination with a robotic catheter, in accordance with an embodiment of the present invention. As shown in FIG. 19B, robotic catheter 1704, mounted on IDM 1703, contains pulleys that are longitudinally aligned with the output shafts of the IDM 1703, such as pulley 1902 which may be concentric with output shaft 1705. Pulley 1902 may be housed inside of a precision cut chamber 1903 within tool base 1710 such that the pulley 1902 may be not rigidly fixed inside chamber 1903 but rather "floats" within the space in the chamber 1903.

The splines of the pulley 1902 are designed such that they align and lock with splines on output shaft 1705. In some embodiments, the splines are designed such that there may be only a single orientation for the robotic catheter to be aligned with IDM 1703. While the splines ensure pulley 1902 is concentrically aligned with output shaft 1705, pulley 1902 may also incorporate use of a magnet 1904 to position and axially hold the floating pulley 1902 in alignment with output shaft 1705. Locked into alignment, rotation of the output shaft 1705 and pulley 1902 tensions the pull wires within robotic catheter 1704, resulting in articulation of shaft 1709.

Figure 20:
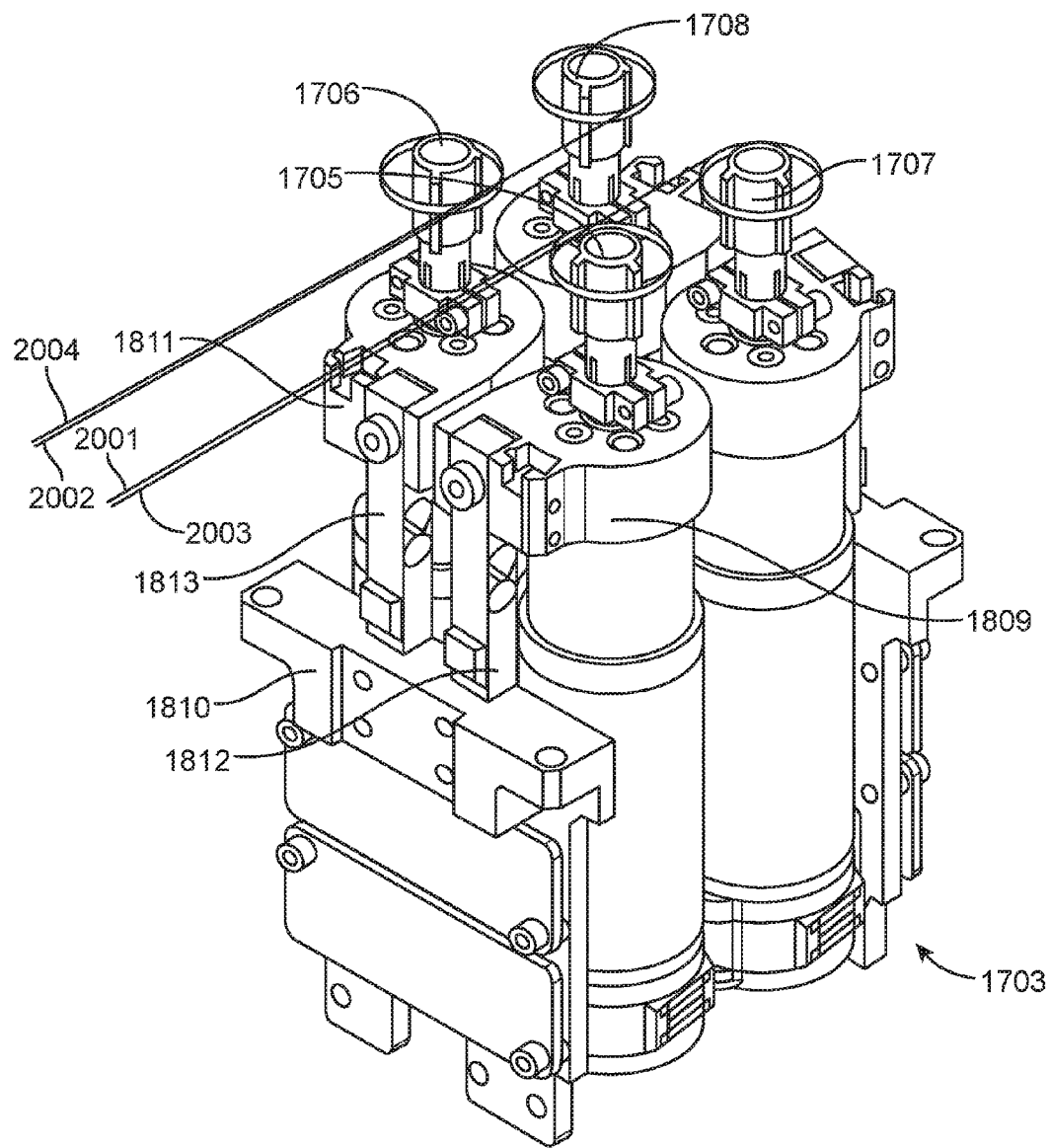
FIG. 20 illustrates an alternative view of the previously-discussed independent drive mechanism with pull wires from a robotic catheter in accordance with an embodiment of the present invention.

FIG. 20 illustrates an alternative view of the previously-discussed independent drive mechanism with pull wires from a robotic catheter in accordance with an embodiment of the present invention. In some embodiments, the robotic catheter may use pull wires in order to articulate and control the shaft. In those embodiments, these pull wires 2001, 2002, 2003, and 2004 may be tensioned or loosened by the output shafts 1705, 1706, 1707, and 1708 respectively of the IDM 1703. Accordingly, the pull wires may be robotically controlled via the control circuitry in IDM 1703.

Just as the output shafts 1705, 1706, 1707, and 1708 transfer force down pull wires 2001, 2002, 2003, and 2004 through angular motion, the pull wires 2001, 2002, 2003, and 2004 transfer force back to the output shafts and thus to the motor mounts and drive units. For example, tension in the pull wires directed away from the output shaft results in forces pulling the motor mounts 1809 and 1811. This force may be measured by the strain gauges, such as 1812 and 1813, since the strain gauges are both coupled to motor mounts 1809 and 1811 and potted in the strain gauge mount 1810.

Figure 21:
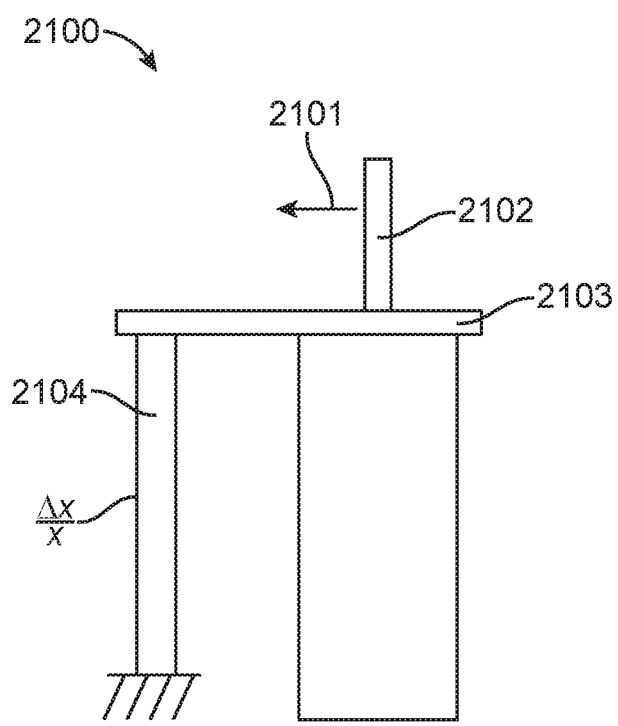
FIG. 21 illustrates a conceptual diagram that shows how horizontal forces may be measured by a strain gauge oriented perpendicular to the forces, in accordance with an embodiment of the invention.

FIG. 21 illustrates a conceptual diagram that shows how horizontal forces may be measured by a strain gauge oriented perpendicular to the forces, in accordance with an embodiment of the invention. As shown in diagram 2100, a force 2101 may directed away from the output shaft 2102. As the output shaft 2102 is coupled to the motor mount 2103, the force 2101 results in horizontal displacement of the motor mount 2103. The strain gauge 2104, coupled to both the motor mount 2103 and ground 2105, may thus experience strain as the motor mount 2103 causes the strain gauge 2104 to flex (causing strain) in the direction of the force 2101. The amount of strain may be measured as a ratio of the horizontal displacement of the tip of strain gauge 2104 to the overall horizontal width of the strain gauge 2104. Accordingly, the strain gauge 2104 may ultimately measure the force 2101 exerted on the output shaft 2102.

In some embodiments, the assembly may incorporate a device to measure the orientation of instrument device manipulator 1703, such as an inclinometer or accelerometer. In combination with the strain gauges, measurements from the device may be used to calibrate readings from the strain gauges, since strain gauges may be sensitive to gravitational load effects resulting from their orientation relative to ground. For example, if instrument device manipulator 1703 is oriented on its side, the weight of the drive unit may create strain on the motor mount which may be transmitted to the strain gauge, even though the strain may not result from strain on the output shafts.

In some embodiments, the output signals from the strain gauge circuit boards may be coupled to another circuit board for processing control signals. In some embodiments, power signals are routed to the drive units on another circuit board from that of processing control signals.

As discussed earlier, the motors in drive units 1801, 1802, 1803, and 1804 ultimately drive output shafts, such as output shafts 1705, 1706, 1707, and 1708. In some embodiments, the output shafts may be augmented using a sterile barrier to prevent fluid ingress into the instrument device manipulator 1703. In some embodiments, the barrier may make use of a labyrinth seal (1905 from FIG. 19A) around the output shafts to prevent fluid ingress. In some embodiments, the distal end of the gear head shafts may be covered with output shafts in order to transmit torque to a tool. In some embodiments, the output shafts may be clad in a steel cap to reduce magnetic conductance. In some embodiments, the output shafts may be clamped to the gear head shafts to assist transfer of torque.

Instrument device mechanism 1703 may also be covered in a shell or skin, such as outer shell/skin 1901. In addition to being aesthetically pleasing, the shell provides fluid ingress protection during operation, such as during medical procedures. In some embodiments, the shell may be constructed using cast urethane for electromagnetic shielding, electromagnetic compatibility, and electrostatic discharge protection.

In an embodiment of the present invention, each of those output shafts in individually tension may pull wires in a robotic catheter that makes use of steerable catheter technology. Tensile force in the pull wires may be transmitted to the output shafts 1705, 1706, 1707 and 1708 and down to a motor mount, such as motor mounts 1809 and 1811.

Sheath & Endoscope Manufacture.

In the preferred embodiment, the sheath and endoscope devices are constructed using steerable catheter construction methodologies. Traditionally, steerable catheters have been manufactured by braiding wires or fibers, i.e., braid wire, around a process mandrel with pull lumens in a braiding machine, i.e., braider and a polymer jacket applied over the braid wires. During manufacture, a process mandrel would be typically inserted into a feed tube of a braider that was coupled to a braid cone support tube and braid cone holder. Using a puller with a tread, the process mandrel would be advanced through the feed tube. As the process mandrel progressed, it would eventually emerge through a center hole in a nose cone. The nose cone provided a round, smooth shape on which the braid wire from the surrounding horn gears may easily slide around the mandrel during the braiding process. The nose cone was typically held in a position that was fixed axially and radially relative to the braid cone holder using a set screw keyed to the braid cone holder. As the process mandrel was pulled through the nose cone, the horn gears translate and rotate around the mandrel to braid the braid wire around the mandrel in a pre-determined pattern and density.

Figure 22:
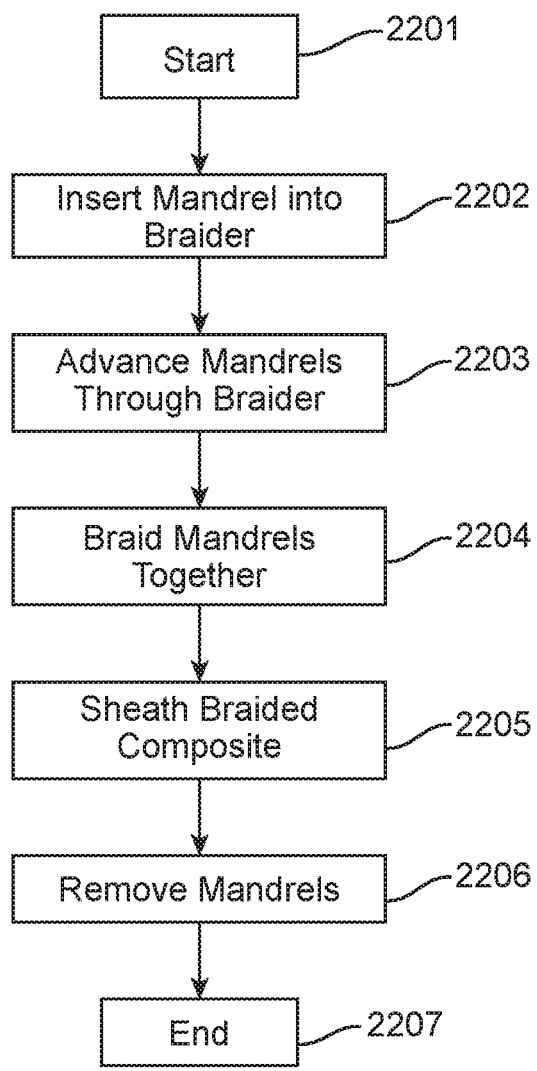
FIG. 22 illustrates a flowchart for a method of constructing a catheter device with helical lumens, in accordance with an embodiment of the present invention.

FIG. 22 illustrates a flowchart for a method of constructing a catheter with helixed lumens, in accordance with an embodiment of the present invention. To start, in step 2201, a main process mandrel may be selected to create a cavity in the catheter for a central lumen that may be used a working channel. Supplemental mandrels may be selected to create cavities in the wall of the catheter for use as control (pull) lumens. The main process mandrel may exhibit larger outer diameters (OD) than the supplemental mandrels to reflect the relative size differential between a working channel and pull lumens. The supplemental mandrels may be constructed a metal or thermoset polymer that may or may not be coated with a lubricious coating, such as PTFE.

In step 2202, the main process mandrel may be inserted into a feed tube of a braider that rotates relative to a fixed braid cone support tube and braid cone holder. Similarly, the supplemental mandrels may also be inserted into the feed tube in parallel fashion to the main process mandrel. In traditional catheter construction, smaller supplemental mandrels are passed through the center of the horn gears for braiding.

In step 2203, using a puller with a tread, the main process mandrel may be advanced through the feed tube. As the main process mandrel progresses, it eventually emerges through a center hole in a nose cone.

Similarly, the supplemental mandrels are advanced through to also emerge through outer holes in the nose cone. This contrasts with traditional catheter construction, where supplemental mandrels are typically advanced through separate feed tubes to emerge from the center of the horn gears.

In step 2204, the main process mandrel and supplemental mandrels are braided together using braid wire as they emerge through the nose cone. The nose cone provides a round, smooth shape on which the braid wire from the surrounding horn gears may easily slide around the main process mandrel during the braiding process. As both the main process mandrel and supplemental mandrels emerge from the nose cone, the nose cone rotates, ensuring that the supplemental mandrels in the outer holes are braided in a spiraled fashion around the main process mandrel. As the main process mandrel and supplemental mandrels are being braided together, the horn gears translate and rotate to lay braid wire around both the main process mandrel and supplemental mandrels at a pre-determined pattern and density.

This method of braiding is significantly different from traditional methods of catheter construction, where the nose cone is typically held in a position that is radially fixed relative to the braid cone holder using a set screw keyed to the braid cone holder. Thus, specialized hardware is required for the braiding process in order to manufacture catheters with helical control lumens.

In step 2205, upon completion of the braided process, a polymer coating or jacket may be sheathed, heated, and bonded to the braiding composite. The polymer coating may also be applied in an over-extrusion or a film-cast process. In step 2206, after bonding, the mandrels may be removed from the braided composite to create a central lumen or working channel (main process mandrel) for camera and light tools, and several control lumens (supplemental mandrels) for steering control. Having removed the mandrels, the braided composite may be finished for completion (2207).

In traditional steerable catheter construction, smaller supplemental mandrels are passed through the center of the horn gears for braiding onto the main process mandrel. The supplemental mandrels, sometimes constructed from Teflon-coated polyimide, may be braided onto the main process mandrel as it is pulled through the nose cone. Alternatively, it is known in the art that the supplemental mandrels may be passed through small holes in the nose cone that surround the center hole. As the main process mandrel is pulled through the nose cone, the smaller, supplemental mandrels may be braided to the main process mandrel as they are pulled from the nose cone.

In order to hold the supplemental mandrels in place, a second layer of braid wire is typically laid onto the main process mandrel after applying the supplemental mandrels. Upon completion of the braided process, a polymer coating or jacket may be sheathed, heated, and bonded to the braiding composite. After bonding, the mandrels are typically removed from the braided composite to create a central lumen (main process mandrel) for camera and light tools, and several control lumens (supplemental mandrels) for steering control. This method of manufacture results in endoscopes with control lumens that are longitudinally parallel to the neutral axis. As discussed earlier, catheter-like endoscopes with tension on tendons in longitudinally parallel lumens exhibit muscling and curve alignment phenomena.

Figure 23:
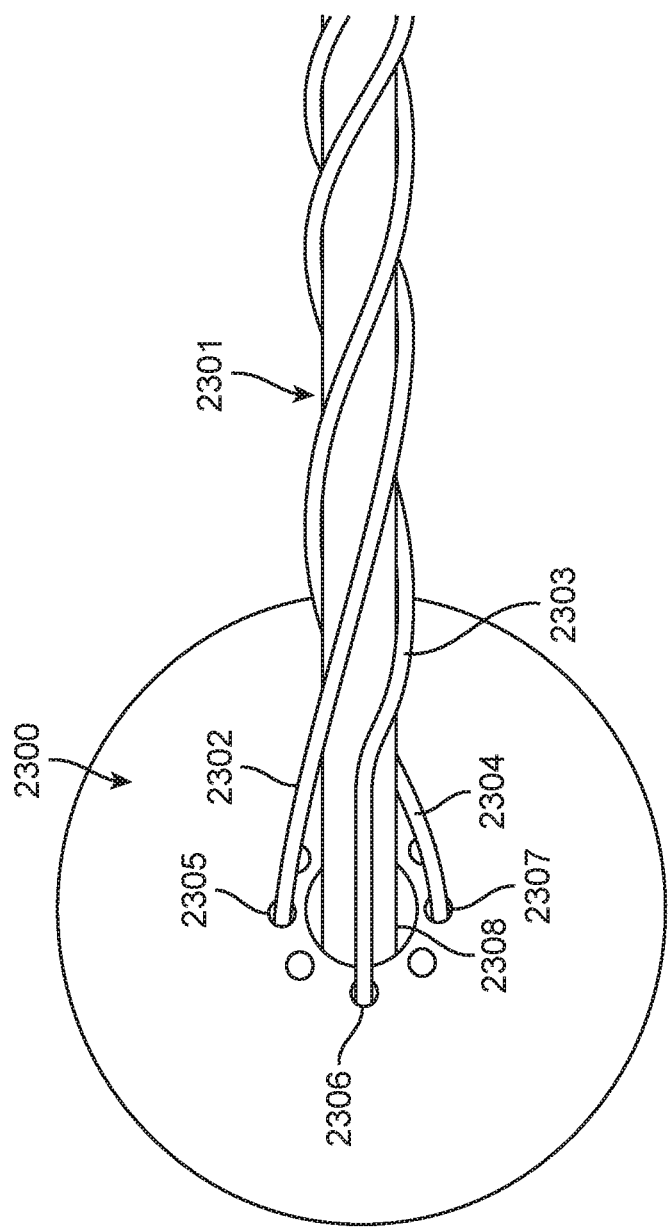
FIG. 23 illustrates a specialized nose cone for manufacturing flexible endoscopic devices, in accordance with an embodiment of the present invention.

Accordingly, specialized hardware is required for the braiding process in order to manufacture catheter-like endoscopes with helixed control lumens. One such piece of hardware is a specialized rotating nose cone that is fixedly coupled to a rotating feed tube, or "hypotube" in some embodiments. FIG. 23 illustrates a specialized nose cone for manufacturing helical lumens in a flexible sheath, catheter, and/or endoscope, in accordance with an embodiment of the present invention. Rotating the nose cone 2300 at the same time that the main process mandrel 2301 is pulled through the nose cone 2300 allows for supplemental mandrels 2302, 2303, and 2304 to be applied in a helical pattern around the mandrel 2301 through supplemental holes 2305, 2306, and 2307 respectively that surround the center hole 2308, similar to how the horn gears braid the braid wire around the main process mandrel 2301.

FIG. 24 illustrates a system for manufacturing a flexible sheath and endoscope in accordance with an embodiment of the present invention. In system 2400, the nose cone 2401 may be fixedly coupled to a rotating feed tube 2402 using a set screw that holds the nose cone 2401 in a fixed position relative to the feed tube 2402. Thus, nose cone 2401 rotates as the feed tube 2402 rotates. In contrast, traditional systems typically use a set screw to fixedly couple the nose cone 2401 to the braid cone support holder 2405, which does not rotate. The center hole 2403 of the nose cone 2401 may be aligned with the rotating feed tube 2402 in order to smoothly pull the main process mandrel 2404 through both structures. In contrast, traditional systems used a set screw to fixed couple the nose cone 2401 to the braid cone support holder 2405. In some embodiments, the rotating feed tube 2402 has an outside diameter less than the interior diameter of the braid cone support tube 2406, also known as a mandrel guide tube, and an interior diameter larger than the circumferential space of the center hole 2403 of the nose cone 2401. The rotating feed tube 2402 may generally be large enough for the main process mandrel 2404 and the supplemental mandrels to be passed through to the nose cone 2401 without entanglement. In some embodiments, the rotating feed tube 2402 is long enough to pass through the center of the horn gears of the braider. In some embodiments, the rotating feed tube 2402 may be attached to a mechanism that may hold bobbins of material for the supplemental mandrels that will be passed through the feed tube 2402 to supplemental holes around the nose cone 2401.

In some embodiments, the feed tube 2402 may be attached to a drive mechanism that controls the rate of rotation of the feed tube 2402 and thus the rotation of the nose cone 2401. In some embodiments, the drive mechanism may be a rotating gear 2407. As the braider is braiding the braid wires 2408 around the main process mandrel 2404, the drive mechanism is either geared to the braider itself or independently controlled to vary or hold constant the rate of rotation of the rotating feed tube 2402 and thus the rate of rotation of the nose cone 2401. The rate of rotation and the rate of braiding will govern the pitch of the supplemental mandrels on the main process mandrel 2404. As discussed earlier, this may affect the flexibility, stiffness, and "pushability" of the device.

In another embodiment, varying the circumferential orientation of the pull lumens may change the stiffness of the helixed section of the endoscope. In manufacture, this is achieved by altering the pitch of the supplemental, spiraling mandrels. As the pitch (i.e., the angle off the longitudinal axis) of the mandrels decreases, the bending stiffness of the braided composite increases. Conversely, as the pitch of the supplemental mandrels increases, the bending stiffness decreases. As shown in FIG. 10B, in some embodiments, the pitch of the supplemental mandrels may be varied within the helixed portion (1010). In those embodiments, the bending stiffness of the braided composite may vary even within the helixed portion.

During the braiding process, the braiding machine may be stopped to make alterations to the braided composite. In some embodiments, one alteration may be the addition of straight wires or reinforcement rods. Reinforcement rods may significantly increase the buckling, axial and bending stiffness of a braided laminated composite. Reinforcement rods may be particularly helpful for longer endoscopes which may require specialized anti-buckling construction or manual assistance to reduce the buckling of the device so that it may be inserted into a patient. In some embodiments, the braiding machine may be configured to selectively braid reinforcement rods that may be pulled from holes in the nose cone onto the process mandrel, where the reinforcement rods are captured and held in place by the braid wire. The absence of reinforcement rods in the distal region of the resulting endoscope preserves the device's flexibility in the distal end while increasing the stiffness in the proximal region. This combination of properties makes the resulting endoscope easier for a physician to guide, insert, and push the device into an endolumenal cavity of a patient.

Applying supplemental mandrels onto a main process mandrel using holes in a rotating nose cone provides a number of manufacturing advantages. By using holes in the nose cone, the mandrels are not pushed from the horn gears. Pushing mandrels from the center of the individual horn gears, which are also responsible for weaving the braid wire, results in the mandrels being interwoven with the braid wire, which locks the resulting braid matrix in place longitudinally. This form of construction, known as "zero degree construction," limits the ability of the manufacturer to adjust the braid matrix for desirable flexibility or hoop strength. In zero degree construction, the supplemental mandrel is necessarily confined in an "over-under manner" by the braid, resulting in all clockwise braided braid wire being woven "over" the supplemental mandrels, while all counter-clockwise braided braid wire is woven "under" the supplemental mandrels. As zero degree construction locks the supplemental mandrels in place radially, it is undesirable where varying the pitch of the supplemental mandrel along the main process mandrel is required.

Additionally, use of the horn gears as a pass-through for the supplemental mandrels limits the number of supplemental mandrels that may be applied to the main process mandrel. For example, a sixteen carrier braider can apply up to eight mandrels, a twenty-four carrier braider can only have up to twelve mandrels. In contrast, use of holes in the nose cone allows any number of mandrels to be passed through to the main process mandrel.

In some embodiments, the supplemental mandrels may be applied to the main process mandrel without the benefit of a second, outer layer of braid wire. Instead, the supplemental mandrels may be applied without braid wire. In those embodiments, the bonded/fused polymer jacket may hold the mandrels, and thus lumens in place. Alternatively, in some embodiments, the mandrels may be held in place using a casting around the braided composite. Since the outer braid layer is absent from the manufacturing endoscopic device, the diameter and circumference of the device cross-section is reduced. Alternatively, the supplemental mandrels may be held in place by sleeving a polymer jacket over the process mandrel. In some embodiments, the casting is the same material as the exterior material for the endoscopic device.

In some embodiments, the supplemental mandrels may be braided onto the main process mandrel much like the braid wire. For example, in some embodiments, the supplemental mandrels may be braided using the even numbered horn gears, while held in place by braid wire braided using the odd numbered horn gears. In this way, the supplemental mandrels, and thus the lumens may be woven into the walls of the central lumen. As an added benefit, embodiments manufactured using this means also tend to have lower circumferential area.

Alternatively, in some embodiments, the helixed lumen structures may be manufactured using extruded molds. These molds may generate the helixed lumen structures to create a jacket from PTFE, pebax, polyurethane, and nylon. In some embodiments, the extruded structures may be formed using a mold around a braided mandrel.

In some embodiments, the helical lumen construction may be performed by rotating the main process mandrel as it is being drawn through the braider. By rotating the main process mandrel, instead of the nose cone, the supplemental mandrels may be drawn through either a fixed nose cone or through the center of the horn gears during the braiding process. In this embodiment, the nose cone may be fixedly coupled to the nose cone holder and the main process mandrel is rotated as it drawn through the nose cone.

Construction of sheath 1000 from FIGS. 10A, 10B, and 10C and flexible endoscope 1100 from FIGS. 11A and 11B are substantially the same. Thus, one of skill in the art would understand that the same principles apply to both tools.

Figure 25:
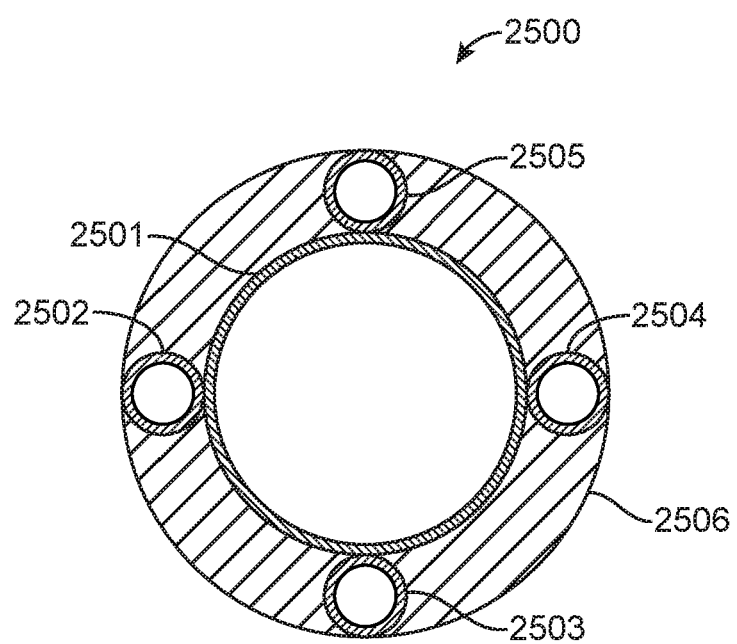
FIG. 25 illustrates a cross-sectional view of a flexible endoscopic device where the pull lumens are arranged symmetrically around the circumference of the device, in accordance with an embodiment of the present invention.

In some embodiments, the helixed lumens may be positioned to be equidistant from each other. FIG. 25 illustrates a cross-sectional view of a flexible endoscopic device where the pull lumens are arranged symmetrically around the circumference of the device, in accordance with an embodiment of the present invention. As shown in FIG. 25, device 2500 has a central working channel 2501, four pull lumens (2502, 2503, 2504, and 2505) spaced symmetrically around the working channel 2501 and within the outer jacket 2506.

In some embodiments, though helixed, the lumens and pull wires may not be distributed evenly or equidistant from each other around the circumference of the sheath and/or flexible endoscope. In some applications, grouping all of the lumens and pull wires onto the same side or hemispheric region (e.g., top vs. bottom hemisphere) of the sheath and endoscope allows for a smaller outer diameter.

Figure 26A:
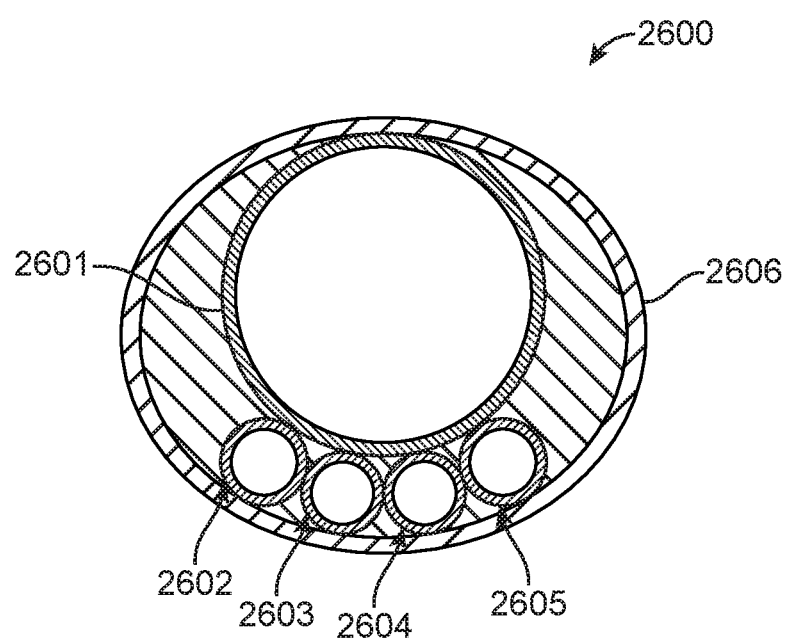
FIG. 26A illustrates a cross-sectional view of a flexible endoscopic device where the pull lumens are not arranged symmetrically around the circumference of the device, in accordance with an embodiment of the present invention.

FIG. 26A illustrates a cross-sectional view of a flexible endoscopic device where the pull lumens are not arranged symmetrically around the circumference of the device, in accordance with an embodiment of the present invention. Similar to device 2500 of FIG. 25, device 2600 has a working channel 2601, four pull lumens 2602, 2603, 2604, and 2605, and an outer jacket 2606. In some embodiments, the working channel may be created by a hollow tube created from a flexible metal alloy, such as nitinol.

Rather than being arranged equidistant from each other, however, pull lumens 2602, 2603, 2604, and 2605 are grouped together to reduce the outside diameter of the device, as shown by the circumference of the outer jacket 2606. Even though the pull lumens are not equidistant from each other around the circumference of the working channel 2601, helixing the pull lumens in the arrangement shown in device 2600 still exhibits the advantages of helixing, e.g., avoiding muscling or curve alignment phenomena. Although the pull lumens of device 2600 are arranged adjacent to each other around working channel 2601, other embodiments may be arranged in a different pattern such as spaced out within same hemisphere, clustered together, or another arrangement. The jacket 2606 may be created from plastic or any other material that may be stretched, bonded or melted during the manufacture of device 2600.

Figure 26B:
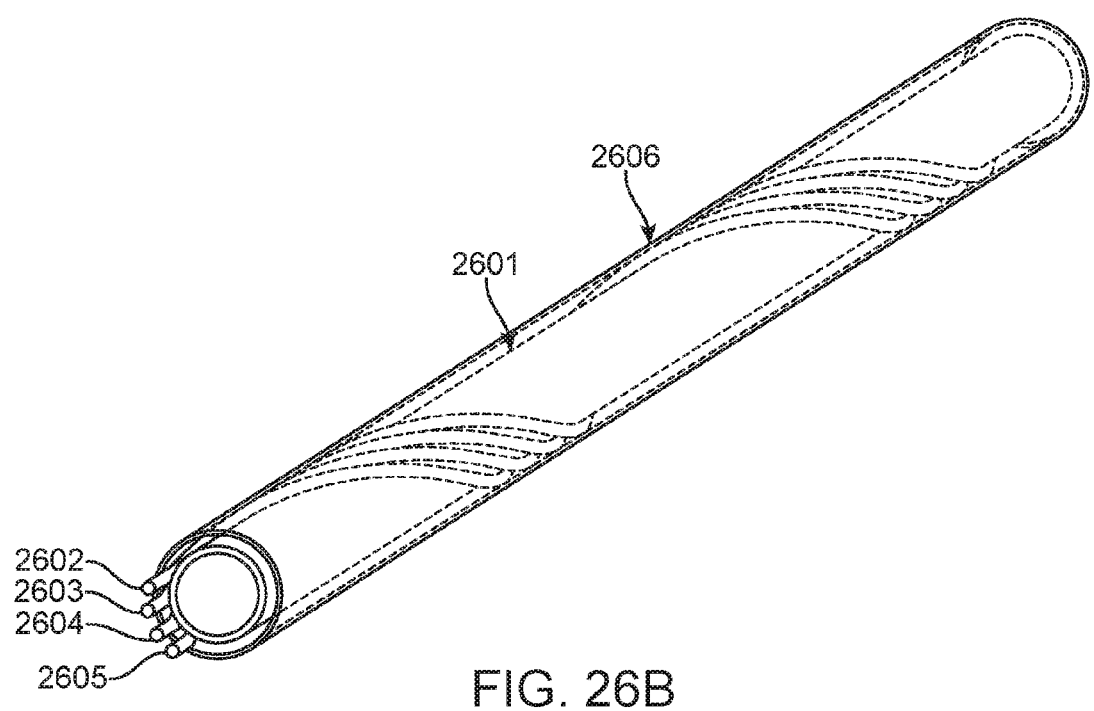
FIG. 26B illustrates an isometric view of the flexible endoscopic device in FIG. 26A, in accordance with an embodiment of the present invention.

FIG. 26B illustrates an isometric view of the flexible endoscopic device 2600 disclosed in FIG. 26A, in accordance with an embodiment of the present invention. As shown in the isometric view of FIG. 26B, pull lumens 2602, 2603, 2604, and 2605 helix around the working channel 2601. In some embodiments, the pitch of the helixed pull lumens may be varied in order to obtain desired properties, such as stiffness and bending flexibility, from device 2600.

Figure 27:
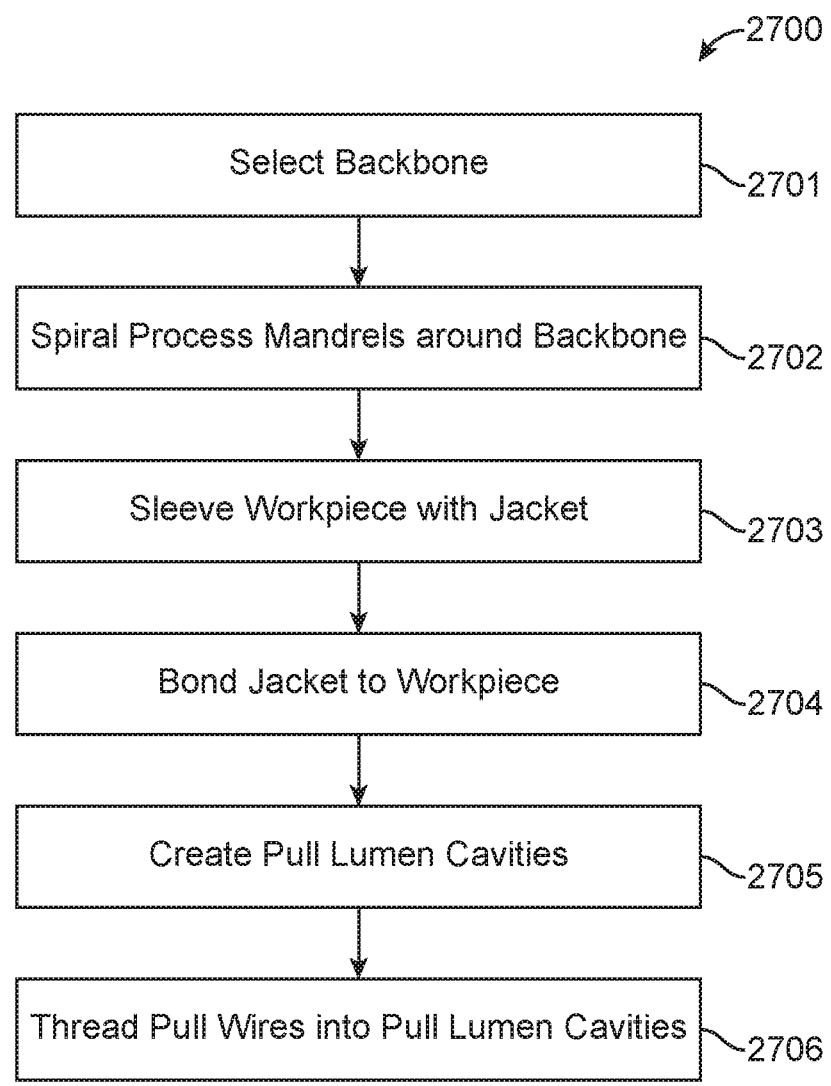
FIG. 27 illustrates a flow diagram for a method for manufacturing the flexible endoscopic device in FIGS. 26A and 26B, in accordance with an embodiment of the present invention.

FIG. 27 illustrates a flow diagram for a method for manufacturing device 2600, in accordance with an embodiment of the present invention. As shown in step 2701, the manufacturing process 2700 begins with selecting a backbone for the workpiece. In some embodiments, the backbone may be a hollow tube, such as a hypodermic "hypo" tube or a nitinol tube. A person skilled in the art would recognize that tube materials may be preferred since tubular structures simultaneously exhibit axial stiffness and low bending stiffness. Additionally, the tube provides for a working channel through which useful tools and cables may be inserted, such as optics, aspiration, irrigation, and controls. In some embodiments, the backbone may be a solid rod, such as for use as an articulable guidewire.

Following the selection of a backbone, in step 2702, process mandrels (one or more) may then be spiraled around the backbone at the desired pitch. In some embodiments, the process mandrels may be coated with polytetrafluoroethylene (PTFE) for easy removal during step 2705. The pitch of the spiraled mandrels may be fixed or dynamic, allowing for the different bending and stiffness properties depending on the application. The lower the pitch, i.e., longitudinally parallel to the neutral axis of the backbone, the lower the axial compression under tension, while also exhibiting increased muscling and curve alignment phenomena. Higher pitch spiraling generally exhibits reduced muscling and curve alignment phenomena at the cost of increased axial compression under tension.

In step 2703, the resulting workpiece, comprising of a backbone and at least one spiraled mandrel, may then be sheathed or covered in a "jacket". In some embodiments, the jacket is a simple extruded tube or sheath. Selection of the means of the sheathing may be critical; as sheathing may inadvertently alter the pitch of the process mandrels around the backbone. In some embodiments, the "sheathing" process may be accomplished by casting, deposition, overextrusion, or any other means that would be known in the art.

In step 2704, if not already bonded from the sheathing process, the jacket may be bonded to the workpiece. This may involve melting, molding or bonding the to the workpiece using any number of processes known to one skilled in the art. Once bonded, the jacket may then hold the process mandrels in place.

In step 2705, once the bonding process is complete, the spiraled process mandrels may be removed to create helixed pull lumen cavities, i.e., lumens, that run longitudinally along the length of the workpiece. In step 2706, following removal of the mandrels, the pull wires may be threaded into the remaining cavities. In operation, the pull wires may then be used to facilitate pull wires for articulating the endoscopic device.

As method 2700 does not make use of braiding, it provides for the construction of workpieces and devices with relatively small outer diameters, which may be appropriate for reaching areas requiring small instruments, e.g., microsurgical applications. While the method of manufacture previously discussed may be applied to devices of varying sizes and outer diameters, the preferred embodiments generally have an outer diameter of less than 2 mm.

Integration of the resulting workpiece into an endoscopic device may be accomplished by melting, molding, bonding, and casting the workpiece jacket to the outer jacket of other components, such as a flexure or tool tip. In some embodiments, the backbone may include structure for an adjoining microsurgical flexure tool, such as ribbing for an increased bend radius and longitudinally-aligned cavities for tools and control wires.

Endolumenal Navigation.

In an embodiment of the present invention, navigation of the robotic catheter through anatomical lumens may involve use of computer-generated three-dimensional maps based on a collection of two-dimensional images created by low dose computerized tomography (CT) scans. Two-dimensional CT scans, each representing a cutaway view of the patient's internal anatomy, may be collected during pre-operative procedures. These scans may be analyzed to determine cavities and anatomical spaces within the patient, such as branches of a lung or the path of a urethra.

Having been analyzed to determine the relevant anatomical spaces within the patient, the spaces may be expressed as lumens with centerline coordinates, i.e., coordinates representing the center of the lumen, in three-dimensional space. The volume of those cavities may be represented as a specific measurement of diameter distance at each centerline coordinate. By tracking the centerline and the corresponding diameter distance measurements, a computer-generated model of a three-dimensional lumen may be generated. Grid coordinate data may thus be used to express three-dimensional spaces and cavities that represent the patient's anatomy.

Figure 28A:
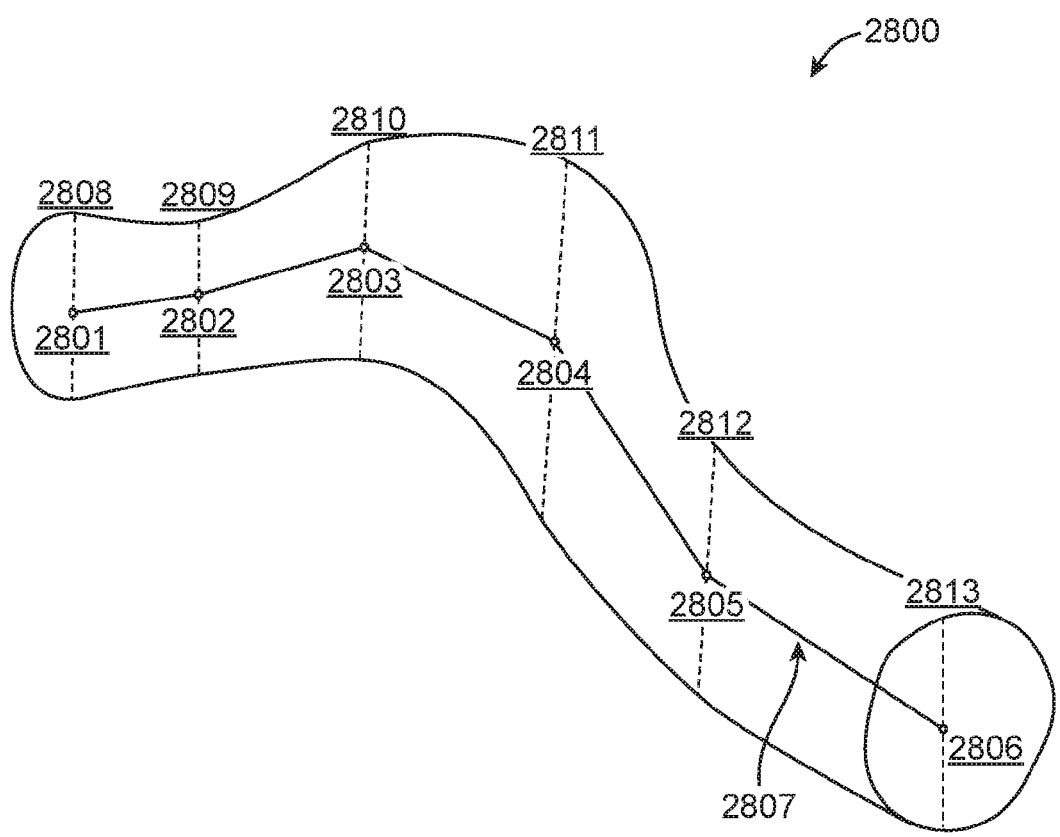
FIGS. 28A and 28B illustrate the relationship between centerline coordinates, diameter measurements and anatomical spaces.
Figure 28B:
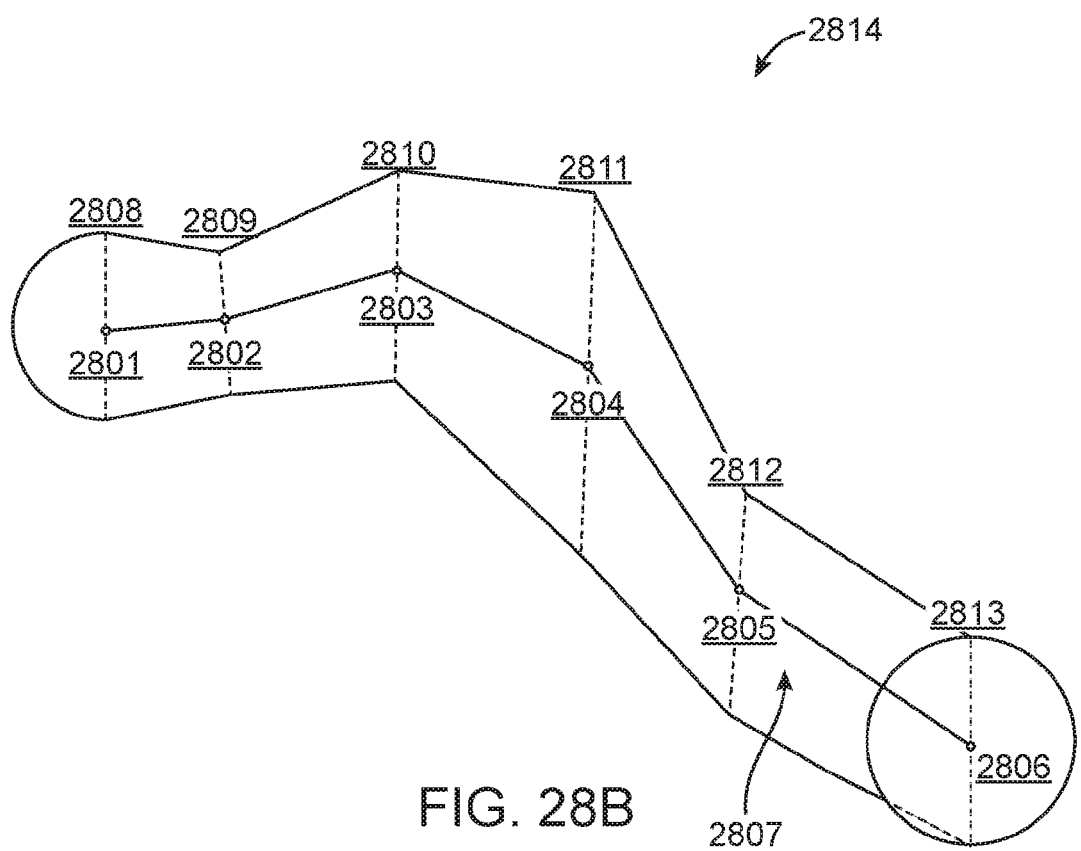

FIGS. 28A and 28B illustrates the relationship between centerline coordinates, diameter measurements and anatomical spaces. In FIG. 28A, anatomical lumen 2800 may be roughly tracked longitudinally by centerline coordinates 2801, 2802, 2803, 2804, 2805, and 2806 where each centerline coordinate roughly approximates the center of the lumen. By connecting those coordinates, as shown by "centerline" 2807, the lumen may be visualized. The volume of the lumen may be further visualized by measuring the diameter of the lumen at each centerline coordinate. Thus 2808, 2809, 2810, 2811, 2812, and 2813 represent the measurements of the lumen 2800 at coordinates 2801, 2802, 2803, 2804, 2805, and 2806.

In FIG. 28B, lumen 2800 may be visualized in three-dimensional space by first locating the centerline coordinates 2801, 2802, 2803, 2804, 2805, and 2806 in three-dimensional space based on centerline 2807. At each centerline coordinate, the lumen diameter may be visualized as a two-dimensional circular space with diameters 2808, 2809, 2810, 2811, 2812, and 2813. By connecting those two-dimensional circular spaces in three-dimensions, lumen 2800 may be approximated as three-dimensional model 2814. More accurate approximations may be determined by increasing the resolution of the centerline coordinates and measurements, i.e., increasing the density of centerline coordinates and measurements for a given lumen or subsection. Centerline coordinates may also include markers to indicate point of interest for the physician, including lesions.

Having expressed, and subsequently generated, a three-dimensional model of the anatomical space, a pre-operative software package may also be used to analyze and derive an optimal navigation path based on the generated module. For example, the software package may derive shortest path to a single lesion (marked by a centerline coordinate) or several lesions. This path may be presented to the operator intra-operatively either in two-dimensions or three-dimensions depending on the operator's preference.

Figure 29:
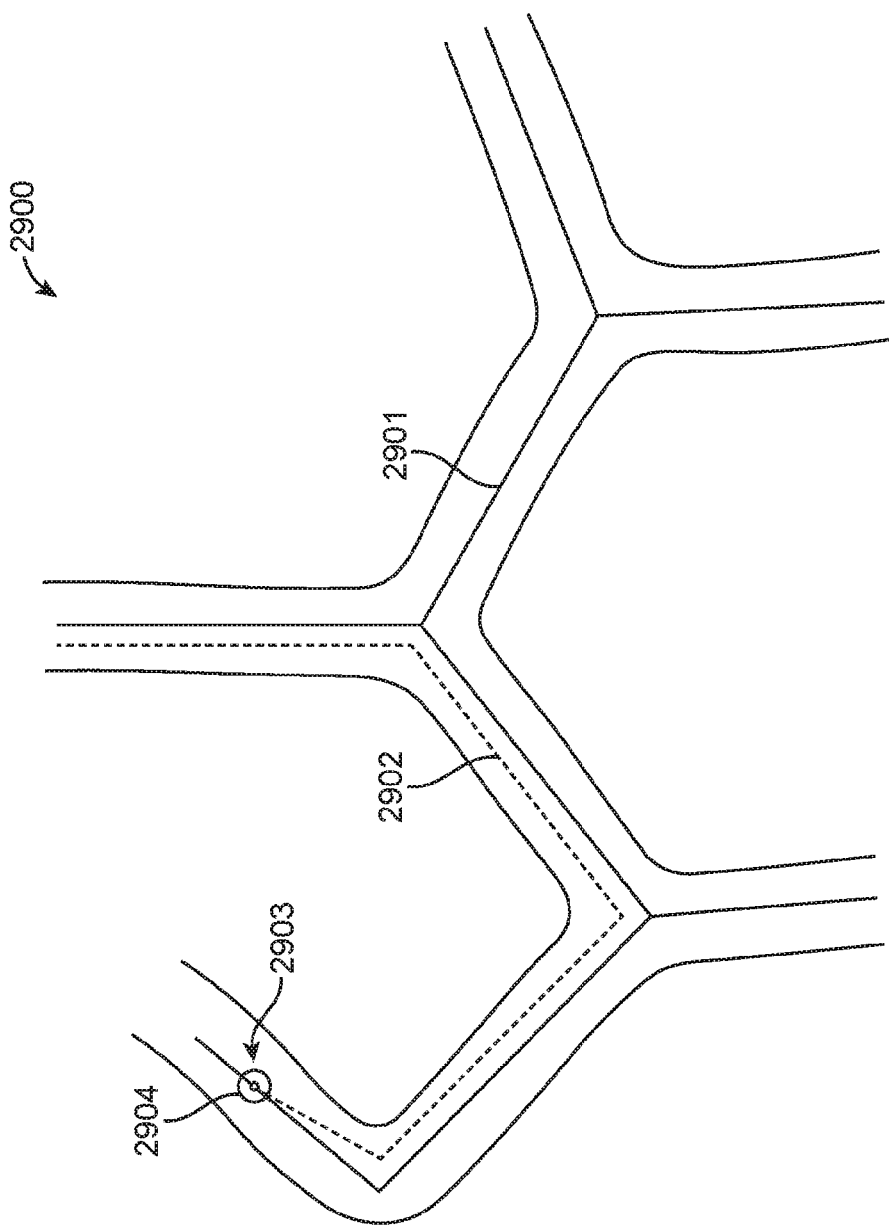
FIG. 29 illustrates a computer-generated three-dimensional model representing an anatomical space, in accordance with an embodiment of the invention.

FIG. 29 illustrates a computer-generated three-dimensional model representing an anatomical space, in accordance with an embodiment of the invention. As discussed earlier, model 2900 may be generated using centerline 2901 that was obtained by reviewing CT scans that were performed preoperatively. In some embodiments, computer software may be able to map the optimum path 2902 for the catheter system to access an operative site 2903 within model 2900, and thus the corresponding anatomical space. In some embodiments, the operative site 2903 may be linked to an individual centerline coordinate 2904, which allows a computer algorithm to topologically search the centerlines of model 2900 for the optimum path 2902 for the catheter system.

Tracking the distal end of the robotic catheter within the patient's anatomy, and mapping that location to placement within a computer model, enhances the navigational capabilities of the catheter system. In order to track the distal working end of the robotic catheter, i.e., "localization" of the working end, a number of approaches may be employed, either individually or in combination.

In a sensor-based approach to localization, a sensor, such as an electromagnetic (EM) tracker, may be coupled to the distal working end of the robotic catheter to provide a real-time indication the progression of the robotic catheter. In EM-based tracking, an EM tracker, embedded in the robotic catheter, measures the variation in the electromagnetic field created by one or more static EM transmitters. The transmitters (or field generators), may be placed close to the patient to creates a low intensity magnetic field. This induces small-currents in sensor coils in the EM tracker, which are correlated to the distance and angle between the sensor and the generator. The electrical signal may then be digitized by an interface unit (on-chip or PCB) and sent via cables/wiring back to the system cart and then to the command module. The data may then be processed to interpret the current data and calculate the precise location and orientation of the sensor relative to the transmitters. Multiple sensors may be used at different locations in the catheter, for instance in leader and sheath in order to calculate the individual positions of those components. Thus, based on readings from an artificially-generated EM field, the EM tracker may detect changes in field strength as it moves through the patient's anatomy.

Figure 30:
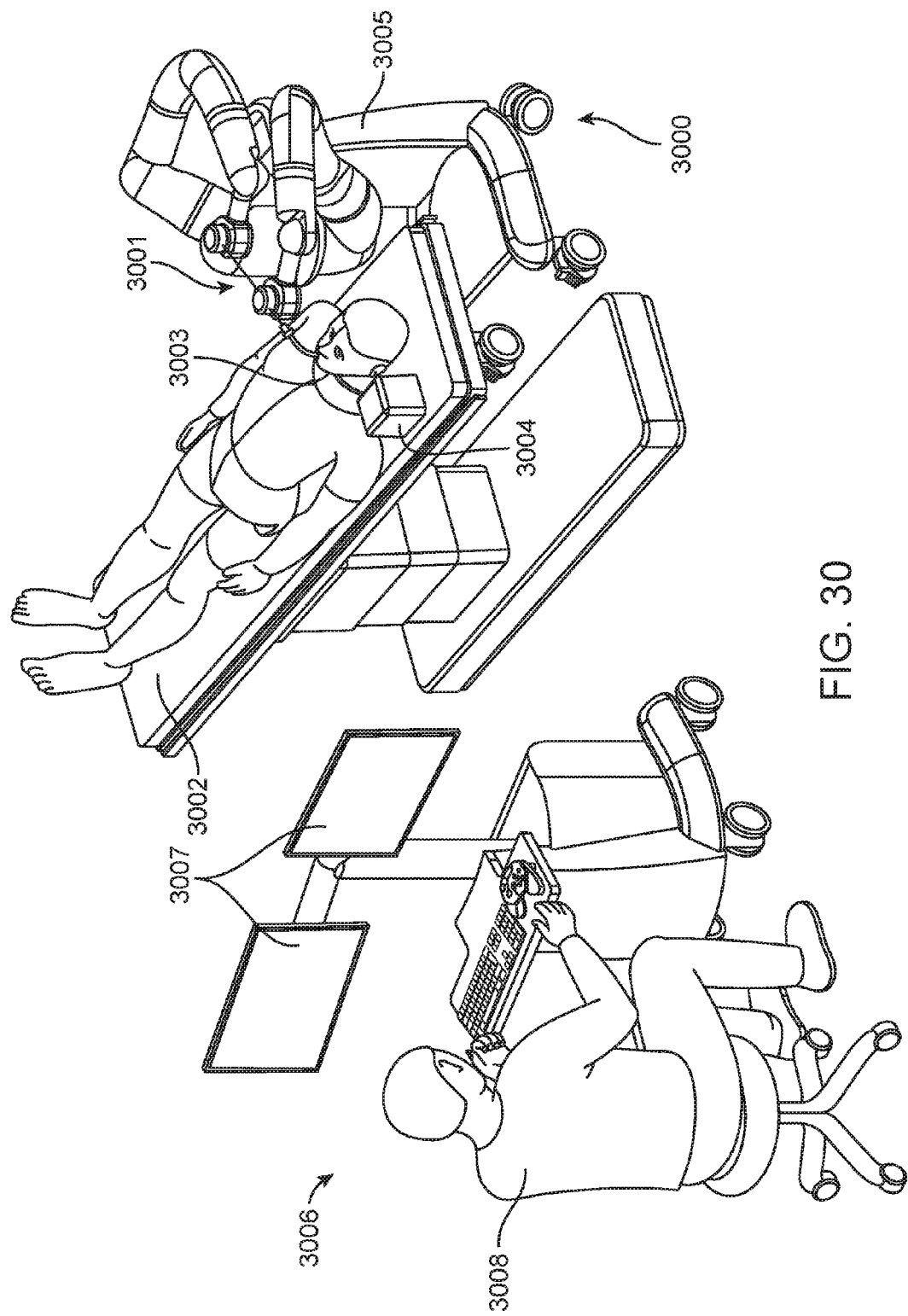
FIG. 30 illustrates a robotic catheter system that makes use of an electromagnetic tracker in combination with an electromagnetic field generator, in accordance with an embodiment in the present invention.

FIG. 30 illustrates a robotic catheter system that makes use of an electromagnetic tracker in combination with an electromagnetic field generator, in accordance with an embodiment in the present invention. As robotic system 3000 drives a robotically driven catheter 3001 into the patient 3002, an electromagnetic (EM) tracker 3003 at the distal end of the robotic catheter 3001 may detect an EM field generated by EM field generator 3004. The EM readings of the EM tracker 3003 may be transmitted down the shaft of the robotic catheter 3001 to the system cart 3005 and to command module 3006 (which contains relevant software modules, a central processing unit, a data bus and memory) for interpretation and analysis. Using the readings from EM tracker 3003, display modules 3007 may display the EM tracker's relative position within a pre-generated three-dimensional model for review by the operator 3008. The embodiments also provide for the use of other types of sensors, such as fiber optic shape sensors. While a variety of sensors may be used for tracking, the choice of sensor may be inherently limited based on (i) the size of the sensor within the robotic catheter and (ii) the cost of manufacturing and integration the sensor into the robotic catheter.

Prior to tracking a sensor through the patient's anatomy, the tracking system may require a process known as "registration," where the system finds the geometric transformation that aligns a single object between different coordinate systems. For instance, a specific anatomical site on a patient has two different representations in the CT model coordinates and in the EM sensor coordinates. To be able to establish consistency and common language between these coordinate systems, the system needs to find the transformation that links these two representations, i.e., registration. In other words, the position of the EM tracker relative to the position of the EM field generator may be mapped to a three-dimensional coordinate system to isolate a location in a corresponding three-dimensional model.

Figure 31:
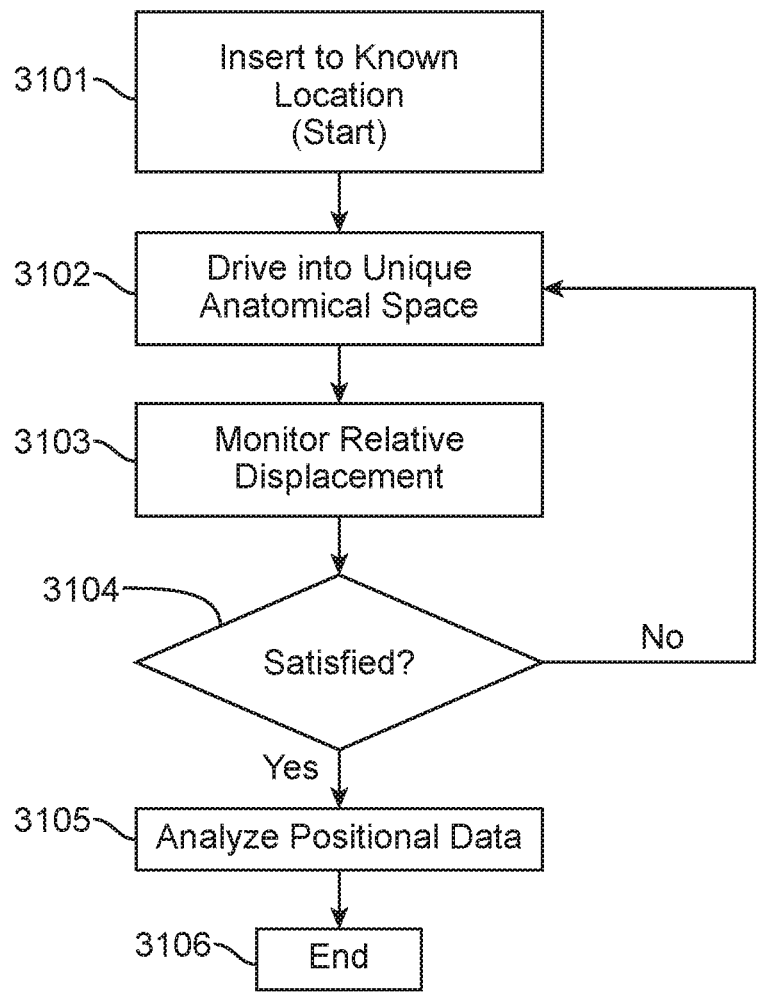
FIG. 31 illustrates a flow diagram for the steps for registration, in accordance with an embodiment of the present invention.

In some embodiments, registration may be performed in several steps. FIG. 31 illustrates a flow diagram for a registration process, in accordance with an embodiment of the present invention. To start, in step 3101, the operator must first position the working end of the robotic catheter at a known starting location. This may involve using video imagery data from the catheter camera to confirm the starting location. Initial positioning may be accomplished by identifying anatomical features through a camera located at the working end of the catheter. For example, in bronchoscopy, registration may be performed by locating the base of the trachea, distinguished by locating the two main bronchial tubes for the left and right lung. This location may be ascertained using video images received by the camera in the distal end of the catheter. In some embodiments, the video data may be compared to different cross sectional views of a pre-generated computer model of the patient's anatomy. By sorting through cross-sectional views, the system may identify the location associated with the cross-section with the smallest amount of differences, or "errors," to find the "match."

In step 3102, the operator may "drive" or "extend" the robotic catheter into unique anatomical spaces that have already been mapped. For example, in bronchoscopy, the operator may drive the catheter down unique bronchial paths from the base of the trachea. Because the base of the trachea splits into two bronchial tubes, an operator may drive the robotic catheter into one tube and track the working end of the robotic catheter using an EM tracker.

In step 3103, the operator monitors the relative travel of the robotic catheter. Monitoring of the robotic catheter may make use of either the EM tracker or fluoroscopy to determine relative movement of the robotic catheter. Evaluation of the relative displacement of the working end of the robotic catheter may be compared the computer model generated from pre-operative CT scan data. In some embodiments, the relative movement may be matched with centerlines in the computer model, where the transformation matrix leads to the least error is the correct registration. In some embodiments, the system and operator may track insertion data (discussed below) and orientation data from an accelerometer and/or gyroscope (discussed below).

In step 3104, the operator may decide to drive into more anatomical spaces (3102) and collect more locational information (3103) prior to comparing and analyzing the positional data. For example, in bronchoscopy, the operator retract the catheter from one bronchial tube back the tracheal tube and drive the catheter into another bronchial tube in order to collect more positional data. Once the operator is satisfied, the operator may stop driving (3102) and monitoring positional data (3103) and proceed to process the data.

In step 3105, the system may analyze the collected positional data and compare the data to pre-generated computer models to register the displacement of the catheter within patient's anatomy to the model. Therefore, by comparing the movement in the patient's anatomy to the three-dimensional model of the patient's anatomy, the system may be able to register the tracker relative to both spaces—three-dimensional computer model vs. patient anatomical space. After analysis, the registration process may be complete (3106).

In some cases, it may be necessary to perform a "roll registration" in order to confirm the orientation of the robotic catheter. This may be particularly important in step 3101 prior to driving into un-registered anatomical spaces. In bronchoscopy, proper vertical orientation ensures that the operator may distinguish between the right and left bronchi. For example within the base of the trachea, images of the left and right bronchi may appear very similar regardless of whether the camera is oriented at zero degrees or one-hundred eighty degrees. Roll registration may also be important because the kinematics of the robotic catheter typically results in a slight rotation during tortuous navigation within a patient.

Roll registration may be important at the operative site when the working channel may be occupied by the sensor. For example, in embodiments with only a single working channel, upon reaching the operative site, the physician may need to remove the EM tracker from the robotic catheter in order to make use of another tool, such as a grasper or forceps. Upon removal, however, the system may lose its localization capabilities without the EM tracker. Thus, when ready to leave the operative region, insertion of the EM tracker may require that the roll registration be again performed to ensure proper orientation.

In some embodiments, the rotation of the robotic catheter may be tracked using an accelerometer mounted within the distal working end of the device. Use of an accelerometer to detect gravitational forces on the catheter provides information regarding the location of the robotic catheter relative to the ground. The location of the ground relative to the catheter may be used to solve certain ambiguities. In bronchoscopy, for example, knowing the orientation (0 or 180 degrees) of the distal camera of the catheter would help determine the appropriate bronchial branch at the start. During navigation, data from the accelerometer to track the direction of gravity, and thus orientation, may also be used to auto-correct the camera image displayed on the control console, ensuring that the displayed image is always oriented vertically.

In a preferred embodiment, a 3-axis MEMS-based sensor chip with an accelerometer may be coupled near the tip of the catheter, on the same printed circuit board as the digital camera. The accelerometer measures the linear acceleration along the three different axes to calculate the velocity and direction of the catheter tip. It accelerometer also measures the direction of gravity and thus provides absolute information about the orientation of the catheter. The accelerometer readings re be transmitted using digital or analog signals through a communication protocol like I2C. The signal may be transmitted through wiring to the proximal end of the catheter and from there to the system cart and command module for processing.

In a three-axis sensor, the accelerometer may be able to determine location of the ground relative to the catheter. If the catheter does not roll or bend up to ninety degrees, a two axis accelerometer could be also be useful. Alternatively, a one-axis sensor may be useful if the axis of the accelerometer remains perpendicular to the direction of gravity, i.e., perpendicular to the ground. Alternatively, a gyroscope may be used to measure the rate of rotation, which may then be used to calculate the articulation of the catheter.

Some embodiments make use of an EM tracker in combination with the accelerometer to supplement any orientation readings from the accelerometer. In some embodiments, use of fluoroscopy to track the robotic catheter may also supplement the registration process. As known in the art, fluoroscopy is an imaging technique that uses X-rays to obtain real-time moving images of the internal structures of a patient through the use of a fluoroscope. Two-dimensional scans generated by fluoroscopy may assist with localization in certain situations, e.g., identifying the relevant bronchi.

Tracking using fluoroscopy may be performed using a plurality of radio-opaque markers on the catheter. Many features of the catheter are naturally radio-opaque to x-rays, including the camera head, the control ring and pull wires; thus, the marker location together with the metallic components of the catheter may be used to obtain a three-dimensional transformation matrix. Once registration has happened, visual images detecting branch locations may be precisely correlated to the three-dimensional model. In addition, the full branch length and branch location in 3D can be measured and enhanced in the map.

In contrast to a sensor-based approach, vision-based tracking involves using images generated by a distally-mounted camera to determine the location of the robotic catheter. For example, in bronchoscopy, feature tracking algorithms may be used to identify circular geometries corresponding to bronchial paths and track the change of those geometries from image to image. By tracking the direction of those features as they move from image to image, the system may be able to determine which branch was selected, as well as the relative rotational and translational motion of the camera. Use of a topological map of the bronchial paths may further enhance vision-based algorithms.

In addition to feature based tracking, image processing techniques such as optical flow may also be used to identify branches in the airway topology in bronchoscopy. Optical flow is the displacement of image pixels from one image to the next in a video sequence. With respect to bronchoscopy, optical flow may be used to estimate the movement of the tip of the scope based on changes in the camera images received at the tip of the scope. Specifically, in a series of video frames, each frame may be analyzed to detect translation of the pixels from one frame to the next. For example, if the pixels in a given frame appear to translate to the left in the next frame, the algorithm would infer that the camera, and in turn the tip of the scope, moved to the right. Through comparing many frames over many iterations, movement (and thus location) of the scope may be determined.

Where stereoscopic image capture—as opposed to monocular image capture—is available, optical flow techniques may also be used to complement the pre-existing three-dimensional model of the anatomic region. Using stereoscopic image capture, the depth of the pixels in the two-dimensional captured images may be determined to build a three-dimensional map of objects in the camera view. Extrapolating to travel within an anatomical lumen, this technique enables the system to develop three-dimensional maps of the local surroundings around the catheter while navigating in inside the patient's anatomy. These maps may be used to extend the pre-determined three-dimensional computer models where the models either are missing data or of low quality. In addition to a stereoscopic camera apparatus, depth sensors or specific lighting configurations and image capture techniques—such as RGB-D sensors or structure lighting—may need to be used.

Regardless of tracking method—either sensor-based or vision-based—tracking may be improved by using data from the robotic catheter itself. For example, in robotic catheter 200 from FIG. 2A, the relative insertion length of sheath 201 and leader 205 may be measured from a known, starting position within the trachea (in the case of bronchoscopy). Using relative insertion length and the centerlines of a three-dimensional model of the patient's bronchial tree, the system may giving a rough estimation of the location of the working end after determining whether the robotic catheter is located in a branch and the distance traveled down that branch. Other control information from the robotic catheter may also be used, such as catheter device articulation, roll, or pitch and yaw.

Real-time imaging based on different imaging modalities would further enhance navigation, particularly at the operative site. Even though tracking may assist with rough navigation to the operative site, additional modalities may be useful when more precise handling is necessary, such when attempting to biopsy a lesion. Imaging tools such as fluorescence imaging, near infrared imaging, oxygen sensors, molecular biomarker images, and contrast dye imaging may help pinpoint the exact coordinates of the lesion in the computer model, and thus assist with operating a biopsy needle at the operative site. In the absence of a precise location, the robotic catheter may be used to biopsy the entire region of the operative site at a known depth, thus ensuring tissue from the lesion is sampled.

In some cases, the segmented CT scans, and thus the resulting computer models, do not show branches at the periphery of the lung (in the context of bronchoscopy). This may be due to insufficient inflation of the airways during a scan, or because the size of the branches is below the resolution of a CT scan (typically on the order of 1 millimeter). In practice, the robotic system may enhance the computer model during the procedure by noting the location and the position and orientation of the unmapped branch. In some embodiments, the topology structure may allow physicians to mark their location and return to that same location in order to examine the periphery branches. In some embodiments, the catheter camera may measure the diameter and shape of the branches based on the capture images, allowing those branches to be mapped based on position and orientation.

Endolumenal Procedures.

Figure 32A:
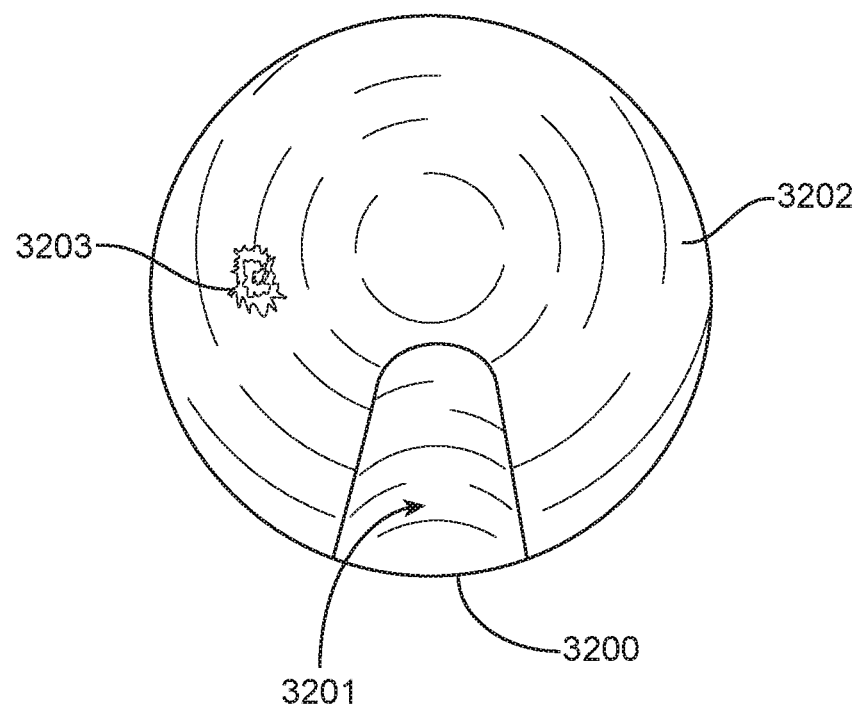
FIG. 32A illustrates the distal end of a robotic catheter within an anatomical lumen, in accordance with an embodiment of the present invention.

FIG. 32A illustrates the distal end of a robotic catheter within an anatomical lumen, in accordance with an embodiment of the present invention. In FIG. 32A, robotic catheter 3200, comprising a shaft 3201 is shown navigating through an anatomical lumen 3202 towards an operative site 3203. During navigation, the shaft 3201 may be unarticulated.

Figure 32B:
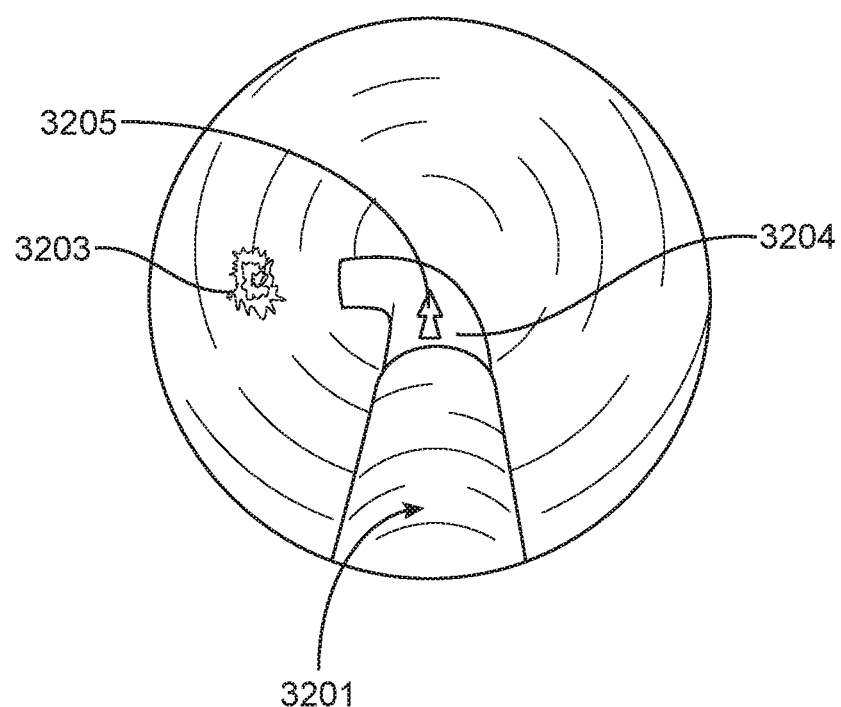
FIG. 32B illustrates the robotic catheter from FIG. 32A in use at an operative site within an anatomical lumen, in accordance with an embodiment of the present invention.

FIG. 32B illustrates the robotic catheter from FIG. 32A in use at an operative site within an anatomical lumen. Having reached the operative site 3203, a distal leader section 3204, longitudinally aligned with the shaft 3201, may be extended from shaft 3201 in the direction marked by arrow 3205. Distal leader section 3204 may also be articulated in order to direct tools towards operative site 3203.

Figure 32C:
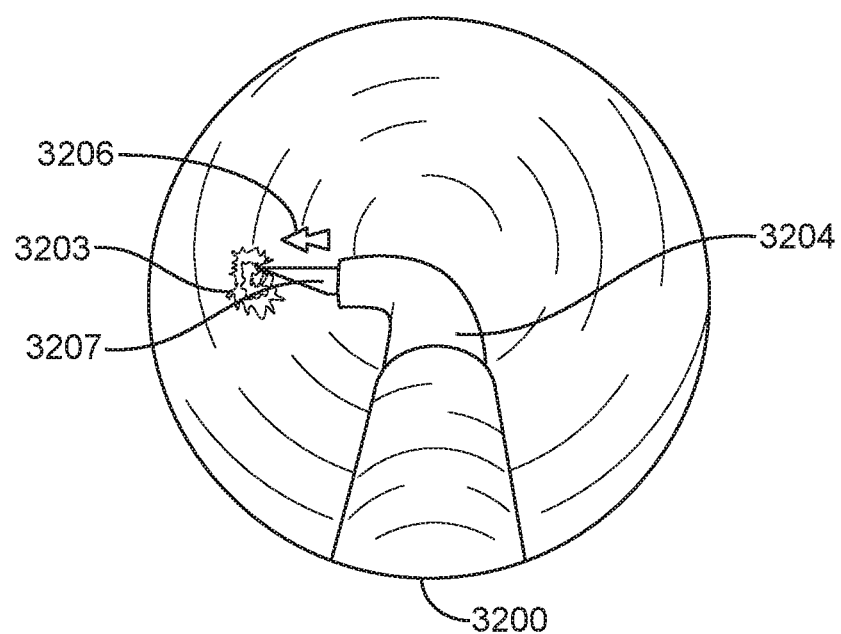
FIG. 32C illustrates the robotic catheter from FIG. 32B in use at an operative site within an anatomical lumen, in accordance with an embodiment of the present invention.

FIG. 32C illustrates the robotic catheter from FIG. 32B in use at an operative site within an anatomical lumen. In cases where the operative site contains a lesion for biopsy, the distal leader section 3204 may articulate in the direction marked by arrow 3206 to convey an aspiration needle 3207 to target a lesion at operative site 3203. In some embodiments, distal leader section 3204 may be articulated to direct biopsy forceps to remove samples of anatomical tissues for purposes of intraoperative evaluation. For purposes of activation of that end effector, robotic catheter 3200 may comprise a tendon operatively coupled to the biopsy forceps.

Figure 33A:
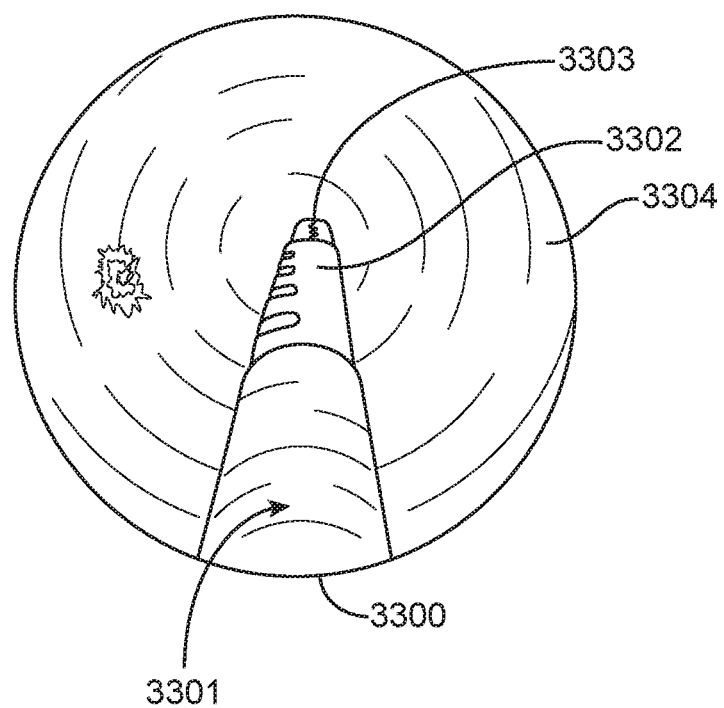
FIG. 33A illustrates a robotic catheter coupled to a distal flexure section within an anatomical lumen, in accordance with an embodiment of the present invention.

FIG. 33A illustrates a robotic catheter coupled to a distal flexure section within an anatomical lumen, in accordance with an embodiment of the present invention. In FIG. 33A, a robotic catheter 3300, comprising a shaft 3301, flexure section 3302, and forceps 3303, is shown navigating through an anatomical lumen 3304 towards an operative site. During navigation, both the shaft 3301 and distal flexure section 3302 may be unarticulated as shown in FIG. 33A. In some embodiments, the flexure section 3302 may be retracted within shaft 3301. The construction, composition, capabilities, and use of flexure section 3302 is disclosed in U.S. patent application Ser. No. 14/201,610, filed Mar. 7, 2014, and U.S. patent application Ser. No. 14/479,095, filed Sep. 5, 2014, the entire contents of which are incorporated by reference.

In some embodiments, the flexure 3302 may be longitudinally-aligned with the shaft 3301. In some embodiments, the flexure 3302 may be deployed through a working channel that is off-axis (neutral axis) of shaft 3301, allowing for the flexure 3302 to operate without obscuring a camera located at the distal end of shaft 3301. This arrangement allows an operator to use a camera to articulate flexure 3302 while shaft 3301 remains stationary.

Similar to other embodiments, different tools, such as forceps 3303, may be deployed through the working channel in flexure section 3302 for use at the distal end of the flexure section 3302. In other scenarios, surgical tools such as graspers, scalpels, needles, and probes may be located at the distal end of the flexure section 3302. In robotic catheter 3300, as in other embodiments, the tool at the distal end of the bending section may be substituted intra-operatively in order to perform multiple treatments in a single procedure.

Figure 33B:
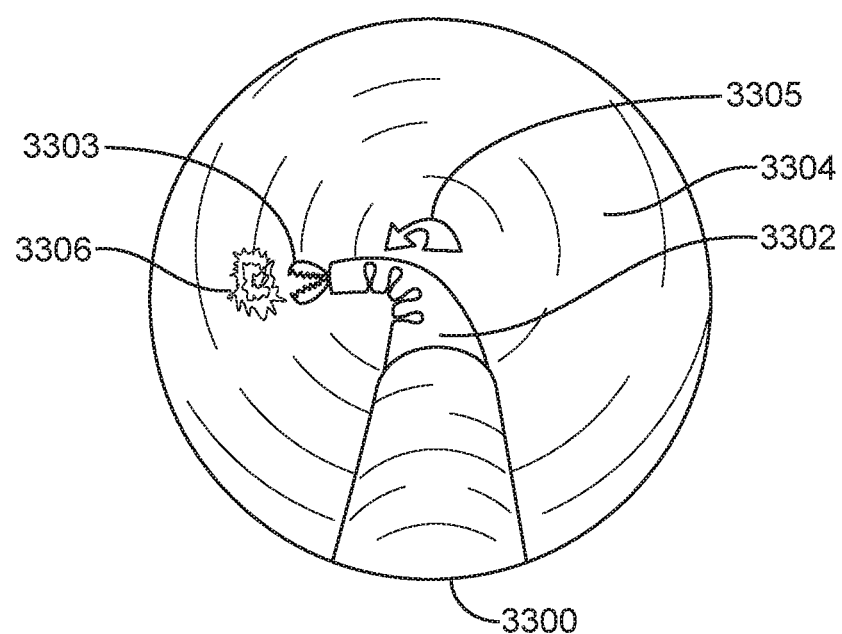
FIG. 33B illustrates a robotic catheter from FIG. 33A with a forceps tool in use at an operative site within an anatomical lumen, in accordance with an embodiment of the present invention.

FIG. 33B illustrates a robotic catheter from FIG. 33A with a forceps tool in use at an operative site within an anatomical lumen, in accordance with an embodiment of the present invention. Navigation of robotic catheter 3300 through anatomical lumen 3304 may be guided by any number of the various navigational technologies discussed above. Once the robotic catheter 3300 has reached its desired location at the operative site 3306, flexure section 3302 may articulate in the direction of arrow 3305 in order to orient forceps 3303 towards operative site 3306. Using forceps 3303, robotic catheter 3300 may take a biopsy of the tissue at the operative site 3306.

Figure 33C:
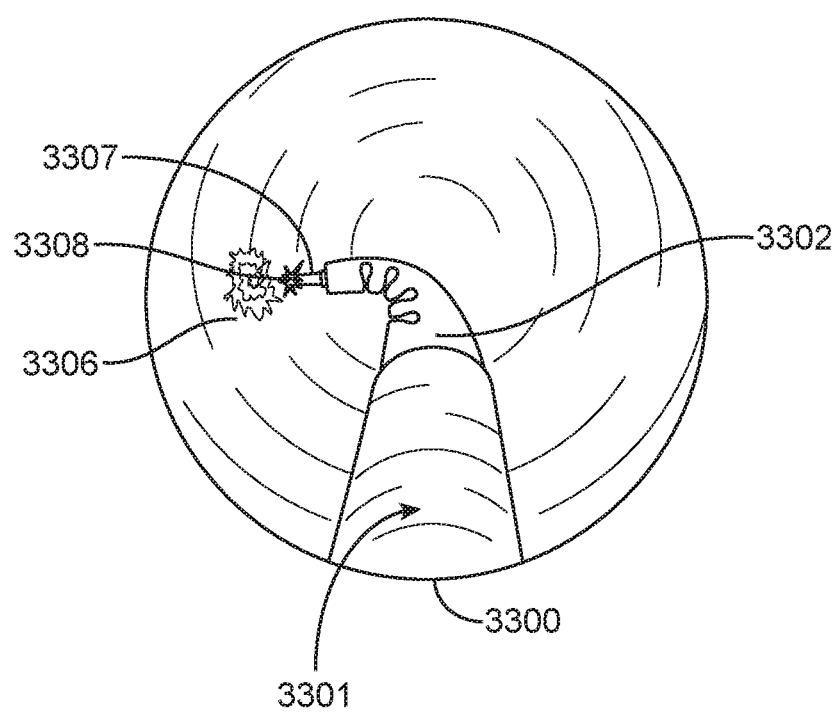
FIG. 33C illustrates a robotic catheter from FIG. 33A with a laser device in use at an operative site within an anatomical lumen, in accordance with an embodiment of the present invention.

FIG. 33C illustrates a robotic catheter from FIG. 33A with a laser device in use at an operative site within an anatomical lumen, in accordance with an embodiment of the present invention. Having reached the operative site 3306, the flexure section 3302 of robotic catheter 3300 may be articulated and a laser tool 3307 may be deployed through the working channel of the shaft 3301 and flexure section 3302. Once deployed, the laser tool 3307 may be directed to operative site 3306 to emit laser radiation 3308 for purposes of tissue ablation, drilling, cutting, piercing, debriding, cutting or accessing non-superficial tissue.

Command Console.

As discussed with respect to system 100 from FIG. 1, an embodiment of the command console allows an operator, i.e., physician, to remotely control the robotic catheter system from an ergonomic position. In the preferred embodiment, the command console utilizes a user interface that both (i) enables the operator to control the robotic catheter, and (ii) displays the navigational environment from an ergonomic position.

Figure 34:
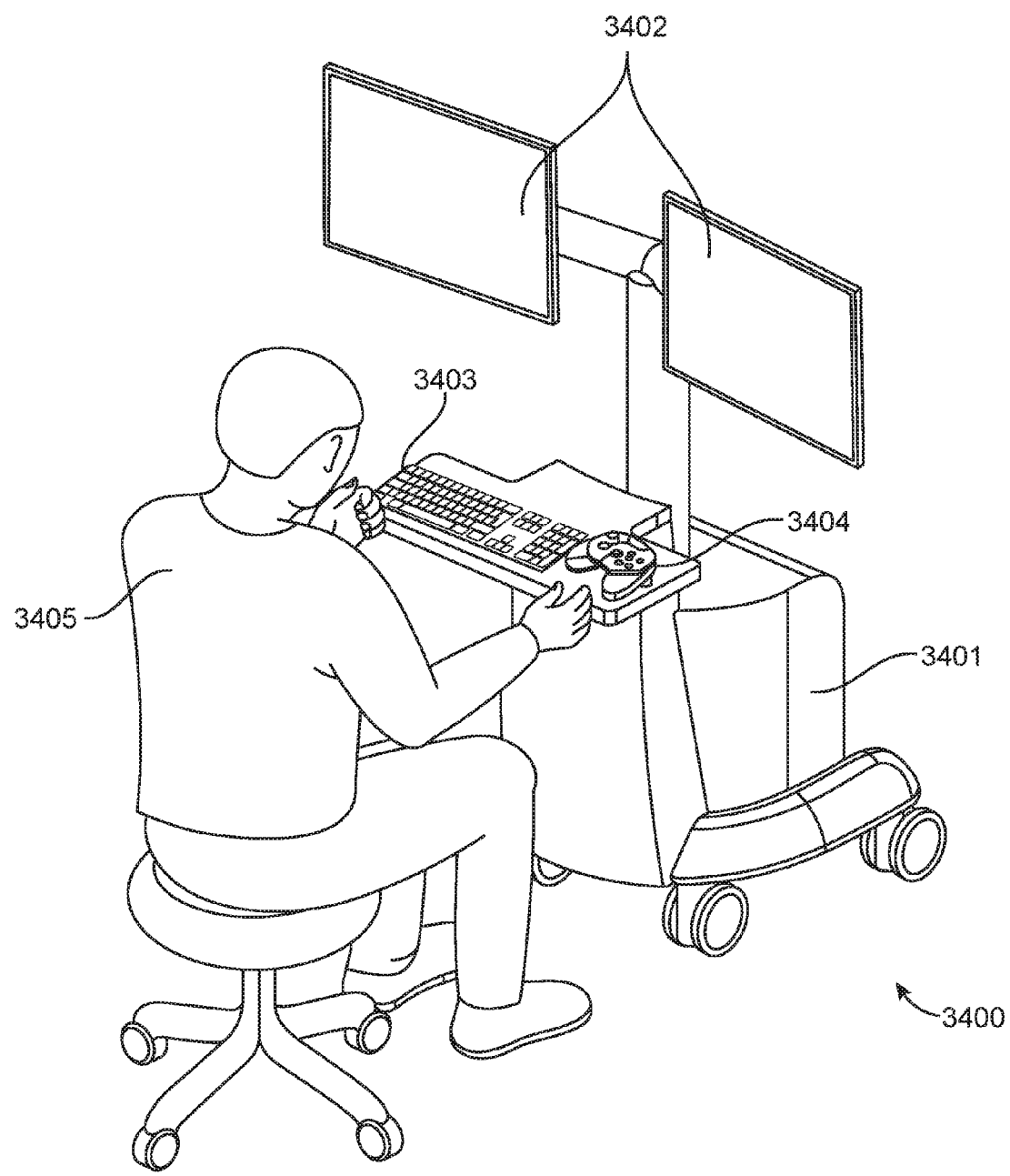
FIG. 34 illustrates a command console for a robotic surgical system, in accordance with an embodiment of the present invention.

FIG. 34 illustrates a command console for a robotic catheter system, in accordance with an embodiment of the present invention. As shown in FIG. 34, command console 3400 may comprise a base 3401, display modules, such as monitors 3402, and control modules, such as keyboard 3403 and joystick 3404. In some embodiments, the command module functionality may be integrated into the system cart with the mechanical arms, such as system cart 101 from system 100 in FIG. 1.

The base 3401 may comprise of a central processing unit, a memory unit, a data bus, and associated data communication ports that are responsible for interpreting and processing signals, such as camera imagery and tracking sensor data, from the robotic catheter. In other embodiments, the burden of interpretation and processing signals may be distributed between the associated system cart and the command console 3400. The base 3401 may also be responsible for interpreting and processing commands and instructions from the operator 3405 through the control modules, such as 3403 and 3404.

The control modules are responsible for capturing the commands of the operator 3405. In addition to the keyboard 3403 and joystick 3404 in FIG. 34, the control modules may comprise other control mechanisms known in the art, including but not limited to computer mice, trackpads, trackballs, control pads, and video game controllers. In some embodiments, hand gestures and finger gestures may also be captured to deliver control signals to the system.

In some embodiments, there may be a variety of control means. For example, control over the robotic catheter may be performed in either a "Velocity mode" or "Position control mode". "Velocity mode" consists of directly controlling pitch and yaw behaviors of the distal end of the robotic catheter based on direct manual control, such as through joystick 3404. For example, right and left motions on joystick 3404 may be mapped to yaw and pitch movement in the distal end of the robotic catheter. Haptic feedback in the joystick may also be used to enhance control in "velocity mode". For example, vibration may be sent back to the joystick 3404 to communicate that the robotic catheter cannot further articulate or roll in a certain direction. Alternatively, pop-up messages and/or audio feedback (e.g., beeping) may also be used to communicate that the robotic catheter has reached maximum articulation or roll.

"Position control mode" consists of identifying a location in a three-dimensional map of the patient and relying on the system to robotically steer the catheter the identified location based on pre-determined computer models. Due to its reliance on a three-dimensional mapping of the patient, position control mode requires accurate mapping of the patient's anatomy.

Without using the command module 3401, the system may also be directly manipulated by manual operators. For example, during system setup, physicians and assistants may move the mechanical arms and robotic catheters to arrange the equipment around the patient and the operating room. During direct manipulation, the system may rely on force feedback and inertia control from human operators to determine the appropriate equipment orientation.

The display modules 3402 may comprise monitors, virtual reality viewing devices, such as goggles or glasses, or other means of display visual information regarding the system and from the camera in the robotic catheter (if any). In some embodiments, the control modules and display modules may be combined, such as in a touchscreen in a tablet or computer device. In a combined module, the operator 3405 may be able to view visual data as well as input commands to the robotic system.

In another embodiment, display modules may display three-dimensional images using a stereoscopic device, such as a visor or goggle arrangement. Using three-dimensional images, the operator may view an "endo view" of the computer model, a virtual environment of the interior of the three-dimensional computer-generated model of the patient's anatomy to approximate the expected location of the device within the patient. By comparing the "endo view" to the actual camera images, the physician may be able to mentally orient himself and confirm that the robotic catheter is in the right location within the patient. This may give the operator a better sense of the anatomical structures around the distal end of the robotic catheter.

In a preferred embodiment, the display modules 3402 may simultaneously display the pre-generated three-dimensional models, the pre-determined optimal navigation paths through the models, and CT scans of the anatomy at the current location of the distal end of the robotic catheter. In some embodiments, a model of the robotic catheter may be displayed with the three-dimensional model of the patient's anatomy, to further clarify the status of the procedure. For example, a lesion may have been identified in a CT scan where a biopsy may be necessary.

During operation, camera means and illumination means at the distal end of the robotic catheter may generate a reference image in the display modules for the operator. Thus, directions in the joystick 3404 causing articulation and rolling of the distal end of the robotic catheter results in an image of the anatomical features directly in front of the distal end. Pointing the joystick 3404 up may raise the pitch of the distal end of the robotic catheter with the camera, while pointing the joystick 3404 down may decrease the pitch.

The display modules 3402 may automatically display different views of the robotic catheter depending on the operators' settings and the particular procedure. For example, if desired, an overhead fluoroscopic view of the catheter may be displayed during the final navigation step as it approached the operative region.

Virtual Rail for Vascular Procedures.

Figure 35A:
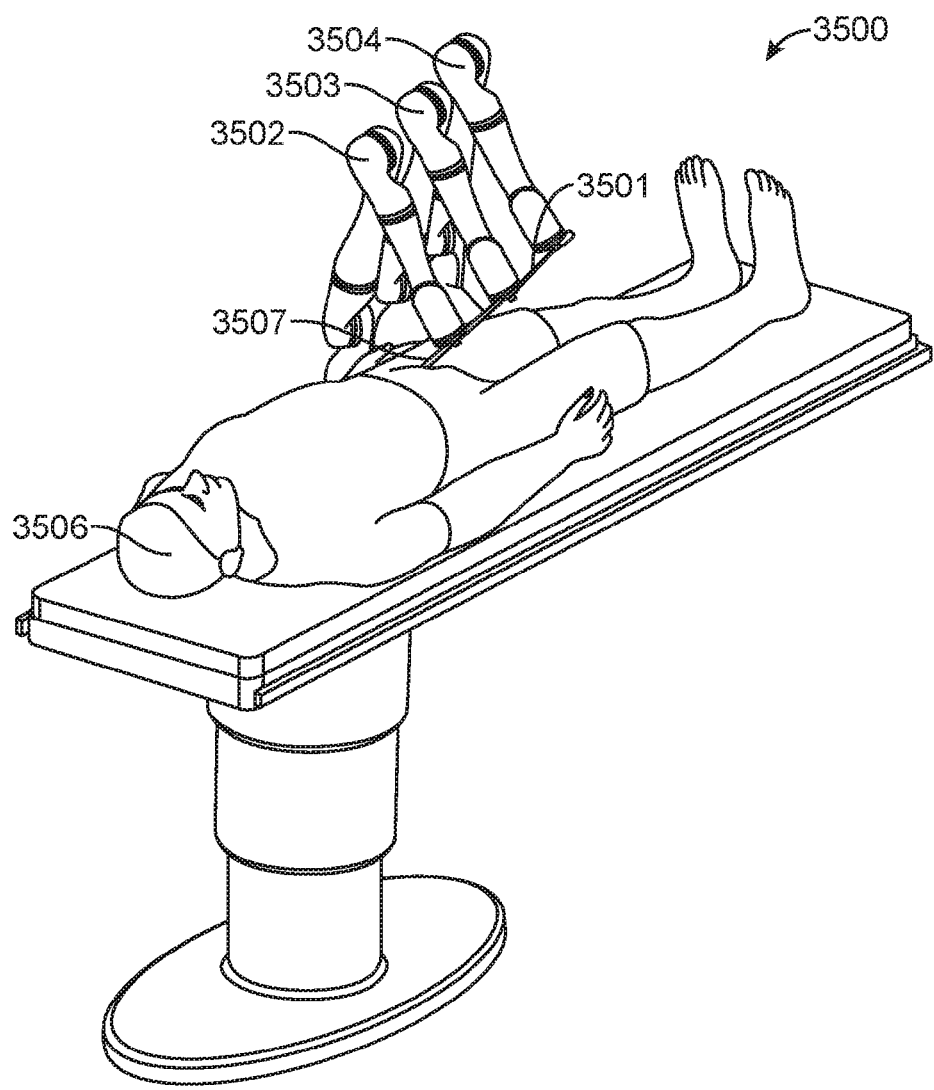
FIGS. 35A and 35B illustrate different views of a robotic catheter system, in accordance with an embodiment of the present invention.

FIG. 35A illustrates an isometric view of a robotic catheter system, in accordance with an embodiment of the present invention. As shown in FIG. 35A, the system 3500 delivers catheter device 3501 use of three mechanical arms (3502, 3503, and 3504) that are operatively coupled to the operating table 3505. Aligning the mechanical arms at angle relative to an insertion point 3507 in the femoral artery, the mechanical arms 3502, 3503, and 3504, the system 3500 may configure the catheter device 3501 into a virtual rail to access the femoral artery and the rest of the vascular system of the patient 3506. From within the femoral artery, the flexible catheter device may be articulated and "driven" throughout the rest of the patient's vascular system, such as up to the patient's heart.

Figure 35B:
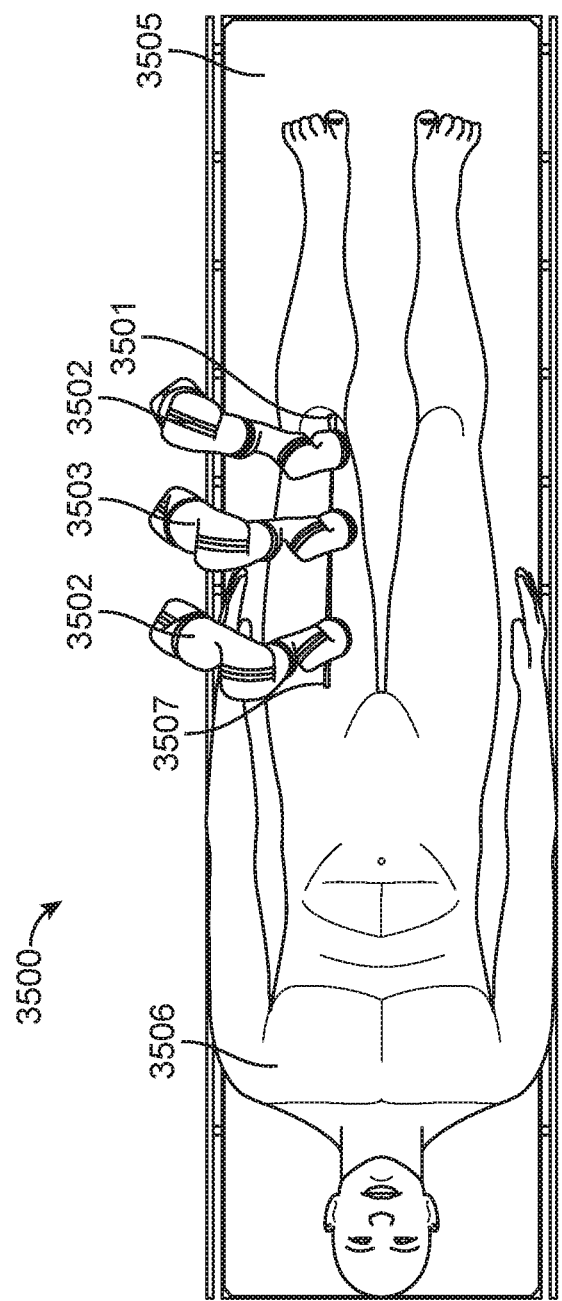

FIG. 35B illustrates a top view of robotic catheter system 3500, in accordance with an embodiment of the present invention. As shown in FIG. 35A, the mechanical arms 3502, 3503, and 3504 may be used to create a virtual rail for the catheter device 3501 above the left leg of the patient 3506. Hence, the flexibility of the mechanical arm system makes possible access to the insertion point 3507.

Figure 36:
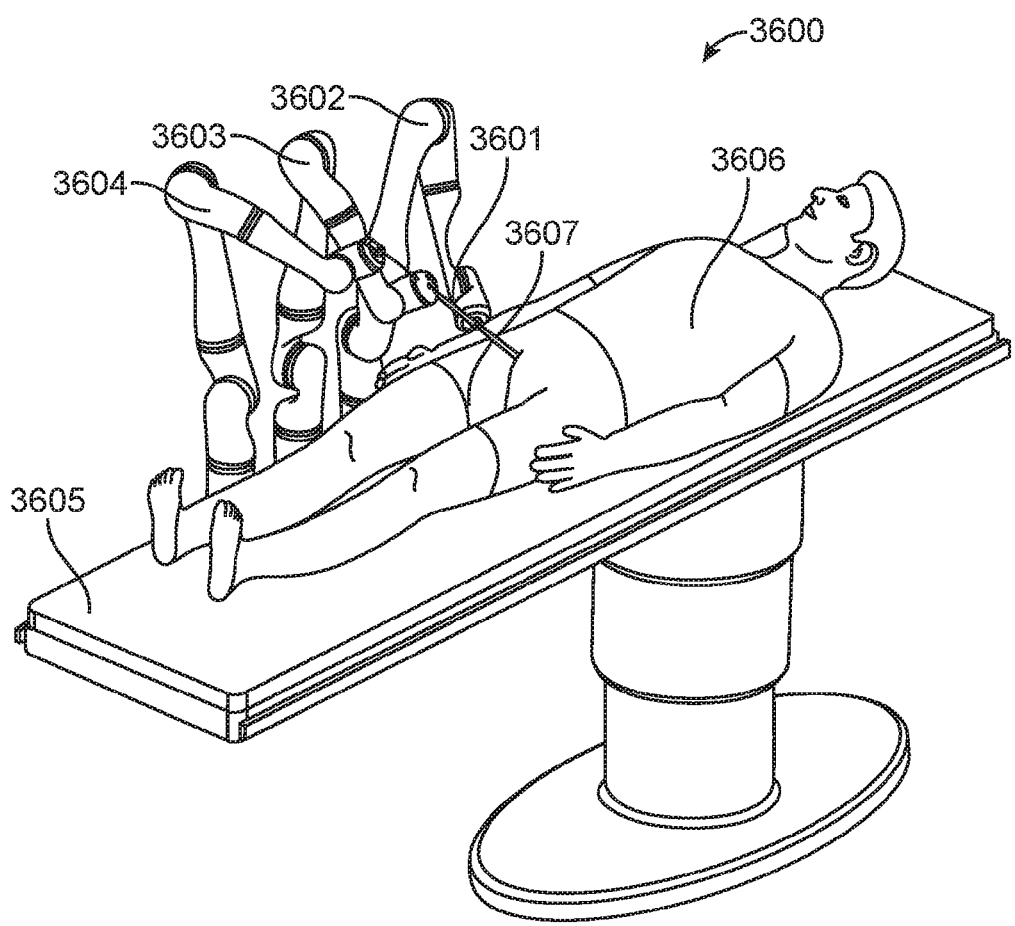
FIG. 36 illustrates an isometric view of a robotic catheter system where the angle of the virtual rail is greatly increased, in accordance with an embodiment of the present invention.

FIG. 36 illustrates an isometric view of a robotic catheter system where the angle of the virtual rail is greatly increased, in accordance with an embodiment of the present invention. Given its use of mechanical arms, the present invention allows for greater angles of insertion, depending on the application, procedure, and desires of the operator. As shown in FIG. 36, system 3600 may comprise three mechanical arms 3602, 3603, and 3604 operatively coupled to an operating bed 3605 with a patient 3606. The catheter 3601 may be aligned in a virtual rail within the patient's femoral artery within the patient's right leg 3607. In this arrangement, the angle between the device 3601 and the patient's leg 3607 may exceed forty-five degrees.

With the aid of the robotic control, the angle may also be changed intraoperatively, such that the insertion trajectory may differ from the start to the finish. Altering the insertion trajectory intraoperatively may allow for more flexible operating room arrangements. For example, it may be advantageous for a low initial insertion angle. However, as the procedure progresses it may be more convenient for the operator to increase the angle to provide additional clearance between the patient and the robotic system.

In addition to multiple rail configurations, the system's use of mechanical arms provides additional benefits. In current flexible catheter technologies, the flexible catheter often experiences resistance upon insertion of the catheter. This resistance, combined with the bendability of the catheter, results in the undesirable bending of the catheter exterior to the patient, i.e., "buckling" during insertion from "pushing" the catheter into the patient's body. This "buckling" phenomenon may be typically resolved by manually threading the catheter into the insertion point, resulting in additional labor for the operator. Moreover, the unsupported external portion of the catheter resulting from the "buckling" phenomenon is undesirable. The torque sensing algorithms and mechanisms may be used to identify instances of buckling in addition to external force inputs, as such force measurement may have a unique signature.

Figure 37A:
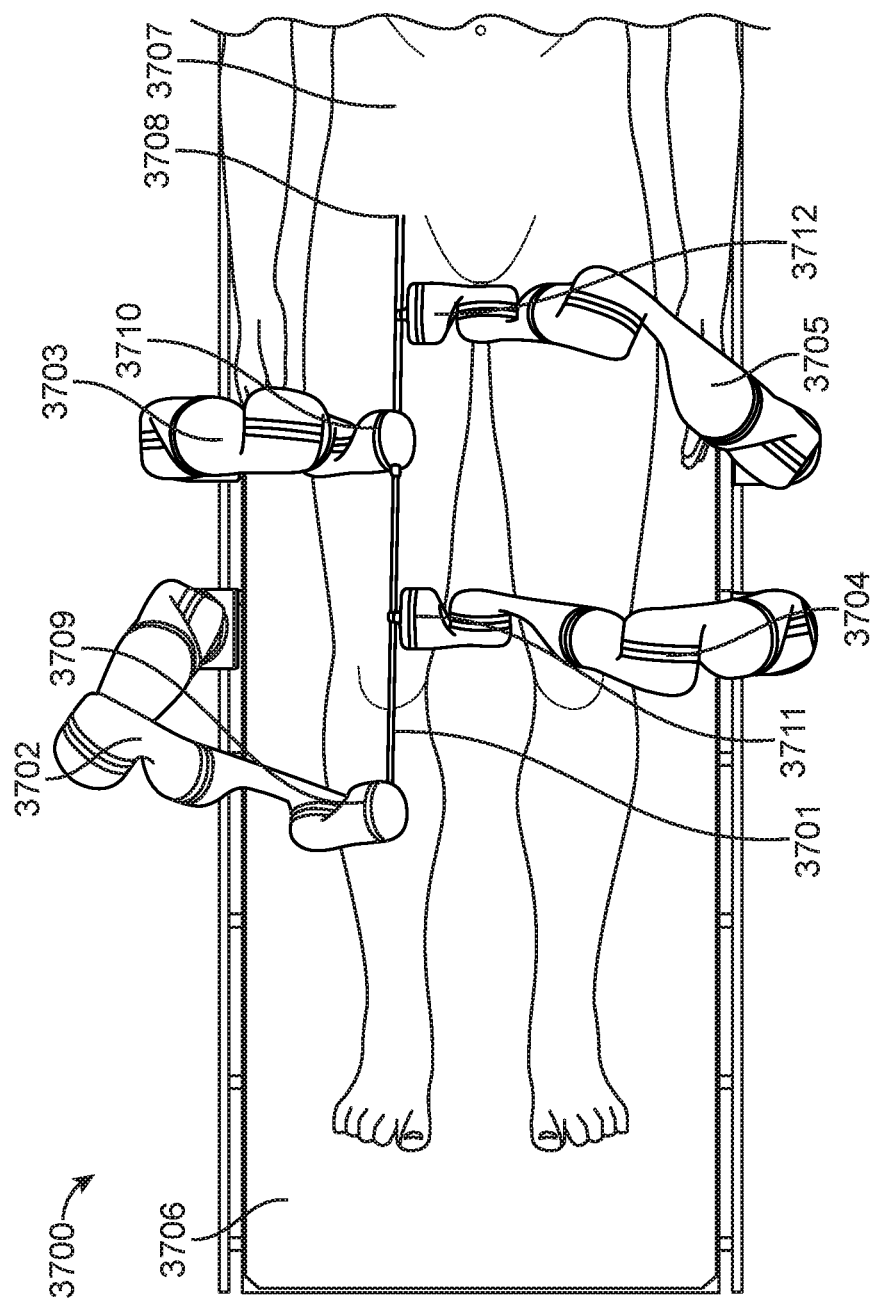

FIGS. 37A-37D illustrates a series of top views of a vascular procedure where the use of mechanical arms reduces catheter buckling and wasted length, in accordance with an embodiment of the present invention. In FIG. 37A, system 3700 incorporates the use of four mechanical arms 3702, 3703, 3704, and 3705 operatively coupled to an operating bed 3706 with a patient 3707. As shown in FIG. 37A, the arms may be used to align a catheter device 3701 into a virtual rail with an insertion point 3708 in the femoral artery in the right leg of the patient 3707.

The different arms in system 3700 serve different purposes for maneuvering the catheter 3701. Arms 3702 and 3703 may drive the catheter device 3701 through driving the tool bases 3709 and 3710 of catheter 3701. Tool bases 3709 and 3710 may be "driven" using any number of means, including direct drive methods discussed infra. Mechanisms at the flange points of arms 3704 and 3705 may be used to support catheter device 3701 to reduce buckling and reduce wasted length. The flange points 3711 and 3712 may support catheter 3707 through either passive or direct drive means. In passive support, the flange points 3711 and 3712 may use a simple loop, groove, redirect surface, or a passive rotary surface (i.e., wheels or rollers). In the embodiment shown in FIG. 37A, the flange points 3711 and 3712 provide passive "anti-buckling" support to catheter 3701. In passive support, arms 3704 and 3705 may move along the virtual to support the catheter device 3701 where it is mostly likely to bend. For example, in some embodiment, the arms 3704 and 3705 are configured to always maintain equal distances from the patient's body and the tool bases.

Figure 37B:
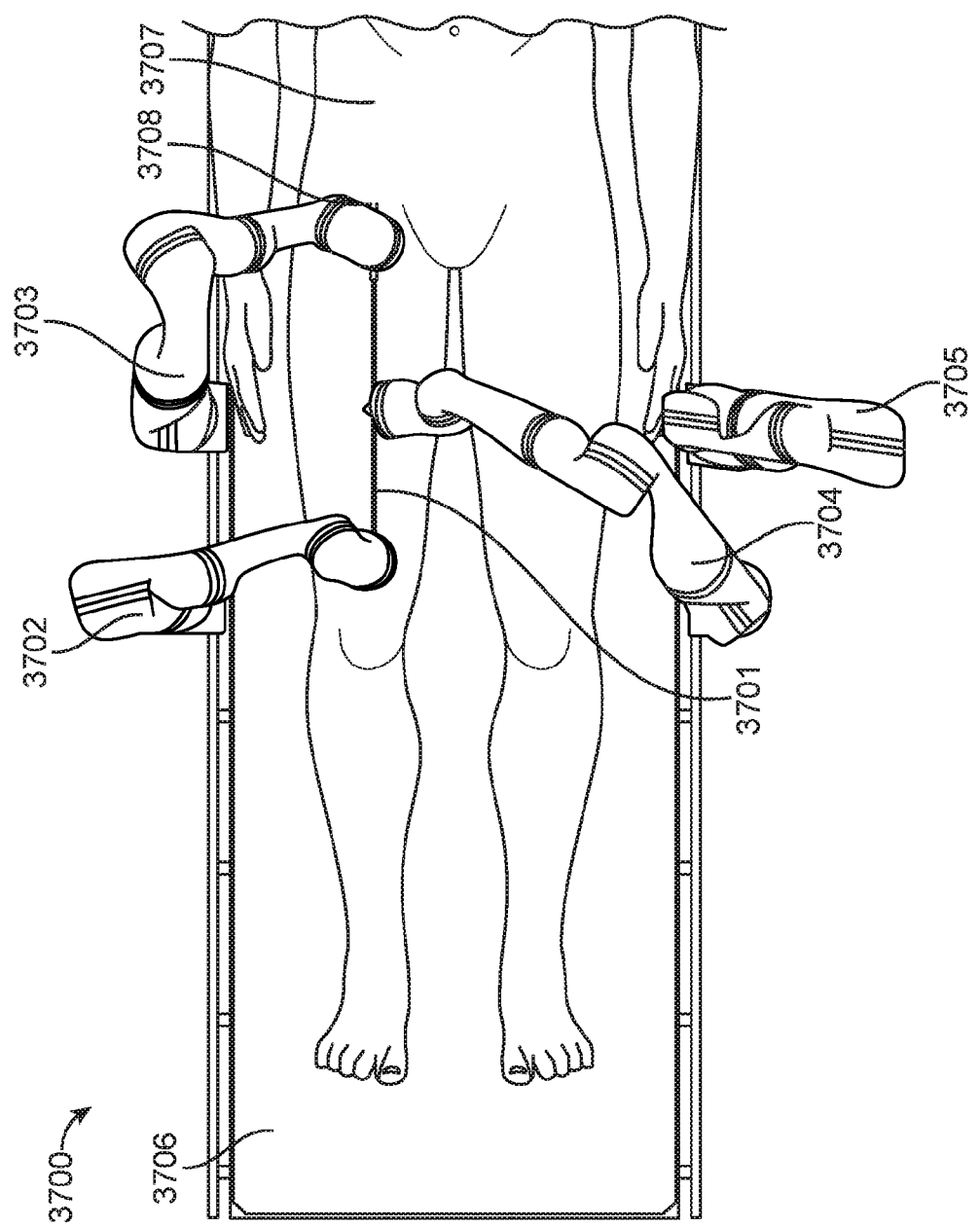

FIG. 37B illustrates a top view of the vascular procedure from FIG. 37A using system 3700, in accordance with an embodiment of the present invention. As shown in FIG. 37B, as the catheter 3701 is further inserted into the femoral artery of patient 3707, the support arm 3705 may be retracted to provide clearance for inserting the catheter 3701 into the patient. Thus, the arm 3705 may provide "anti-buckling" support when the catheter 3701 is first inserted, and may be removed when extension of the catheter 3701 is needed. This flexibility provides improved control over the catheter 3701 and reduces "wasted length" along the catheter 3701.

FIG. 37C illustrates a further top view of the vascular procedure from FIG. 37B using system 3700, in accordance with an embodiment of the present invention. As shown in FIG. 37C, as the catheter 3701 is again further inserted into the patient's femoral artery through insertion point 3708, support arm 3704 may also be retracted to provide clearance for inserting the catheter 3701 into the patient 3707. As with support arm 3705, the arm 3705 may provide "anti-buckling" support when needed, and may be retracted when further extending the catheter 3701.

In active support, the flange points on mechanical arms 3704 and 3705 may be a motorized or mechanized drive system, such as graspers or active rotary surfaces (i.e., wheels or rollers). In some embodiment, the flange points may remain stationary, as opposed to always adjusting in the case of passive support.

Figure 37D:
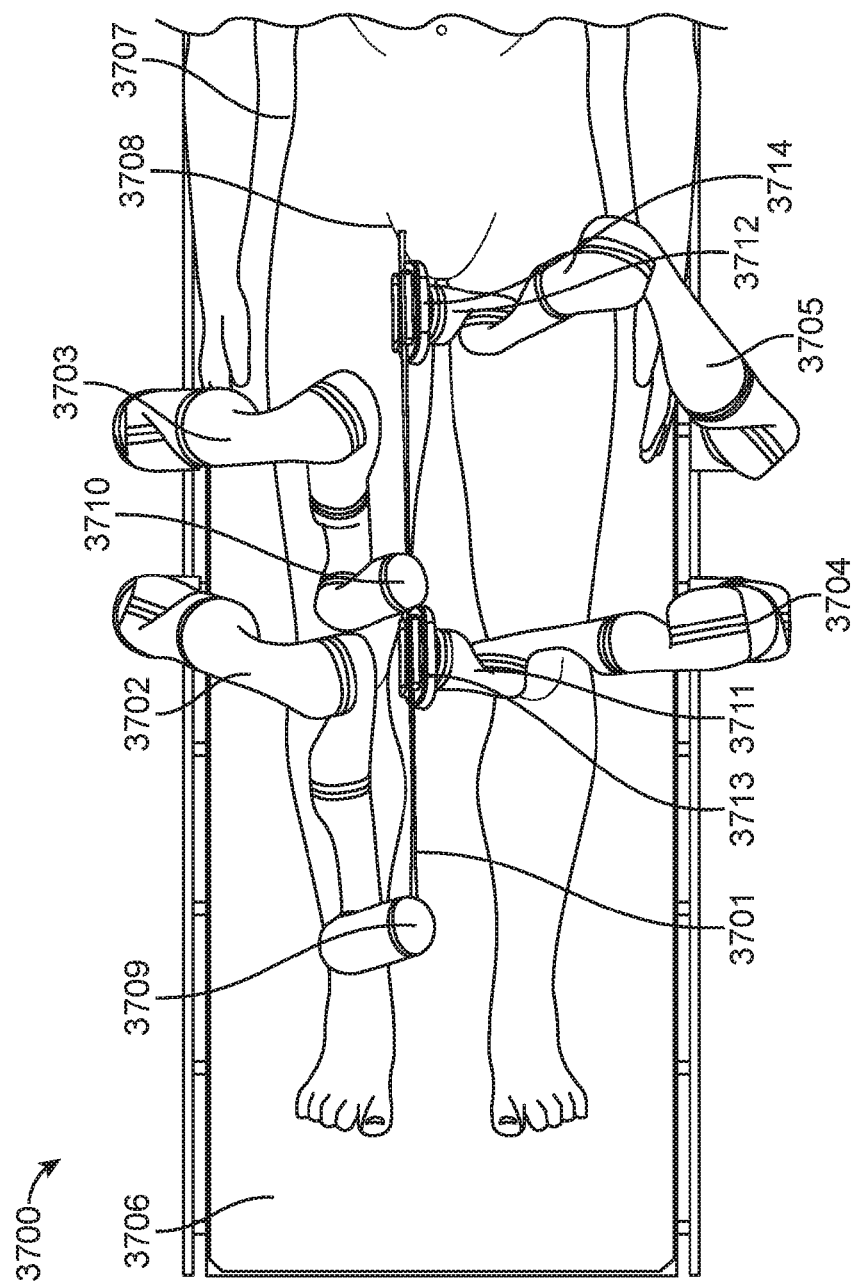

FIG. 37D illustrates a top view of a vascular procedure where mechanical arms provide active drive support through the use of motorized rollers at the flange points of the arms, in accordance with an embodiment of the present invention. Specifically, FIG. 37D illustrates the use of system 3700 from FIGS. 37A-37C where the passive support systems at flange points 3711 and 3712 are replaced by active drive mechanisms, such as rollers 3713 and 3714. In FIG. 37D, the active drive mechanisms 3713 and 3714 provide mechanized support to prevent anti-buckling. In some embodiments, the angular speed of the rollers may be synchronized with the drive controls over tool bases 3709 and 3710 to ensure proper insertion speed and control. Additionally, in order to replicate the pushing motion of a physician, active drive mechanisms 3713 and 3714 are located as close as possible to the insertion point. As the catheter 3701 is extended into the patient, the arms 3703 and 3704 may be retracted as necessary to get maximum extension length out of the catheter 3701.

While embodiments have been discussed with respect to access to the femoral artery, very similar arrangements of the mechanical arms may be configured in order to gain access to the femoral vein and saphenous vein.

Figure 38A:
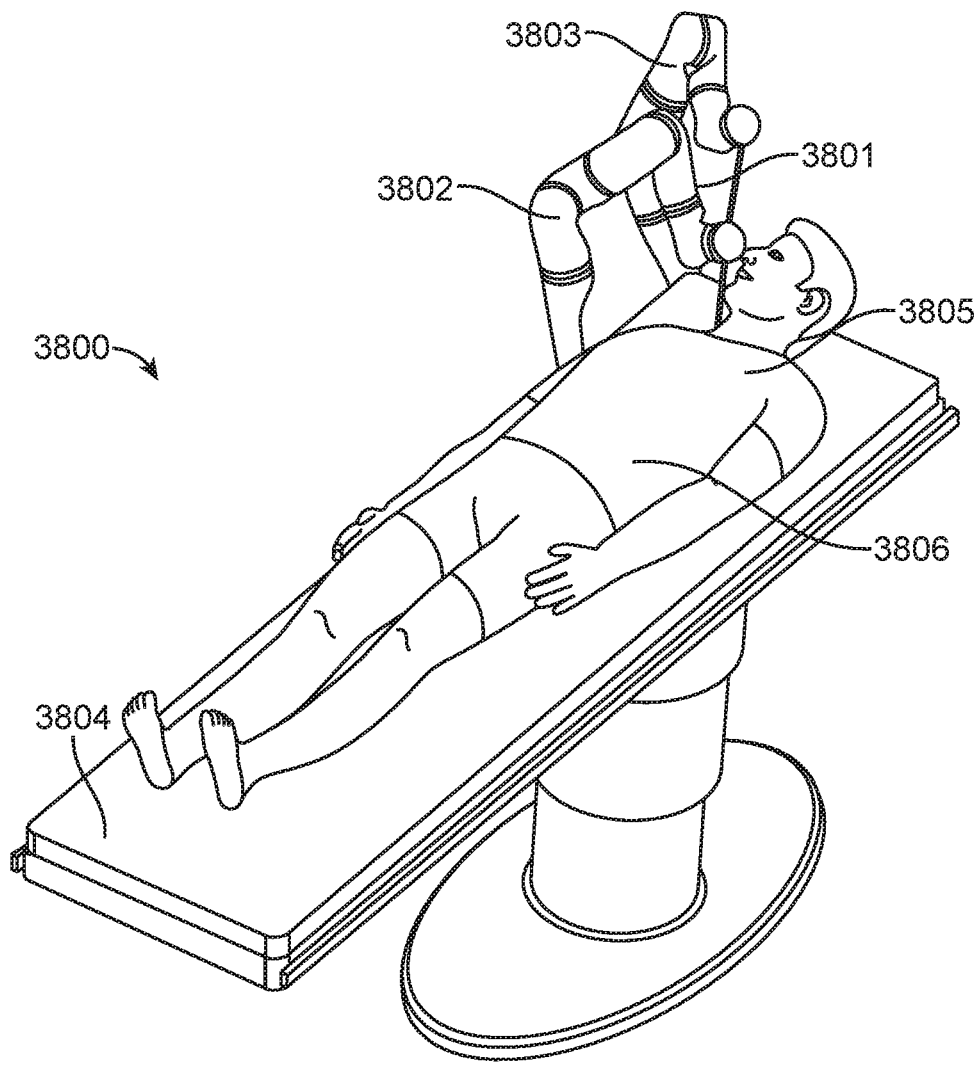
FIGS. 38A and 38B illustrate a vascular procedure where a robotic catheter may be inserted into the carotid artery, in accordance with an embodiment of the present invention.
Figure 38B:
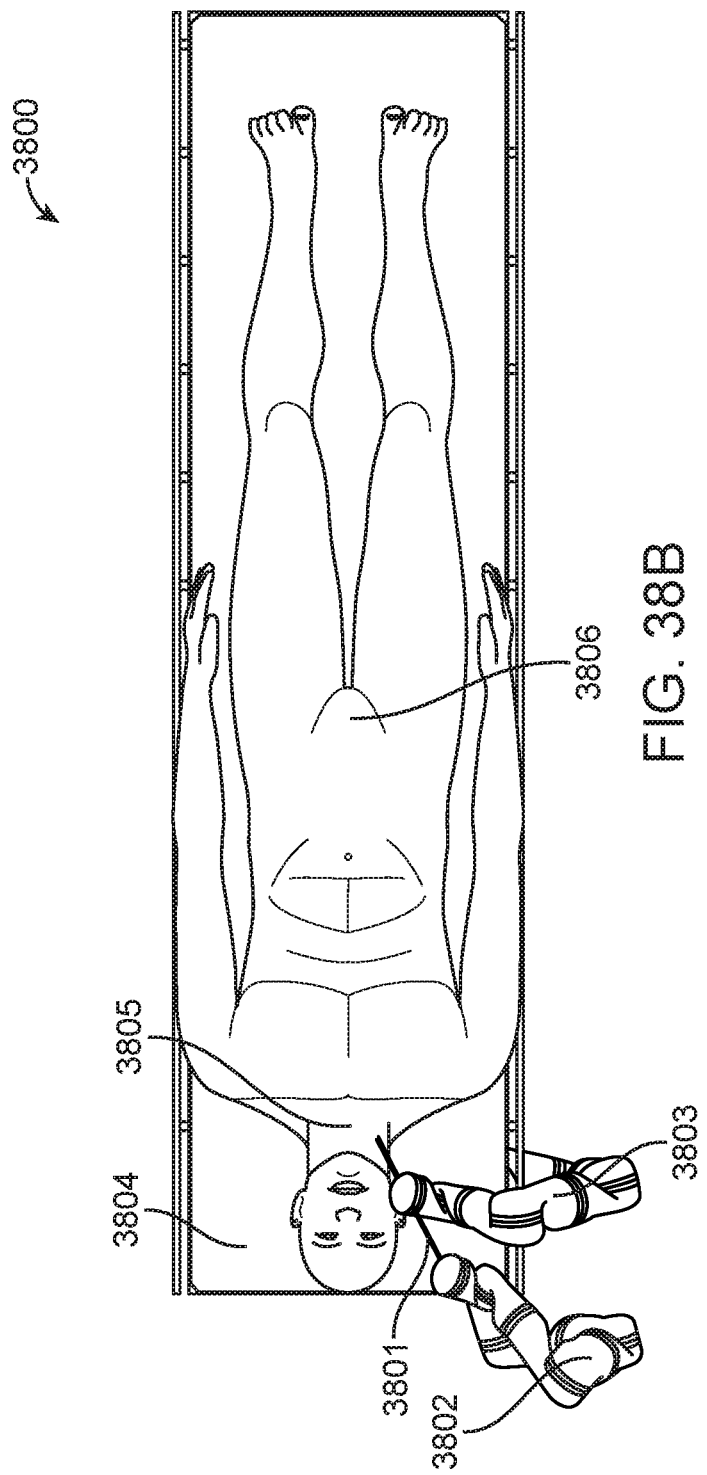

The flexibility of the present invention allows for a variety vascular procedures that require access to different points in the patient's vascular system. FIGS. 38A and 38B illustrate a vascular procedure where a robotic catheter may be inserted into the carotid artery, in accordance with an embodiment of the present invention. Specifically, FIG. 38A illustrates an isometric view of a vascular procedure where a catheter may be inserted into the carotid artery. As shown in FIG. 38A, the system 3800 delivers catheter 3801 using two mechanical arms (3802 and 3803) that are operatively coupled to the operating table 3804. The mechanical arms 3801 and 3802 may align the catheter 3801 into a virtual rail to access insertion point 3805 in the carotid artery and the rest of the vascular system of the patient 3806.

FIG. 38B illustrates a top view of vascular system 3800, in accordance with an embodiment of the present invention. As shown in FIG. 38B, the mechanical arms 3802 and 3803 may be used to create a virtual rail for the catheter 3801 above the shoulder of the patient 3806. Hence, the flexibility of mechanical arms 3802 and 3803 makes possible access to insertion point 3805 at the carotid artery.

Figure 39:
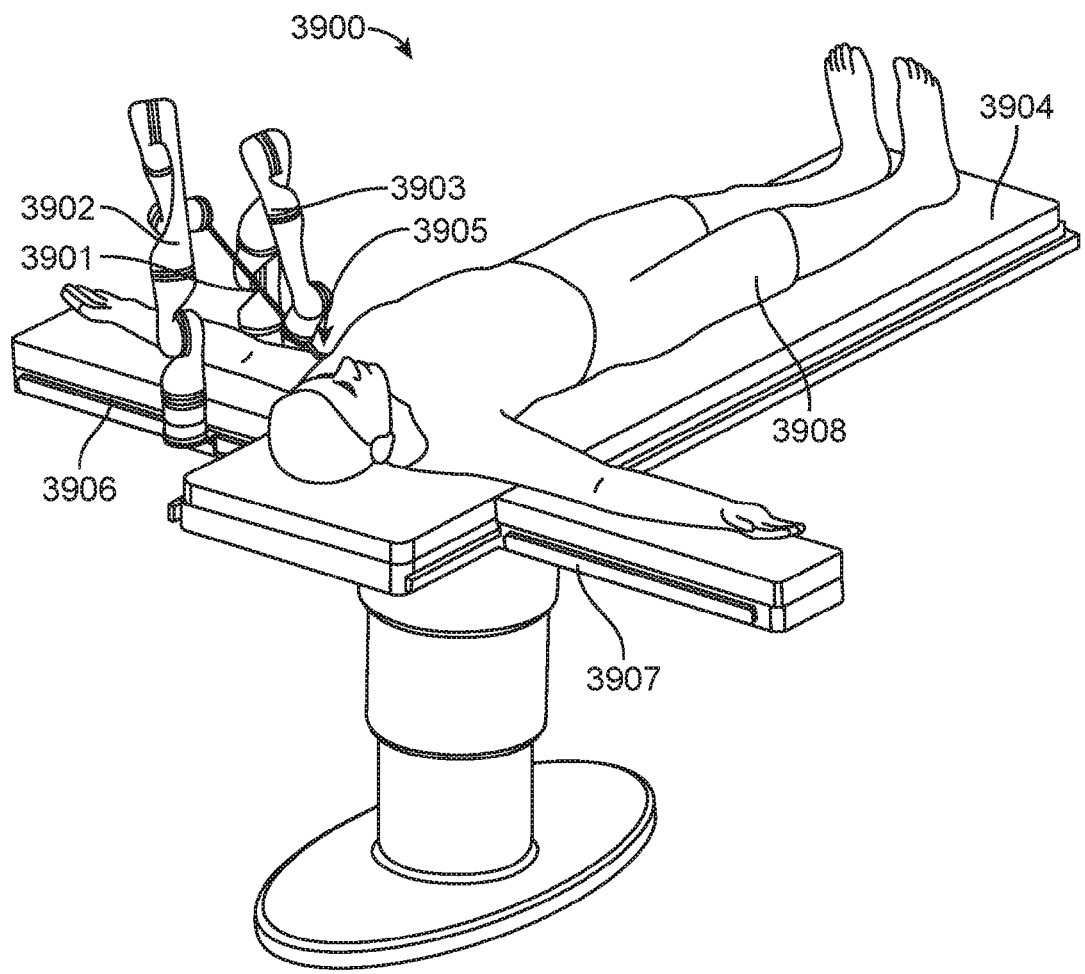
FIG. 39 illustrates a vascular procedure where a robotic catheter may be inserted into the brachial artery, in accordance with an embodiment of the present invention.

FIG. 39 illustrates a vascular procedure where a robotic catheter may be inserted into the brachial artery, in accordance with an embodiment of the present invention. In FIG. 39, the system 3900 delivers catheter 3901 using two mechanical arms (3902 and 3903) that are operatively coupled to the operating table 3904. In order to accommodate access to the insertion point 3905, operating table 3904 may be outfitted with a left extension 3906 and a right extension 3907, both of which include rails to allow arms 3902 and 3903 to slidingly access the extensions. Mechanical arms 3902 and 3903 may then align the catheter 3901 into a virtual rail to access the insertion point 3905 in the brachial artery and the rest of the vascular system of the patient 3908.

Figure 40A:
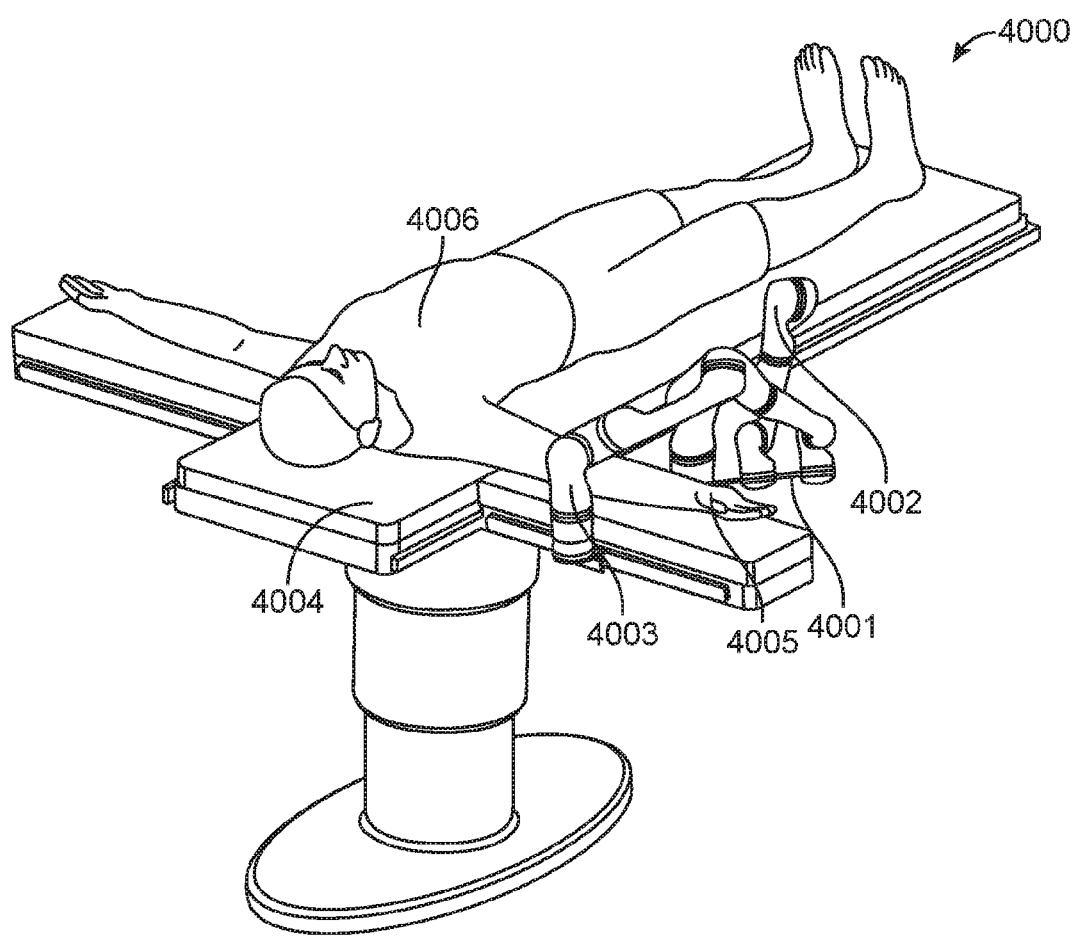
FIGS. 40A and 40B illustrate a vascular procedure where a robotic catheter may be inserted into the radial artery, in accordance with an embodiment of the present invention.
Figure 40B:
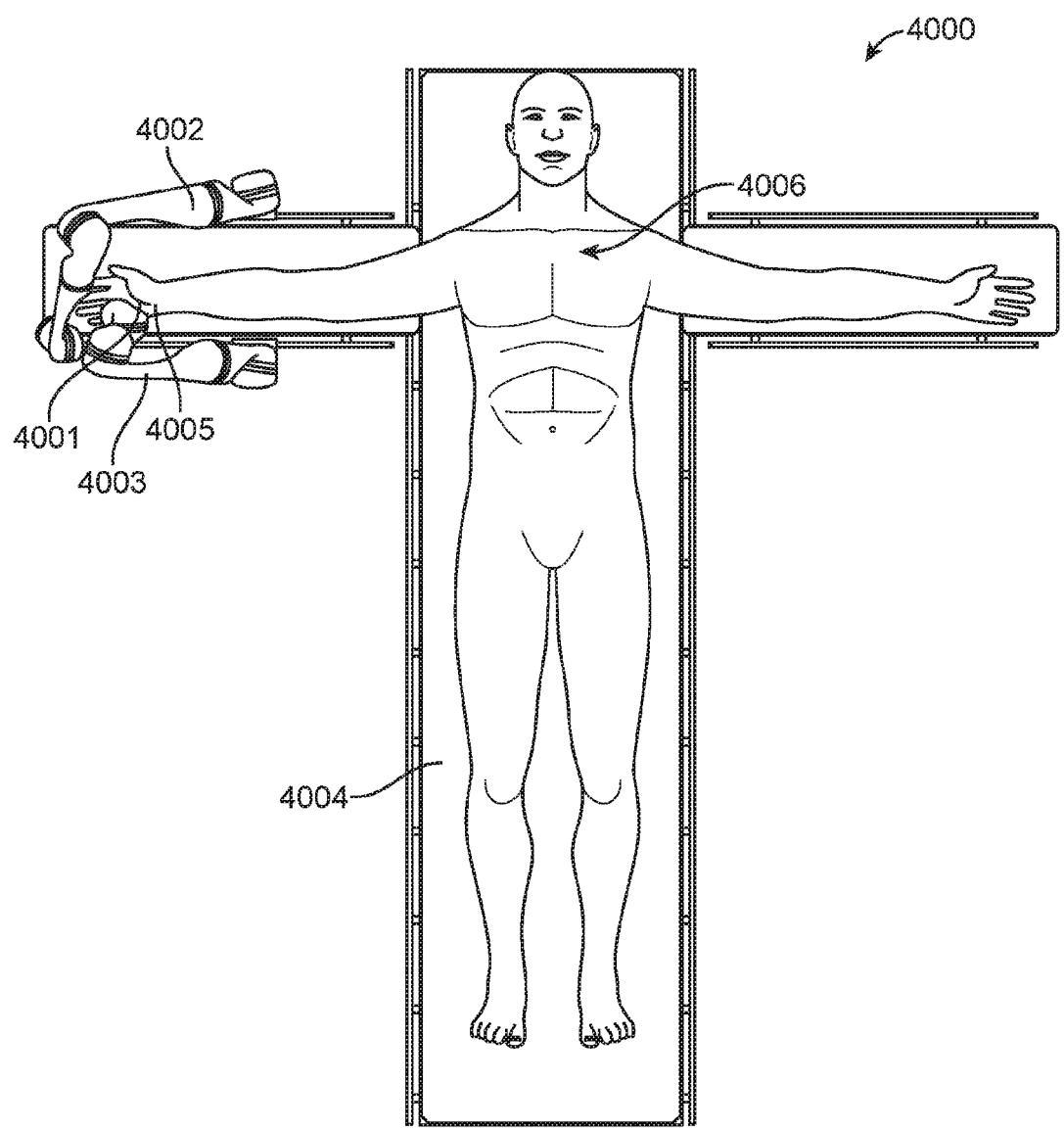

FIGS. 40A and 40B illustrate a vascular procedure where a robotic catheter may be inserted into the radial artery, in accordance with an embodiment of the present invention. Specifically, FIG. 40A illustrates an isometric view of a vascular procedure where a catheter may be inserted into the radial artery. As shown in FIG. 40A, the system 4000 delivers catheter 4001 using two mechanical arms (4002 and 4003) that are operatively coupled to the operating table 4004. The mechanical arms 4002 and 4003 may align the catheter 4001 into a virtual rail to access insertion point 4005 in the radial artery and the rest of the vascular system of the patient 4006.

FIG. 40B illustrates a top view of vascular system 4000, in accordance with an embodiment of the present invention. As shown in FIG. 40B, the mechanical arms 4002 and 4003 may be used to create a virtual rail for the catheter 4001 above the wrist of the patient 4006. Hence, the flexibility of mechanical arms 4002 and 4003 makes possible access to insertion point 4005 at the radial artery.

Thus, a plurality of arms and/or platforms may be utilized to form a "virtual rail" to enable a variety of procedures that require a variety of patient access points. In operation, each platform/arm must be registered to the others, which can be achieved by a plurality of modalities including, vision, laser, mechanical, magnetic, or rigid attachment. In one embodiment, registration may be achieved by a multi-armed device with a single base using mechanical registration. In mechanical registration, an embodiment may register arm/platform placement, position, and orientation based on their position, orientation and placement relative to the single base. In another embodiment, registration may be achieved by a cart-based system with multiple base using individual base registration and "hand-shaking" between multiple robot arms. In cart-based embodiments with multiple bases, registration may be achieved by touching together arms from different bases, and calculating locations, orientation and placement based on (i) the physical contact and (ii) the relative locations of those bases. Registration techniques in bed- or table-based systems may be different. In some embodiments, registration targets may be used to match the position and orientations of the arms relative to each other. Through such registration, the arms and instrument driving mechanisms may be calculated in space relative to each other.

Methods for Virtual Rail Alignment.

Figure 41:
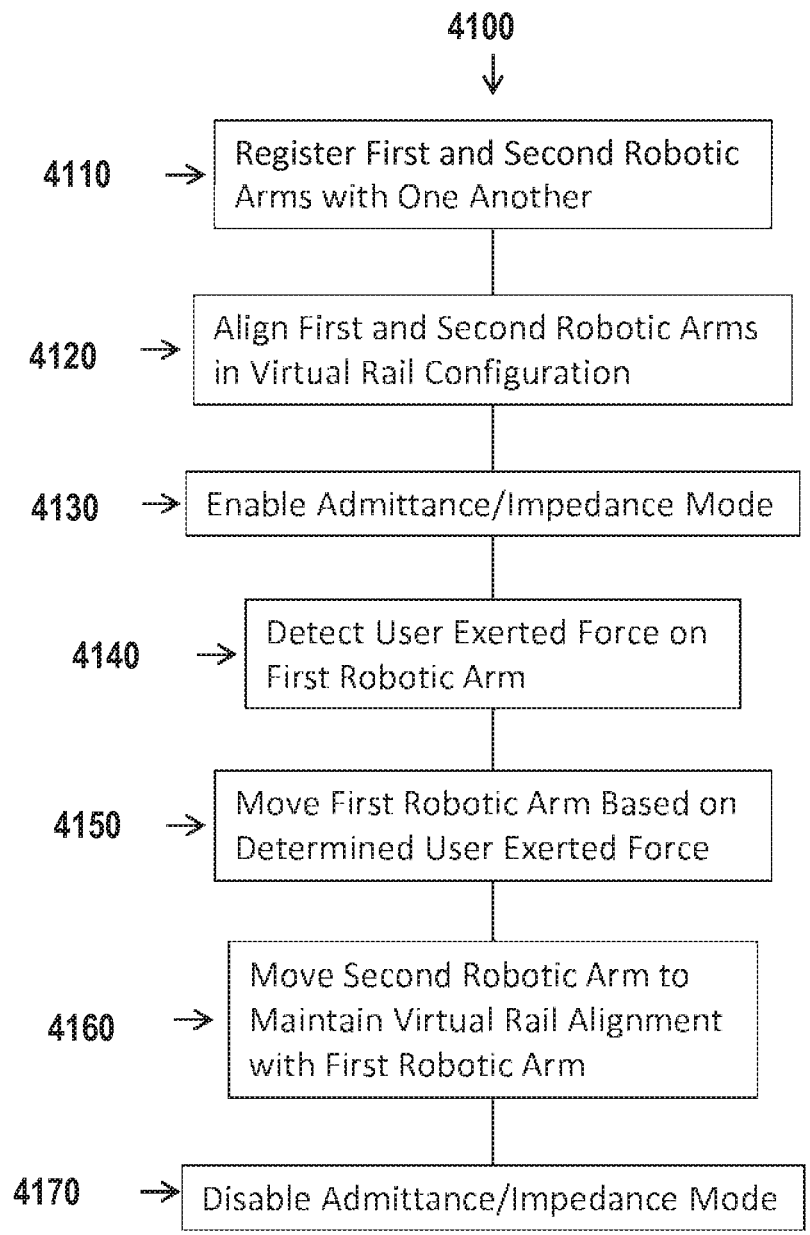
FIG. 41 shows a flow chart illustrating a method for aligning the arms of a robotic surgery system, in accordance with many embodiments.

FIG. 41 shows a flow chart illustrating a method 4100 for aligning the arms of a robotic surgery system. The arms of the robotic surgery system may be aligned according to the method 4100 before, during, or after an operation on a patient. In some embodiments, arm alignment methods may incorporate the use of an offset for accommodating configurations that are involve curved paths or jointed paths (such as Y-shapes).

In a step 4110, the first and second robotic arms of the system may be registered with one another. In some embodiments, the system may comprise a third robotic arm or further robotic arm(s) which may be registered with one another.

In a step 4120, the first and second robotic arms, typically their tool bases, may be aligned to be in a virtual rail configuration. Typically, the end effectors, interface ends, device manipulators, or tool bases of the robotic arms may be robotically aligned in the virtual rail. In some embodiments, a third robotic arm or further robotic arm(s) may be aligned to be in the virtual rail configuration as well. In some embodiments, a third robotic arm may be used to position a patient interface device at the patient access point. In some embodiments, a third robotic arm may be used to position a guidewire or tool manipulator for use in the working channel of an endoscopic device.

In a step 4130, an admittance/impedance mode of the robotic surgery system may be enabled. The admittance/impedance mode may be enabled in any number of ways such as with voice control, joystick control, pedal control, computer device control, etc. Admittance mode for a robotic component is generally a control algorithm in which the robot translates a sensed force to a velocity or acceleration command. Torque sensors or tactile sensors on the robot arm sense an external force, such as a person pushing on the end of the arm, and use the force vector as a command to the robot to move. However, unintended external forces, such as an accidental bump, may cause the robot to move if admittance mode is enabled. The use of buttons or toggle switches can enable/disable admittance mode, but can become difficult for a person to interact with multiple arms.

In some embodiments, the use of direct physical input to the arms, such as a "tap" or "push on the arms can also be used to enable admittance mode. This may simplify human-to-robot interaction and make it more instinctive. For example, in an embodiment, when admittance mode is disabled the robot holds position while the torque sensors continuously read—and wait for—inputs. When a double tap is performed on the arm, the tap signature is identified by an algorithm and switches the robot to admittance mode.

Put differently, admittance control is an approach to the control of dynamic interaction from a robot to its environment. In admittance control, the robot takes force as an input and calculates a resulting velocity or acceleration as its output. If a robot in admittance mode is given an external force, such as a push, the controller will drive the robot to move in the opposite direction until the force is minimized. Virtual parameters such as mass, spring, and damping can be tuned in admittance control to change the relationship between force and position.

In contrast, impedance mode is the inverse of admittance mode. In impedance mode, the robotic component has a position input which results in a force output. The control loop uses a position measurement to determine whether to output an external force. For example, a robot in impedance mode may be directed to move forward (input) until it touches a wall and to touch the wall at a constant force of 5 Newtons (force). When a robot in impedance mode is given a force profile to follow, the robot will move to maintain that force profile. In layman's terms, the robotic component moves away to avoid an applied external force in admittance mode, while the robotic component moves to maintain an applied external force in impedance mode.

In a step 4140, the first robotic arm may detect a user exerted force on the first robotic arm. The first robotic arm may comprise one or more links and joints; and, the first robotic arm may comprise a torque sensor coupled to the joint or a tactile and/or force sensor coupled to the link, such as by being placed over the outer surface of the link. For example, the robotic arm may comprise a series of actuators held by links in-between and may comprise a 7 actuator, serial chain arm; and, the robotic arm may sense torque at each joint and/or have tactile sensing along the robotic arm. Alternatively or in combination, a force sensor may also be coupled to the tool base, device manipulator, or interface end of the first robotic arm. The second or further robotic arm (s) may be similar to the first robotic arm.

The robotic arm may be coupled to a controller implementing an algorithm to calculate where an external force occurs. When using tactile sensors, sensors which are activated may directly show the location of the external force. For torque sensing at the joint, the algorithm may do an estimate to calculate where the input force may occur on the arm. The algorithm may read the type of input given, such as whether an input is a slow push, quick tap, a shake, or a pull.

In a step 4150, the first robotic arm may move, typically automatically, based on the determined user exerted force vector.

In a step 4160, the second robotic arm may move, typically automatically and concurrently, to maintain the virtual rail alignment with the first robotic arm. In some embodiments, a third robotic arm or further robotic arm(s) may move, typically automatically and concurrently, to maintain the virtual rail alignment with the first and second robotic arms.

The first, second, and optionally further robotic arms may move in the many ways described below and herein, such as along one or more of an X-axis, a Y-axis, or a Z-axis (in which case the robotic arms may have the same movement vectors) or to pivot or rotate about a point on the virtual rail line (in which case the robotic arms may have different movement vectors and magnitudes). For example, a user such a physician may grab and move one of the end effectors and move the entire set of end effectors which remain in the virtual rail alignment. In other examples, the robotic arms may be pivoted about a point where the site where the endoscopic device or tool is introduced to the patient being operated on.

In some embodiments, the system may comprise a third or further robotic arm and the force exerted on a subset of the robotic arms (e.g., two of the robotic arms) may be detected so that entire set of the robotic arms are moved in a manner that maintains the virtual rail alignment. For example, a user such a physician may grab two of the end effectors and translate them with a substantially similar movement vector to each in one or more of the X-axis, Y-axis, or Z-axis and the remaining end effectors may be automatically moved in a manner that maintains the virtual rail alignment. In other examples, a user such as a physician may grab two of the end effectors and translate them with different movement vectors to each and the remaining end effectors may be automatically moved in a manner that maintains the virtual rail alignment and that rotates the end effectors about a point on the virtual rail line. In still other examples, an end effector may be grabbed and rotated to rotate the virtual rail of end effectors about the grabbed and rotated end effector. The movement of the robotic arms and the end effectors may be that of translation when the system detects that one of the end effectors is grabbed, for example, and the movement of the robotic arms and the end effectors may be that of rotation when the system detects that two or more of the end effectors are grabbed and translated, for example, or when a single end effector is rotated, as another example.

In a step 4170, the admittance/impedance mode of the robotic surgery system may be disabled. The admittance/impedance mode may be disabled in any number of ways such as with voice control, joystick control, pedal control, computer device control, sensor reading, time out, etc. In other embodiments, the admittance/impedance mode may be disabled upon detecting the absence of external applied force. In some embodiments, either mode may be effectively disabled by a significant increase in force threshold.

Although the above steps show the method 4100 of aligning the arms of a robotic surgery system in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as desired or beneficial.

One or more of the steps of the method 4100 may be performed with circuitry as described herein, for example, with one or more of a processor or logic circuitry such as a programmable array logic or field programmable gate array. The circuitry may be a component of the control console or control computing unit described herein. The circuitry may be programmed to provide one or more of the steps of the method 4100, and the program may comprise program instructions stored on a computer readable memory or programmed steps of the logic circuitry such as the programmable array logic or field programmable gate array, for example.

Figure 42A:
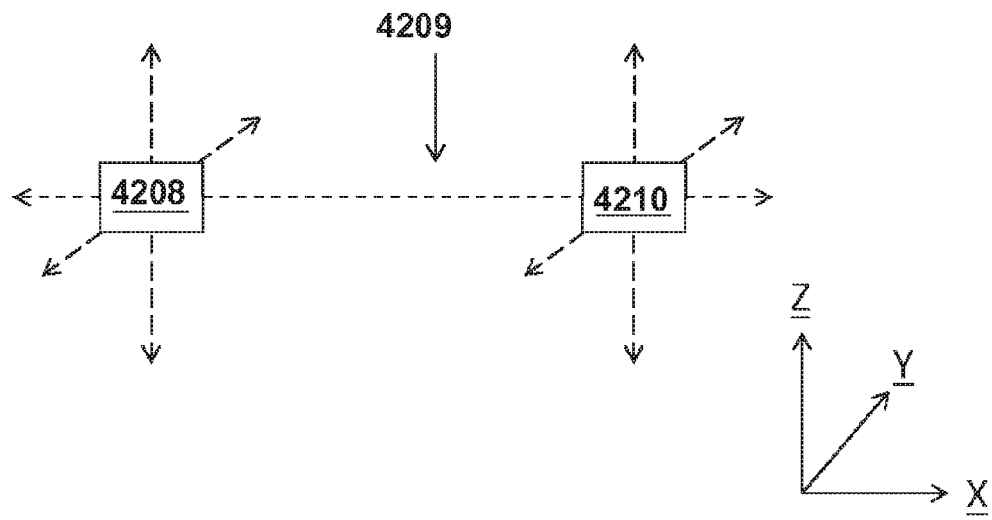
FIG. 42A shows a schematic of the aligned arms of a robotic surgery system translating in up to three dimensions, in accordance with many embodiments.

Referring to FIG. 42A, a first robotic arm tool base 4208 and a second robotic arm tool base 4210 may be aligned to form a virtual rail 4209. As shown in FIG. 42A, the first and second robotic arm tool bases 4208, 4210 may be translated concurrently in one or more of the X-axis X, Y-axis Y, or Z-axis Z while maintaining the virtual rail 4209. Typically, the axial distance between the first and second robotic arm tool bases 4208, 4210 may remain constant through any movement. In such movements, the movement vector of the first and second robotic arms are the same. In some cases, the axial distance may increase or decrease during the movement.

Figure 42B:
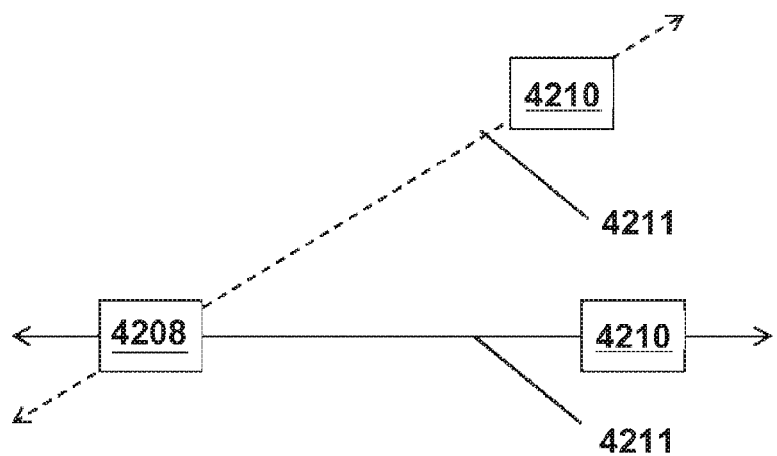
FIG. 42B shows a schematic of the aligned arms of a robotic surgery system pivoting about one of the device manipulators of robotic arms, in accordance with many embodiments.

The first and second robotic arm tool bases 4208, 4210 may also be moved with different movement vector to simulate the pivoting of the virtual rail 4209. As shown in FIG. 42B, the virtual rail 4209 may pivot about one of the tool bases such as the first robotic arm tool base 4208. In such cases, the movement vector of the second robotic arm tool base 4210 may be substantially greater than the movement vector of the first robotic arm tool base 4210, which may be minimal. The first robotic arm tool base 4208 may alternatively pivot about the second robotic arm tool base 4210 as well.

Figure 42C:
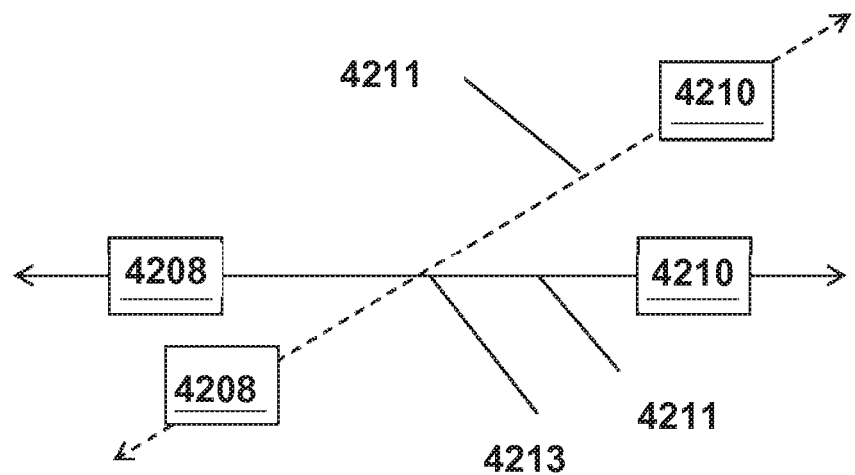
FIG. 42C shows a schematic of the aligned arms of a robotic surgery system pivoting about a point between two of the device manipulators of robotic arms, in accordance with many embodiments.

As shown in FIG. 42C, the virtual rail 4209 may pivot about a pivot point 4213 on the virtual rail line between the first and second robotic arm tool bases 4208, 4210. In such cases, the movement vectors of the two robotic arm tool bases 4208, 4210 may be similar in magnitude but may be opposite in direction.

Figure 42D:
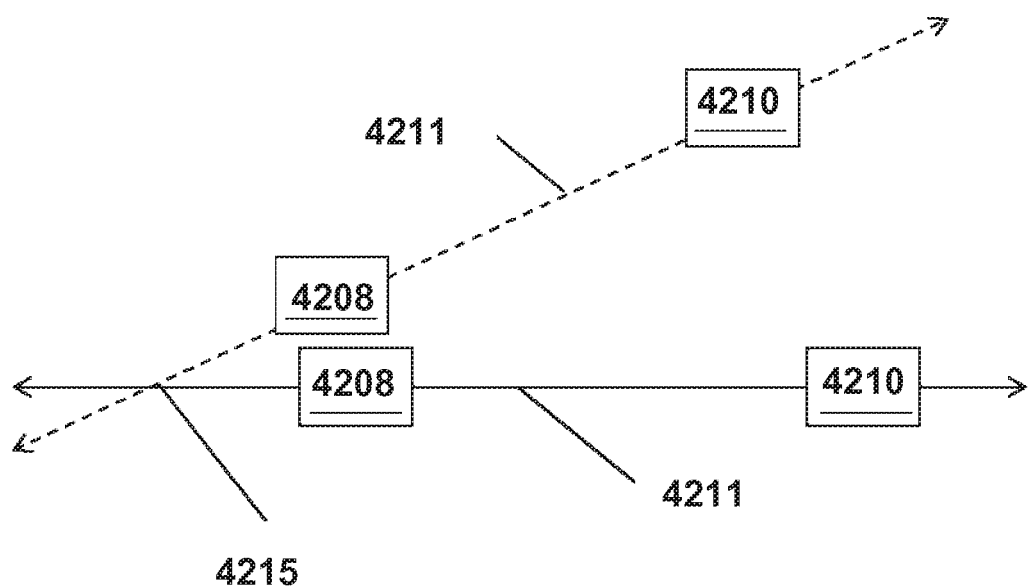
FIG. 42D shows a schematic of the aligned arms of a robotic surgery system pivoting about a point beyond two of the device manipulators of robotic arms, in accordance with many embodiments.

As shown in FIG. 42D, the virtual rail 4209 may pivot about a pivot point 4215 on the virtual rail line beyond the first and second robotic arm tool bases 4208, 4210. In such cases, the movement vector of the second robotic tool base 4210 may be substantially greater than the movement vector of the first robotic arm tool base 4208. As shown in FIG. 42D, the pivot point 4215 lies on the virtual rail line to the "left" of the first robotic arm tool base 4208. Alternatively, the pivot point 4215 may lie on the virtual rail to the "right" of the second robotic arm tool base 4208.

While FIGS. 42B-42D show a pivoting of the virtual rail in the counter-clockwise direction and with an angle of about 30 degrees, such direction and angle of pivoting is shown for example only. The virtual rail may be pivoted clockwise and with any angle between 0 and 360 degrees as well.

Admittance/Impedance Mode.

In an operating room, where a doctor and an assistant are performing a surgical task, the assistant is typically holding an instrument for the doctor. This instrument (such as a camera or retractor) often needs to be periodically repositioned and thus cannot be held by a rigid fixture. The use of a robot could reduce the need for a human assistant, but the control of many robots with a joystick or toggle buttons is not instinctive. Likewise, setup of a robotic system for each new patient is slow, partially due to the inconvenience of the control interface to the robot. The present disclosure provides systems, devices, and methods in which sensors, gesture recognition, and admittance/impedance control are used to create a human-robot interaction mode which is instinctive and easy.

The present disclosure provides for the sensing and control of the robot to take natural human inputs, such as a tap, push, or pull, on the arm to command an expected motion. For example, a double tap on the "elbow" of the arm (e.g., a joint of the robotic arm) can mean the human wants the "wrist" to maintain position and to only move its elbow. In another example, if the "forearm" (e.g., a link of the robotic arm) is held firmly and the "wrist" (e.g., the tool base, interface end, or device manipulator of the robotic arm) is pulled, it can mean the human wants to arm to maintain position only rotate the "wrist." In third example, if the "wrist" is pushed by itself, then it can mean the human wants to whole arm to follow the new position of the "wrist." The robot does this by sensing where and how the human is giving touch inputs to the arm, and uses that input (tap, double tap, tug, vibration, etc.) to enable admittance mode, a control scheme in which the robot takes force input as a motion command. The behavior of the admittance mode, such as which joints can be enabled or virtual limits on motion, is defined by the type of human input given.

The use of natural human inputs may extend to instances outside of manipulating a virtual rail. In one embodiment, if an arm is in a pivot mode, a strong pull in an approximate direction may toggle admittance mode and retract the rail along a straight line through the pivot point. In another embodiment, if no tool is present on the end effector, a large downward force applied by the physician may set the robot to a stowage sequence to store the arms. In other embodiments, the system may request confirmation prior to stowing the arms.

In some embodiments, admittance mode may be normally disabled. The present disclosure provides precise control of the robot arm and can compensates for external disturbances which may be unintended. When a touch gesture or input is given, the algorithm understands the user's intent and enables an admittance mode to match that intended motion. This may replace other modes for toggling admittance mode. When the external force is removed, the algorithm senses no input and disables admittance mode, either instantaneously, after a given wait time, or gradually (by increasing virtual damping and stiffness).

Figure 43:
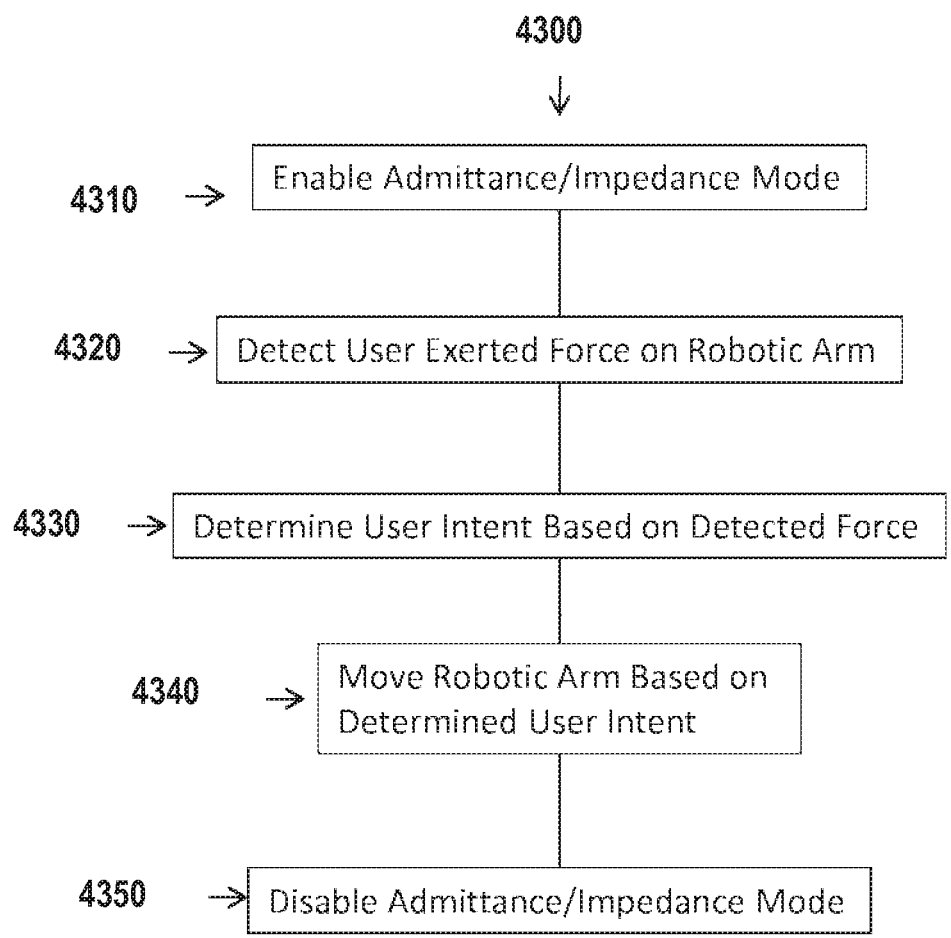
FIG. 43 shows a flow chart illustrating a method for manipulating the robotic arm(s) of a robotic surgery system, in accordance with many embodiments.

FIG. 43 shows a flow chart illustrating a method 4300 for manipulating the robotic arm(s) of a robotic surgery system. The arms of the robotic surgery system may be manipulated according to the method 4300 before, during, or after an operation on a patient.

In a step 4310, an admittance/impedance mode of the robotic surgery system may be enabled. The admittance/impedance mode may be enabled by the user exerting a force (i.e., touching and contacting) the robotic arm as described above and herein. Alternatively or in combination, the admittance/impedance mode may be enabled by user instruction received from a foot pedal in communication with the robotic arm, a joystick in communication with the robotic arm, a voice command, a detected light, or a computing device in communication with the robotic arm, to name a few examples. In some embodiments, the initial position of the robotic arm may be memorized. In some embodiments, the robotic arm may be configured to be able to memorize a number of positions determined by the user.

In a step 4320, the robotic arm may detect the force the user exerts on the robotic arm, such as a touch, grab, a tap, a push, a pull, etc. The robotic arm may comprise one or more links and joints; and, the robotic arm may comprise a torque sensor coupled to the joint or a tactile sensor coupled to the link, such as by being placed over the outer surface of the link. For example, the robotic arm may comprise a series of actuators held by links in-between and may comprise a 7 actuator, serial chain arm; and, the robotic arm may sense torque at each joint and/or have tactile sensing along the robotic arm. Alternatively or in combination, a force sensor may also be coupled to the tool base, device manipulator, or interface end of the robotic arm.

In some embodiments, tactile sensor and/or torque sensors may also record the robot's physical interactions with the environment. For example, the sensors may capture inadvertent force from the physician (e.g., bumping) that may be analyzed to better determine and define the clinical and robotic workspace.

In a step 4330, the user intent may be determined based on the detected force. For example, the robotic surgery system may determine whether the exerted force is one or more of a hold, a push, a pull, a tap, a plurality of taps, a rotation, or a shake of at least a portion of the robotic arm. In some embodiments, the detected force may indicate toggling admittance mode on or off.

The robotic arm may be coupled to a controller implementing an algorithm which can calculate where an external force occurs. When using tactile sensors, sensors which are activated may directly show the location of the external force. For torque sensing at the joint, the algorithm may do an estimate to calculate where the input force may occur on the arm. The algorithm may read the type of input given, such as whether an input is a slow push, quick tap, a shake, or a pull. The algorithm can use a library of cases to toggle between different admittance modes. This library can be preset or adaptively learned. In some embodiments, the robotic arm may be response to voice or other commands in addition to or instead of touch commands.

In a step 4340, the robotic arm may be moved based on the determined user intent. In some embodiments, the admittance/impedance mode may be enabled based on the detected force, i.e., if the exerted force matches a pattern for enabling the admittance/impedance mode. The robotic arm may also move in a variety of patterns based on the characteristics of the force exerted on it. For example, it may be determined that the force exerted on the robotic arm comprises at least one tap on a joint of the robotic arm, and the joint of the robotic arm may be automatically moved while maintaining a position of at least one other joint or interface end of the arm. In another example, it may be determined that the force exerted on the robotic arm comprises a pull on an interface end of the robotic arm while a position of a joint of the robotic arm is maintained, and the interface end of the robotic arm may be simply rotated. In yet another example, it may be determined that the force exerted on the robotic arm comprises a push or pull on an interface end of the robotic arm, and the interface end of the robotic arm may be automatically moved in response to the push or pull on the interface end and the whole robotic arm may be automatically moved to follow the movement of the interface end.

In some embodiments, the behavior of another part of the robotic surgery system may change in response to the user exerted force or touch. For example, a double tap on the base of the robot may enable a pump. In one embodiment, a large or sudden force may set the robot into a "safe" state where no commands may be triggered by external force or touch. In another embodiment, a "master/slave" or "mirroring" mode may make use of force and torque readings from arms on one side of a surgical bed to command motions on arms on the other side of the bed.

In a step 4350, the admittance/impedance mode of the robotic surgery system may be disabled. In some embodiments, the robotic arm may return to the initial position it had memorized. In some embodiments, the robotic arm may be instructed to return to any of the preset positions previously memorized. The robotic arm may be instructed through any of the control schemes described herein. In some embodiments, admittance/impedance mode of the robotic surgery system may not be disabled after movement until operator command to do so.

Although the above steps show the method 4300 of manipulating the robotic arm(s) of a robotic surgery system in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as desired or beneficial.

One or more of the steps of the method 4300 may be performed with circuitry as described herein, for example, with one or more of a processor or logic circuitry such as a programmable array logic or field programmable gate array. The circuitry may be a component of the control console or control computing unit described herein. The circuitry may be programmed to provide one or more of the steps of the method 4300, and the program may comprise program instructions stored on a computer readable memory or programmed steps of the logic circuitry such as the programmable array logic or field programmable gate array, for example.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A method comprising:
  receiving, from a surgical robotic system comprising a first robotic arm coupled to a first position of a surgical instrument and a second robotic arm coupled to a second position of the surgical instrument, force feedback based on a force exerted on the surgical robotic system by a user of the surgical robotic system, the first position located at a predetermined distance from the second position, wherein the first robotic arm and the second robotic arm each include a torque sensor coupled to a joint of the corresponding robotic arm;
  determining whether the force feedback is a slow push, a tap, a double tap, a shake, or a strong pull;
  selecting an action for the robotic arms based on the determination regarding the force feedback, the selected action including one or more of: translating the robotic arms, rotating the robotic arms, stowing the robotic arms, and locking the robotic arms;
  determining a first movement vector and a second movement vector to perform the selected action using the robotic arms;
  providing, to the first robotic arm, a first command to move the surgical instrument along the first movement vector; and providing, to the second robotic arm, a second command to move the surgical instrument, simultaneously with the first robotic arm such that the predetermined distance is maintained, along the second movement vector.

2. The method of claim 1, wherein the surgical robotic system is configured to insert the surgical instrument along a trajectory into a patient in response to the first command and the second command.

3. The method of claim 2, wherein the trajectory includes a first segment and a second segment at an angle between 0 and 90 degrees relative to the first segment.

4. The method of claim 1, wherein the surgical instrument is flexible, and further comprising determining whether the surgical instrument is bending based on forces detected by the torque sensors.

5. The method of claim 1, further comprising:
receiving a second force exerted on the first robotic arm or the second robotic arm by a robotic arm of a second surgical robotic system; and
determining a position of the first robotic arm or the second robotic arm relative to the robotic arm of the second surgical robotic system.

6. The method of claim 1, wherein the first movement vector and the second movement vector are the same.

7. The method of claim 1, wherein the first movement vector and the second movement vector are different.

8. The method of claim 1, wherein the first robotic arm and the second robotic arm each include a plurality of segments coupled by one or more joints, and wherein the first robotic arm and the second robotic arm each include a plurality of tactile sensors, each tactile sensor configured to determine whether the user exerted the force in a vicinity of the tactile sensor.

9. The method of claim 8, further comprising determining whether the user exerted the force on a segment or a joint of the first robotic arm or the second robotic arm.

10. The method of claim 1, wherein the surgical robotic system further comprises a third robotic arm including a flange coupled to a third position of the surgical instrument.

11. The method of claim 10, wherein the flange includes a motorized roller configured to rotate at a speed based on motion of the third robotic arm.

12. The method of claim 1, wherein the surgical robotic system is configured to be controlled in an admittance mode or an impedance mode, the surgical robotic system configured to be controlled based on forces exerted on the surgical robotic system in the admittance mode, the surgical robotic system configured to be controlled based on input position commands in the impedance mode.

13. The method of claim 12, further comprising switching the surgical robotic system from the impedance mode to the admittance mode based on the force feedback.

14. A surgical robotic system comprising:
a first robotic arm coupled to a first position of a surgical instrument, the first robotic arm including a first torque sensor coupled to a joint of the first robotic arm;
a second robotic arm coupled to a second position of the surgical instrument, the first position located at a predetermined distance from the second position, the second robotic arm including a second torque sensor coupled to a joint of the second robotic arm; and
a controller configured to
receive force feedback based on a force exerted on the surgical robotic system by a user of the surgical robotic system;
determine whether the force feedback is a slow push, a tap, a double tap, a shake, or a strong pull;
select an action for the robotic arms based on the determination regarding the force feedback, the selected action including one or more of: translating the robotic arms, rotating the robotic arms, stowing the robotic arms, and locking the robotic arms;
determine a first movement vector and a second movement vector to perform the selected action using the robotic arms;
provide, to the first robotic arm, a first command to move the surgical instrument along the first movement vector; and
provide, to the second robotic arm, a second command to move the surgical instrument, simultaneously with the first robotic arm such that the predetermined distance is maintained, along the second movement vector.

15. The surgical robotic system of claim 14, wherein the surgical robotic system is configured to insert the surgical instrument along a trajectory into a patient in response to the first command and the second command.

16. The surgical robotic system of claim 15, wherein the trajectory includes a first segment and a second segment at an angle between 0 and 90 degrees relative to the first segment.

17. The surgical robotic system of claim 14, wherein the surgical instrument is flexible, and wherein the controller is further configured to determine whether the surgical instrument is bending based on forces detected by the first and second torque sensors.

18. The surgical robotic system of claim 14, wherein the controller is further configured to:
receive a second force exerted on the first robotic arm or the second robotic arm by a robotic arm of a second surgical robotic system; and
determine a position of the first robotic arm or the second robotic arm relative to the robotic arm of the second surgical robotic system.

19. The surgical robotic system of claim 14, wherein the first movement vector and the second movement vector are the same.

20. The surgical robotic system of claim 14, wherein the first movement vector and the second movement vector are different.

21. The surgical robotic system of claim 14, wherein the first robotic arm and the second robotic arm each include a plurality of segments coupled by one or more joints, and wherein the first robotic arm and the second robotic arm each include a plurality of tactile sensors, each tactile sensor configured to determine whether the user exerted the force in a vicinity of the tactile sensor.

22. The surgical robotic system of claim 21, wherein the controller is further configured to determine whether the user exerted the force on a segment or a joint of the first robotic arm or the second robotic arm.

23. The surgical robotic system of claim 14, wherein the surgical robotic system further comprises a third robotic arm including a flange coupled to a third position of the surgical instrument.

24. The surgical robotic system of claim 23, wherein the flange includes a motorized roller configured to rotate at a speed based on motion of the third robotic arm.

25. The surgical robotic system of claim 14, wherein the surgical robotic system is configured to be controlled in an admittance mode or an impedance mode, the surgical robotic system configured to be controlled based on forces exerted on the surgical robotic system in the admittance mode, the surgical robotic system configured to be controlled based on input position commands in the impedance mode.

\* \* \* \* \*